(12) United States Patent
Thaxton et al.

(10) Patent No.: US 10,967,072 B2
(45) Date of Patent: Apr. 6, 2021

(54) SHORT INTERFERING RNA TEMPLATED LIPOPROTEIN PARTICLES (SIRNA-TLP)

(71) Applicant: Northwestern University, Evanston, IL (US)

(72) Inventors: C. Shad Thaxton, Chicago, IL (US); Kaylin M. McMahon, Chicago, IL (US)

(73) Assignee: Northwestern University, Evanston, IL (US)

( * ) Notice: Subject to any disclaimer, the term of this patent is extended or adjusted under 35 U.S.C. 154(b) by 137 days.

(21) Appl. No.: 15/499,279

(22) Filed: Apr. 27, 2017

(65) Prior Publication Data

US 2017/0312365 A1   Nov. 2, 2017

Related U.S. Application Data

(60) Provisional application No. 62/328,175, filed on Apr. 27, 2016.

(51) Int. Cl.
| | | |
|---|---|---|
| *A61K 47/00* | (2006.01) | |
| *A61K 49/00* | (2006.01) | |
| *A61K 47/69* | (2017.01) | |
| *A61K 9/127* | (2006.01) | |
| *A61K 47/18* | (2017.01) | |

(52) U.S. Cl.
CPC ........ *A61K 47/6929* (2017.08); *A61K 9/1273* (2013.01); *A61K 9/1277* (2013.01); *A61K 47/183* (2013.01)

(58) Field of Classification Search
CPC .............. A61K 31/713; A61K 47/6929; A61K 47/6931; A61K 9/1277; A61P 35/00; C12N 15/111; C12N 15/113; C12N 2310/14; C12N 2320/52
USPC ...... 424/9.1; 435/6.1, 91.1, 91.31, 455, 458; 514/44; 536/23.1, 24.5
See application file for complete search history.

(56) References Cited

U.S. PATENT DOCUMENTS

| | | |
|---|---|---|
| 5,596,091 A | 1/1997 | Switzer |
| 8,323,686 B2 | 12/2012 | Mirkin et al. |
| 9,216,155 B2 | 12/2015 | Thaxton et al. |
| 9,532,948 B2 | 1/2017 | Mirkin et al. |
| 10,078,092 B2 | 9/2018 | Mutharasan et al. |
| 10,328,026 B2 | 6/2019 | Thaxton et al. |
| 10,413,565 B2 | 9/2019 | Plebanek et al. |
| 10,517,924 B2 | 12/2019 | Thaxton et al. |
| 10,568,898 B2 | 2/2020 | Thaxton et al. |
| 2004/0014956 A1 | 1/2004 | Woolf et al. |
| 2008/0181928 A1 | 7/2008 | Hakimi-Mehr et al. |
| 2008/0306016 A1 | 12/2008 | Mirkin et al. |
| 2009/0209629 A1 | 8/2009 | Mirkin et al. |
| 2010/0003317 A1 | 1/2010 | Akinc et al. |
| 2010/0136682 A1 | 6/2010 | Mirkin et al. |
| 2010/0166842 A1 | 7/2010 | Lu et al. |
| 2011/0020242 A1 | 1/2011 | Zheng et al. |
| 2011/0237435 A1 | 9/2011 | Ryan |
| 2013/0034599 A1 | 2/2013 | Thaxton et al. |
| 2013/0123333 A1 | 5/2013 | Mirkin et al. |
| 2013/0252852 A1 | 9/2013 | Pfeiffer et al. |
| 2014/0134658 A1 | 5/2014 | Ahrens et al. |
| 2015/0064255 A1 | 3/2015 | Thaxton et al. |
| 2016/0193361 A1 | 7/2016 | Thaxton et al. |
| 2016/0310425 A1 | 10/2016 | Mirkin et al. |
| 2018/0074080 A1 | 3/2018 | Thaxton et al. |
| 2019/0079105 A1 | 3/2019 | Mutharasan et al. |
| 2019/0365648 A1 | 12/2019 | Thaxton et al. |

FOREIGN PATENT DOCUMENTS

| | | |
|---|---|---|
| WO | WO 2010/105209 A1 | 9/2010 |
| WO | WO 2015/168393 A1 | 11/2015 |
| WO | WO 2018/237182 A1 | 12/2018 |

OTHER PUBLICATIONS

U.S. Appl. No. 16/384,749, (filed 2019).*
U.S. Appl. No. 16/779,740 (claims filed Feb. 20, 2020). (filed 2020).*
Acton et al., Identification of scavenger receptor SR-BI as a high density lipoprotein receptor. Science. Jan. 26, 1996;271(5248):518-20.
Cheng et al., The role of helper lipids in lipid nanoparticles (LNPs) designed for oligonucleotide delivery. Adv Drug Deliv Rev. Apr. 1, 2016;99(Pt A):129-137. doi: 10.1016/j.addr.2016.01.022. Epub Feb. 18, 2016. Review. Abstract Only.
Cutler et al., Spherical nucleic acids. J Am Chem Soc. Jan. 25, 2012;134(3):1376-91. doi: 10.1021/ja209351u. Epub Jan. 9, 2012.
Daniel et al., Gold nanoparticles: assembly, supramolecular chemistry, quantum-size-related properties, and applications toward biology, catalysis, and nanotechnology. Chem Rev. Jan. 2004;104(1):293-346. Review.
Ding et al., A biomimetic nanovector-mediated targeted cholesterol-conjugated siRNA delivery for tumor gene therapy. Biomaterials. Dec. 2012;33(34):8893-905. doi: 10.1016/j.biomaterials.2012.08.057. Epub Sep. 12, 2012. Abstract Only.
Giljohann et al., Gene regulation with polyvalent siRNA-nanoparticle conjugates. J Am Chem Soc. Feb. 18, 2009;131(6):2072-3.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.

(Continued)

*Primary Examiner* — Jane J Zara
(74) *Attorney, Agent, or Firm* — Wolf, Greenfield & Sacks, P.C.

(57) ABSTRACT

Nanostructures for the systemic delivery of nucleic acids, such as RNA, are provided herein. The nanostructures include templated lipoprotein nanoparticles (TLPs) composed of a core decorated with proteins, a lipid bilayer and hydrophobic molecules that self-assemble with nucleic acids, such as RNA. The nanostructures are useful for research, therapeutic and diagnostic applications.

27 Claims, 24 Drawing Sheets

Specification includes a Sequence Listing.

(56) References Cited

OTHER PUBLICATIONS

Kim, S. et al., "Systemic and Specific Delivery of Small Interfering RNAs to the Liver Mediated by Apolipoprotein A-I," Mol. Ther., 2007, 15 (6), 1145-1152.
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Li et al., Oligonucleotide-conjugated nanoparticles for targeted drug delivery via scavenger receptors class A: An in vitro assessment for proof-of-concept. Int J Pharm. Oct. 30, 2017;532(1):647-655. doi: 10.1016/j.ijpharm.2017.08.074. Epub Aug. 18, 2017.
Luthi et al., Robust passive and active efflux of cellular cholesterol to a designer functional mimic of high density lipoprotein. J Lipid Res. May 2015;56(5):972-85. doi: 10.1194/jlr.M054635. Epub Feb. 4, 2015.
Luthi et al., Tailoring of biomimetic high-density lipoprotein nanostructures changes cholesterol binding and efflux. ACS Nano. Jan. 24, 2012;6(1):276-85. doi: 10.1021/nn2035457. Epub Dec. 1, 2011.
Lv et al., Toxicity of cationic lipids and cationic polymers in gene delivery. J Control Release. Aug. 10, 2006;114(1):100-9. Epub May 13, 2006. Review. Abstract Only.
Maksymovych et al., Gold-adatom-mediated bonding in self-assembled short-chain alkanethiolate species on the Au(111) surface. Phys Rev Lett. Oct. 6, 2006;97(14):146103. Epub Oct. 6, 2006. Abstract Only.
McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.
McMahon et al., Properties of Native High-Density Lipoproteins Inspire Synthesis of Actively Targeted In Vivo siRNA Delivery Vehicles. Adv Funct Mater. Nov. 15, 2016;26(43):7824-7835. doi: 10.1002/adfm.201602600. Epub Sep. 20, 2016.
Mei et al., Lipid-free Apolipoprotein A-I Structure: Insights into HDL Formation and Atherosclerosis Development. Arch Med Res. Jul. 2015;46(5):351-60. doi: 10.1016/j.arcmed.2015.05.012. Epub Jun. 3, 2015. Review.
Patel et al., Scavenger receptors mediate cellular uptake of polyvalent oligonucleotide-functionalized gold nanoparticles, Bioconj. Chem., 21:2250 (2010).
Plebanek et al., Nanoparticle Targeting and Cholesterol Flux Through Scavenger Receptor Type B-1 Inhibits Cellular Exosome Uptake. Sci Rep. Oct. 29, 2015;5:15724. doi: 10.1038/srep15724.
Rosi et al., Oligonucleotide-modified gold nanoparticles for intracellular gene regulation. Science. May 19, 2006;312(5776):1027-30.
Schörghofer et al., The HDL receptor SR-BI is associated with human prostate cancer progression and plays a possible role in establishing androgen independence. Reprod Biol Endocrinol. Aug. 7, 2015;13:88. doi: 10.1186/s12958-015-0087-z.
Shahzad et al., Targeted delivery of small interfering RNA using reconstituted high-density lipoprotein nanoparticles. Neoplasia. Apr. 2011;13(4):309-19.
Suga et al., Conformational change of single-stranded RNAs induced by liposome binding. Nucleic Acids Res. Nov. 1, 2011;39(20):8891-900. doi: 10.1093/nar/gkr568. Epub Jul. 23, 2011.
Sun et al., Mesophase in a thiolate-containing diacyl phospholipid self-assembled monolayer. Langmuir. Mar. 17, 2015;31(10):3232-41. doi: 10.1021/la504822q. Epub Mar. 4, 2015. Abstract Only.
Tajik-Ahmadabad et al., Amphiphilic lipopeptide significantly enhances uptake of charge-neutral splice switching morpholino oligonucleotide in spinal muscular atrophy patient-derived fibroblasts. Int J Pharm. Oct. 30, 2017;532(1):21-28. doi:10.1016/j.ijpharm.2017.08.116. Epub Aug. 31, 2017. Abstract Only.
Thaxton et al., Templated Spherical High Density Lipoprotein Nanoparticles. J. Am. Chem. Soc., 2009, 131 (4), 1384-1385.
Van Eck et al., Scavenger receptor BI facilitates the metabolism of VLDL lipoproteins in vivo. J Lipid Res. Jan. 2008;49(1):136-46. Epub Oct. 22, 2007.
Vickers et al., . MicroRNAs are transported in plasma and delivered to recipient cells by high-density lipoproteins. Nat Cell Biol. Apr. 2011;13(4):423-33. doi: 10.1038/ncb2210. Epub Mar. 20, 2011. Erratum in: Nat Cell Biol. Jan. 2015;17(1):104.
Whitehead et al., Knocking down barriers: advances in siRNA delivery, Nat. Rev. Drug. Discov., 8:129 (2009).
Wolfrum et al., Mechanisms and optimization of in vivo delivery of lipophilic siRNAs. Nat Biotechnol. Oct. 2007;25(10):1149-57. Epub Sep. 16, 2007.
Yang et al., Overcoming the inhibitory effect of serum on lipofection by increasing the charge ratio of cationic liposome to DNA. Gene Ther. Sep. 1997;4(9):950-60. Abstract Only.
Zhang et al., Cationic lipids and polymers mediated vectors for delivery of siRNA. J Control Release. Oct. 18, 2007;123(1):1-10. Epub Aug. 7, 2007. Review. Abstract Only.
Zhang et al., HDL-mimicking peptide-lipid nanoparticles with improved tumor targeting. Small. Feb. 5, 2010;6(3):430-7. doi: 10.1002/smll.200901515. Abstract Only.
Zhang et al., Structure-activity relationships of cationic shell-crosslinked knedel-like nanoparticles: shell composition and transfection efficiency/cytotoxicity, Biomaterials, 31: 1805 (2010).
U.S. Appl. No. 16/384,749, filed Apr. 15, 2019, Thaxton et al.
U.S. Appl. No. 16/059,476, filed Aug. 9, 2018, Mutharasan et al.
U.S. Appl. No. 14/911,476, filed Feb. 12, 2016, Thaxton et al.
U.S. Appl. No. 15/706,648, filed Sep. 15, 2017, Thaxton et al.
Cheng et al., The role of helper lipids in lipid nanoparticles (LNPs) designed for oligonucleotide delivery. Adv Drug Deliv Rev. Apr. 1, 2016;99(Pt A):129-137. doi: 10.1016/j.addr.2016.01.022. Epub Feb. 18, 2016. Review.
Ding et al., A biomimetic nanovector-mediated targeted cholesterol-conjugated siRNA delivery for tumor gene therapy. Biomaterials. Dec. 2012;33(34):8893-905. doi: 10.1016/j.biomaterials.2012.08.057. Epub Sep. 12, 2012.
Lv et al., Toxicity of cationic lipids and cationic polymers in gene delivery. J Control Release. Aug. 10, 2006;114(1):100-9. Epub May 13, 2006. Review.
Maksymovych et al., Gold-adatom-mediated bonding in self-assembled short-chain alkanethiolate species on the Au(111) surface. Phys Rev Lett. Oct. 6, 2006;97(14):146103. Epub Oct. 6, 2006.
Sun et al., Mesophase in a thiolate-containing diacyl phospholipid self-assembled monolayer. Langmuir. Mar. 17, 2015;31(10):3232-41. doi: 10.1021/la504822q. Epub Mar. 4, 2015.
Tajik-Ahmadabad et al., Amphiphilic lipopeptide significantly enhances uptake of charge-neutral splice switching morpholino oligonucleotide in spinal muscular atrophy patient-derived fibroblasts. Int J Pharm. Oct. 30, 2017;532(1):21-28. doi:10.1016/j.ijpharm.2017.08.116. Epub Aug. 31, 2017.
Yang et al., Overcoming the inhibitory effect of serum on lipofection by increasing the charge ratio of cationic liposome to DNA. Gene Ther. Sep. 1997;4(9):950-60.
Zhang et al., Cationic lipids and polymers mediated vectors for delivery of siRNA. J Control Release. Oct. 18, 2007;123(1):1-10. Epub Aug. 7, 2007. Review.
Zhang et al., HDL-mimicking peptide-lipid nanoparticles with improved tumor targeting. Small. Feb. 5, 2010;6(3):430-7. doi: 10.1002/smll.200901515.
U.S. Appl. No. 16/799,740, filed Feb. 24, 2020, Thaxton et al.
U.S. Appl. No. 16/063,546, filed Jun. 18, 2018, Rink et al.
U.S. Appl. No. 16/083,465, filed Sep. 7, 2018, Thaxton et al.
U.S. Appl. No. 16/625,340, filed Dec. 20, 2019, Thaxton et al.
Marrache et al., Biodegradable synthetic high-density lipoprotein nanoparticles for atherosclerosis. PNAS, 2013;110(23):9445-50.

* cited by examiner

| | TLP | AR-TLP | Ctrl-TLP |
|---|---|---|---|
| apo A-I (M) : Au NP (M) | 2 ± 1 | 2 ± 1 | 2 ± 1 |
| Cholesterol (M) : Au NP (M) | 18 ± 10 | 14 ± 3 | 10 ± 3 |
| DOPC (M) : Au NP (M) | 47 ± 10 | 48 ± 7 | 34 ± 8 |
| DOTAP (M) : Au NP (M) | N/A | 969 ± 250 | 960 ± 61 |
| Sense Strand (M) : Au NP (M) | N/A | 6 ± 1 | 5 ± 2 |
| Antisense Strand (M) : Au NP (M) | N/A | 8 ± 3 | 8 ± 2 |

FIG. 9A  FIG. 9B

've been shown to increase siRNA stability, improve circulating half-life, and enhance cell uptake. However, toxicity, serum opsonization, and lack of active targeting remain significant drawbacks to cationic siRNA delivery vehicles (Lv, H. et al., J Control Release. 2006; 114(1):100-9; and Yang et al., Gene Ther. 1997; 4:950-960). Ultimately, identifying simple strategies for formulating largely unmodified siRNAs and alternatives to passively targeted cationic delivery vehicles are important for developing the next generation of therapeutic siRNAs.

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1
gcauucuuaa acucguaaat t                                       21

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by phosphate

<400> SEQUENCE: 2
uuuacgaguu uaagaaugca a                                       21

<210> SEQ ID NO 3
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Modified by Cy3 or Cy5

<400> SEQUENCE: 3
gcauucuuaa acucguaaat t                                       21

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by phosphate
<220> FEATURE:
<221> NAME/KEY: misc_feature
<222> LOCATION: (21)..(21)
<223> OTHER INFORMATION: Modified by Cy5

<400> SEQUENCE: 4
uuuacgaguu uaagaaugca a                                       21

<210> SEQ ID NO 5
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 5
gcccauugac uauuacuuut t                                       21

<210> SEQ ID NO 6
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by phosphate

<400> SEQUENCE: 6

```
aaaguaauag ucaaugggca a                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(21)
<223> OTHER INFORMATION: Modified by Cy3 or Cy5

<400> SEQUENCE: 7
gcccauugac uauuacuuut t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by phosphate
<220> FEATURE:
<221> NAME/KEY: misc_feature
<222> LOCATION: (21)..(21)
<223> OTHER INFORMATION: Modified by Cy5

<400> SEQUENCE: 8
aaaguaauag ucaaugggca a                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 9
gagguucaga cgagcugaut t                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by phosphate

<400> SEQUENCE: 10
aucagcucgt cugaaccuca a                                              21
```

SHORT INTERFERING RNA TEMPLATED LIPOPROTEIN PARTICLES (SIRNA-TLP)

RELATED APPLICATIONS

This application claims the benefit under 35 U.S.C. § 119(e) of U.S. provisional application Ser. No. 62/328,175, filed Apr. 27, 2016, the entire contents of which is incorporated by reference herein.

GOVERNMENT SUPPORT

This invention was made with Government support under Grant No. R01CA167041 awarded by the National Institutes of Health. The government has certain rights in the invention.

FIELD OF INVENTION

The present invention generally relates to products and methods of using templated lipoprotein particles (TLPs) that self-assemble with short interfering RNA (siRNA) for therapy.

BACKGROUND

Systemic administration of therapeutic short interfering RNA (siRNA) is tremendously appealing due to the ability of siRNA to potently silence any protein target and the opportunities that exist for personalized medicine (Wu et al., Sci Transl Med, 2014 6(240):240ps7). Some progress has been made with recent clinical trials demonstrating systemic delivery of therapeutic siRNA; however, drugs mostly target protein expression in the liver and none are approved by the U.S. Food and Drug Administration (FDA) (Wu et al., Sci Transl Med, 2014; 6(240):240ps7; and Whitehead et al., Nat Rev Drug Discov. 2009; 8(2):129-38). More specific to oncology applications, only four systemically administered agents have reached Phase I clinical trials, one was actively targeted, one moved on to Phase II, and none have gained FDA approval (Zuckerman et al., Nat Rev Drug Discov. 2015; 14(12):843-56). Ultimately, targeted systemic delivery of therapeutic siRNA remains difficult due to a number of well-known factors, such as: (1) inherent siRNA instability, (2) inefficient active delivery to target cells, (3) exclusion of siRNA from the target cell cytosol where mRNA targets reside, (4) RNA target selection, (5) toxicity, and (6) complexity, scalability, and cost (Choi et al., Mol Cell Toxicol. 2014; 10:1-8; Nguyen et al., Curr Opin Mol Ther. 2008; 10:158-167; Singh et al., Curr Opin Biotechnol. 2016; 39:28-34; and Cheng et al., Science. 2012; 338:903-910. In short, realizing the full potential of systemically administered therapeutic siRNA, especially for advanced solid tumors, requires the development of new technology.

Individual and combinations of strategies have been employed to enhance the efficacy of therapeutic siRNA. Notably, chemical modifications to the siRNA phosphate backbone and/or ribose sugar have improved RNA stability and can limit off-target effects.[8] However, chemical modifications can significantly increase cost, may generate off-target effects, and can reduce siRNA efficacy (McMahon et al., Expert Opin Drug Deliv. 2014; 11(2):231-47). In addition, many siRNA delivery vehicles have been developed. Almost exclusively, delivery vehicles are formed by self-assembling cationic lipids (lipoplexes) or polymers (polyplexes) that encapsulate siRNAs (Zhang et al., J Control Release. 2007; 123(1):1-10). Some of these cationic vehicles

SUMMARY OF THE INVENTION

According to one aspect, the invention is a nanostructure which includes a templated lipoprotein particle (TLP) that includes a core, a lipid shell surrounding the core, an apolipoprotein; and single stranded antisense and sense RNA of an siRNA duplex associated with the lipid.

In some embodiments, the core of the nanostructure is a metal. Optionally, in another embodiment, the core of the nanostructure is gold.

In some embodiments, the lipids in the lipid shell are phospholipids. Optionally, in another embodiment, the phospholipids are 1,2-dioleoyl-sn-glycero-3-phophocholine (DOPC) and 1,2-dipalmitoyl-sn-glycero-3-phosphoethanolamine-N-[3-(2-pyridyldithio)propionate] (PDP-PE).

In some embodiments, the apolipoprotein of the nanostructure is apolipoprotein A-1 (apo A-1). Optionally, in some embodiments, the nanostructure contains cholesterol.

In some embodiments, the RNA in the nanostructure is more stable than free RNA.

In some embodiments, the nanostructure contains alternating layers of 1,2-dioleoyl-3-trimethylammonium-propane (DOTAP) and RNA. In another embodiment, optionally, the RNA is not chemically modified. In another embodiment, the sense and antisense RNA are present in equimolar amounts.

In some embodiments, the RNA is mixed with TLP in a molar ratio of 5:1, 15:1 or 25:1. In another embodiment, optionally, the RNA is mixed with TLP in a molar ratio of 25:1.

In some embodiments, the RNA is complexed to the cationic lipid DOTAP. In another embodiment, optionally, the DOTAP is mixed with RNA in a molar ratio of 10:1, 20:1, 30:1 or 40:1. In yet another embodiment, optionally, DOTAP is mixed with RNA in a molar ratio of 30:1 or 40:1. In an embodiment, optionally, DOTAP is mixed with RNA in a molar ratio of 40:1. In yet another embodiment, DOTAP is mixed with RNA in a charge ratio of about 1:4, 2:1, 3:4 or 1:1.

In some embodiments, DOTAP is mixed with RNA in a molar ratio of 40:1 and the RNA is mixed with TLP in a molar ratio of 25:1.

According to another aspect, the invention is a synthetic stable nanostructure that includes an anionic templated lipoprotein particle (TLP) comprising a core, a lipid bilayer shell surrounding the core, a cholesterol associated with the lipid bilayer and an apolipoprotein, wherein the TLP has an anionic charge of about −35 to −50 mV.

In some embodiments, the core of the synthetic stable nanostructure is a metal. In another embodiment, optionally, the core of the nanostructure is gold.

In some embodiments, the lipids in the lipid bilayer shell are phospholipids. In another embodiment, optionally, the phospholipids are DOPC and PDP-PE.

According to another aspect, the invention is a method for delivering siRNA to a cell, wherein in the method includes contacting a cell with a nanostructure described herein to deliver siRNA to the cell.

In some embodiments, the cell is in a subject. In yet another embodiment, the cell is a cancer cell. In another embodiment, optionally, the cancer cell is a prostate cancer cell, a breast cancer cell, a renal cancer cell or an ovarian cancer cell.

In some embodiments, the cell is a LNCaP cell, an enzalutamide resistant LNCaP cell, a MDA-MB-231 cell, a 786-O cell, or a OvCar3 cell.

In some embodiments, the cell is contacted with the nanostructure at a concentration of 5 nM, 10 nM, or 20 nM.

In some embodiments, the cell is in contact with the nanostructure for 24, 48, 72, and 96 hours.

In some embodiments, the cancer cell expresses the androgen receptor (AR) or the enhancer of zeste homolog 2 (EZH2) proteins.

In some embodiments, the subject is a mammal. In some embodiments, the subject is human.

According to another aspect, the invention is a method for treating a cancer, wherein the method comprises systemically administering to a subject having a cancer a nanostructure described herein to deliver siRNA to the subject and treat the cancer, wherein the siRNA is an anti-cancer siRNA.

In some embodiments, the nanostructure is administered in vivo.

In yet another embodiment, the subject is a mammal. In another embodiment, optionally, the subject is a human.

In some embodiments, the nanostructure is administered at a concentration of about 0.7 mg siRNA/kg.

In some embodiments, the nanostructure is not toxic to a surrounding non-cancerous cell or non-cancerous tissue.

According to another aspect, the invention is a method of regulating gene expression in a cell with a nanostructure described herein.

In some embodiments, the nanostructure decreases the expression of a gene. In another embodiment, optionally, the nanostructure decreases the expression of the gene that encodes for the AR protein. In yet another embodiment, the nanostructure decreases the expression of the gene that encodes for the EZH2 protein.

According to another aspect, the invention is a method of treating an autoimmune disorder, the method comprising administering to a subject a nanostructure described herein.

In some embodiments, the nanostructure has a diameter of about 110 nm.

According to another aspect, the invention is a nanostructure described herein that further delivers a drug.

According to another aspect, the invention is a nanostructure described herein that further delivers an adjuvant.

According to another aspect, the invention is a nanostructure described herein that further delivers a vaccine adjuvant.

According to another aspect, the invention is a nanostructure described herein that includes an antigen that enhances antigen presentation in a cell.

According to another aspect, the invention is a method of synthesizing an siRNA delivery vehicle that includes contacting a TLP that includes a core, a lipid shell surrounding the core, and an apolipoprotein with single stranded antisense and sense RNA of an siRNA duplex formulated in a cationic acid.

In some embodiments, the cancer comprises a cancer cell, wherein the cancer cell overexpresses a scavenger receptor class B type I (SR-BI), relative to a non-cancer cell or relative to a cancer cell that does not overexpress SR-BI.

According to another aspect, the invention is a method for synthesizing a TLP, wherein the method includes contacting gold nanoparticles with an apolipoprotein to produce an apolipoprotein coated gold particle, contacting the apolipoprotein coated gold particle with two phospholipids to produce an anionic TLP.

In some embodiments, optionally, the method further includes mixing the anionic TLP with a DOTAP RNA mixture.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and Figures. Other features, objects, and advantages of the invention will be apparent from the description and from the claims.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

(FIG. 1A) In Step 1, TLPs are synthesized. In Step 2, TLPs are mixed with single-strand RNA (ssRNA), complement strands of a siRNA duplex, complexed with DOTAP. (FIG. 1B) UV-Vis spectroscopy measurement of nanoparticle ($\lambda_{max}$~520 nm) and RNA ($\lambda_{max}$~260 nm) after centrifugation for purification from unreacted components. (FIG. 1C) ζ-potential measurement of TLPs, DOTAP-TLPs and siRNA-TLP particles synthesized with increasing DOTAP:RNA molar ratios from 10:1-40:1. (FIG. 1D) Hydrodynamic diameter (nm) measurement of 5 nm Au NP, TLP, and siRNA-TLP particles synthesized with increasing DOTAP:RNA molar ratios from 10:1-40:1. (FIG. 1E) UV-Vis spectroscopy measuring purified siRNA-TLPs synthesized with increasing DOTAP:RNA molar ratios. (FIG. 1F) Western blot of siRNA-TLP function regulating target AR expression in LNCaP cells (48 hrs, 20 nM siRNA-TLP). All UV-Vis spectra were normalized according to $\lambda_{max}$~520 nm. AR=siRNA targeting the androgen receptor. Ctrl=scrambled control siRNA sequence. Lipo=LIPOFECTAMINE® RNAiMAX.

(FIG. 2A) Table depicting the molar ratio of each particle component in TLP and siRNA-TLP following purification and quantification. (FIG. 2B) Transmission electron microscopy of TLP and siRNA-TLP. Scale bar=50 nm. (FIG. 2C) Western blot of siRNA-TLPs function to regulate AR expression using particles synthesized with either the sense (S), antisense (AS), or both strands of the siRNA duplex pair (DS) in LNCaP cells (48 hrs). (FIG. 2D) Western blot of siRNA-TLPs function to regulate AR expression when formulated with either both RNA complements (DS) on a single siRNA-TLP, or a mixed population of AS and S siRNA-TLPs combined as a single treatment in LNCaP cells (48 hrs, 20 nM siRNA-TLP). AR=siRNA targeting the androgen receptor. Ctrl=scrambled control siRNA sequence. Lipo=LIPOFECTAMINE® RNAiMAX.

(FIG. 3A) Western blot time course of siRNA-TLP function regulating AR expression in LNCaP cells. (FIG. 3B) Cell viability of LNCaP cells after treatment with siRNA-TLPs measured by MTS assay (1, 5, 10, 20 nM siRNA-TLP). (FIG. 3C) LNCaP cell confluence measured over time after treatment with siRNA-TLPs (20 nM), and images taken 165 hours after siRNA-TLP treatment depicting cell confluence. AR=siRNA targeting the androgen receptor. Ctrl=scrambled control siRNA sequence. Lipo=LIPOFECTAMINE® RNAiMAX.

(FIG. 4A) Cellular uptake of siRNA-TLP by LNCaP cells measured by fluorescent signal in cells over time using an Incucyte ZOOM (20 nM siRNA-TLP). (FIG. 4B) Representative fluorescent images of siRNA-TLP uptake (72 hrs). (FIG. 4C) Western blot of LNCaP cells pre-treated with SR-B1 and Ctrl siRNA 48 hrs prior to siRNA-TLPs addition to determine if function is dependent on cellular SR-B1 expression. The hours in parenthesis indicate the total treatment time of siRNA sequences added using LIPOFECTAMINE® RNAiMAX. LNCaP cells were treated with siRNA-TLPs for 48 hrs. Quantification of western blot data. AR=siRNA targeting the androgen receptor. Ctrl=scrambled control siRNA sequence. Lipo=LIPOFECTAMINE® RNAiMAX.

(FIG. 5A) RNA stability of siRNA-TLPs compared to free RNA sequences upon exposure to RNase A. (FIG. 5B) RNA stability of siRNA-TLPs compared to free RNA sequences after exposure to human plasma. (FIG. 5C) Western blot of AR protein expression after treatment of LNCaP cells with TLPs and siRNA-TLPs that have been incubated in human serum (48 hrs, 20 nM siRNA-TLP), and serum supernatant (SN) fraction containing only albumin and HDL separated from siRNA-TLPs. The particle type added to human serum is indicated in parenthesis. AR=siRNA targeting the androgen receptor. Ctrl=scrambled control siRNA sequence. Lipo=LIPOFECTAMINE® RNAiMAX.

(FIG. 6A) Tumor volume measurements of LNCaP xenografts in athymic nude mice over course of in vivo study. (FIG. 6B) The percent change in LNCaP tumor volume over course of in vivo study. (FIG. 6C) Inductively coupled plasmon mass spectrometry to measure Au NPs in tissues after treatment with siRNA-TLP or water. (FIG. 6D) LNCaP tumor uptake of sense (Cy3) and antisense (Cy5) labeled siRNA sequences assembled with siRNA-TLPs following a single systemic administration. Labeled RNA was visualized using confocal fluorescence microscopy 24 hours after injection. Tumor tissues were counterstained with DAPI. (FIG. 6E) Hematocrit (HCT), hemoglobin (HGB), and platelet (PLT) count in whole blood collected from study mice following treatment. (FIG. 6F) White blood cell (WBC) and neutrophil count from study mice following treatment. AR=siRNA targeting the androgen receptor. Ctrl=scrambled control siRNA sequence.

(FIG. 7A) RNA melting transition in water, PBS, and 9:1 water:ethanol (v/v) for AR+DOTAP sample (40:1 DOTAP:RNA). (FIG. 7B) ζ-potential of DOTAP liposomes, free RNA, and DOTAP-RNA mixtures of DOTAP:RNA ratios, whereby 40, 30, 20, 10 represent molecules of DOTAP per RNA phosphate (i.e. charge ratios of ~1:1, 3:4, 1:2, 1:4). (FIG. 7C) Hydrodynamic diameter of particles formed with DOTAP-RNA mixtures (FIG. 7D) Western blot of DOTAP-RNA particles targeting AR in LNCaP cells (48 hrs). Total RNA concentration of DOTAP-RNA mixtures to treat cells was equivalent to a 20 nM siRNA-TLP. (FIG. 7E) UV-Vis spectroscopy of purified siRNA-TLPs synthesized with increasing RNA:TLP ratios, whereby 25, 15, and 5 represent the fold molar excess of RNA molecules to TLP. UV-Vis spectra were normalized according to nanoparticle peak ($\lambda_{max}$~520 nm), siRNA loading is shown by $\lambda_{max}$~260 nm. (FIG. 7F) Western blot of siRNA-TLP targeting AR in LNCaP cells according to RNA:TLP ratios specified above (48 hrs).

FIGS. 9A-9D show in vitro function and modular loading. (FIG. 9A) qRT-PCR of LNCaP cells after treatment with siRNA-TLPs to measure AR mRNA expression (48 hrs). (FIG. 9B) Western blot of siRNA-TLPs targeting AR in LNCaP enzultamide resistant cells (48 hrs). (FIG. 9C) UV-Vis spectroscopy of siRNA-TLP with siRNA targeting AR (AR-TLP), EZH2 (EZH2-TLP) or Ctrl-TLP reveals equal amounts of siRNA ($\lambda_{max}$~260 nm). UV-Vis spectra were normalized according to nanoparticle peak ($\lambda_{max}$~520 nm). (FIG. 9D) Western blot of siRNA-TLPs targeting EZH2 in multiple cancer cell lines, including prostate cancer (LNCaP) and (LNCaP enzalutamide resistant), triple negative breast cancer (MDA-MB-231), renal cell carcinoma (786-O), and ovarian cancer (OvCar3) (48 hrs).

(FIG. 10A) Cy5-labeled siRNA-TLP uptake in LNCaP cells represented by mock fluorescent images obtained using an IncuCyte ZOOM at 6, 62, and 165 hours after particle incubation. siRNA-TLP attachment to cell (6 hrs), siRNA-TLP diffusion in cell (62 hrs), siRNA-TLP perinuclear localization (165 hrs). Note reduced cell confluency secondary to AR knockdown in AR-TLP samples (bottom). Scale bars=300 μm. (FIG. 10B) SR-B1 expression in cancer cells treated with siRNA-TLPs, including prostate (LNCaP), LNCaP cells that are resistant to enzalutamide (LNCaP MDV3100), triple negative breast cancer (MDA-MB-231), renal cell carcinoma (786-O), and ovarian cancer (OvCar3). (FIG. 10C) Western blot of SR-B1 knockdown in LNCaP cells over time. SR-B1 and Ctrl siRNA were transfected using LIPOFECTAMINE® RNAiMAX (Lipo).

12A) Treatment regimen for mice bearing LNCaP flank tumor xenografts. (FIG. 12B) Mouse weight over the course of the study. (FIG. 12C) H&E images of representative organs obtained from mice treated with water, Ctrl-TLP, and AR-TLP at study conclusion. H&E images were obtained 10× magnification.

(FIG. 13A) Serum chemistry, kidney function, and cholesterol analysis. (FIG. 13B) Liver function analysis. BUN=blood urea nitrogen, TP=total protein, AST=aspartate aminotransferase, ALT=alanine aminotransferase, ALK=alkaline phosphatase, ALB=albumin, TBIL=total bilirubin.

DETAILED DESCRIPTION

Figure 1A:
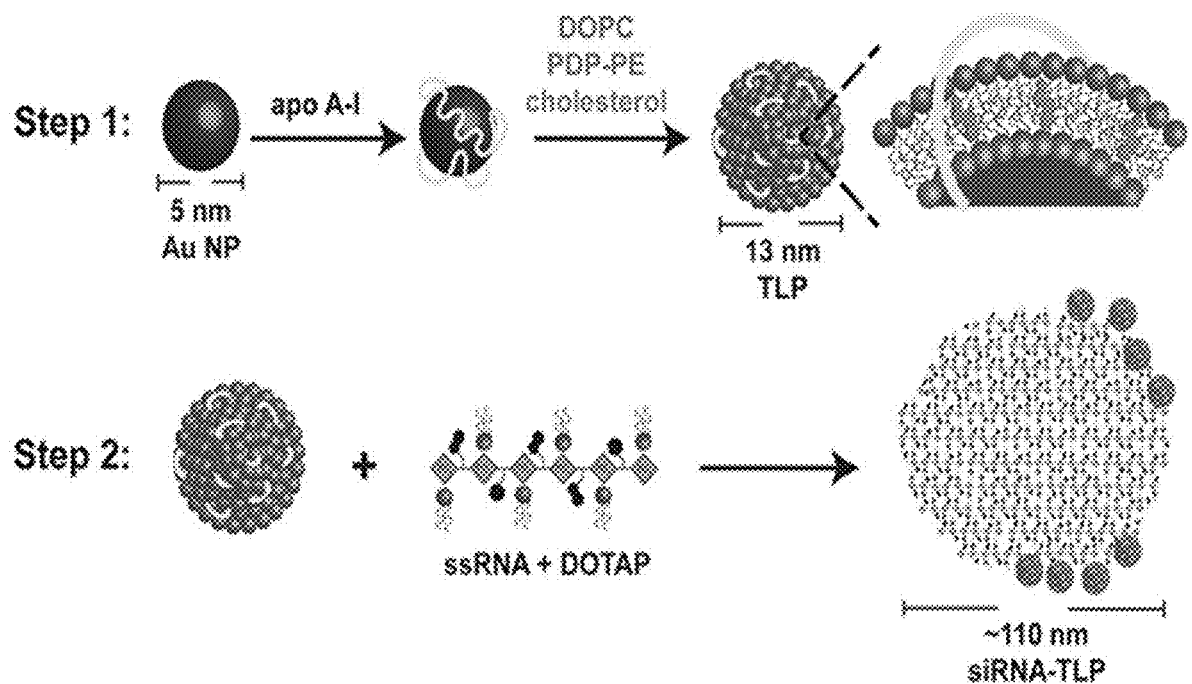
FIGS. 1A-1F show a scheme for siRNA-TLP synthesis, optimization, and function.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Efficient systemic administration of therapeutic short interfering RNA (siRNA) is challenging. The present disclosure presents a paradigm changing approach to systemic therapeutic siRNA delivery by self-assembling single-stranded highly unmodified RNA complements of an siRNA duplex pair in anionic delivery vehicles that are inherently actively targeted. The approach was inspired and designed according to properties of natural RNA delivery vehicles, namely, high density lipoproteins (HDLs). The siRNA-templated lipoprotein particles (siRNA-TLPs) presented herein are a combination of synthetic bio-inspired lipoproteins and cationic lipid-RNA assemblies. Some aspects of the present disclosure detail the process of controlled self-assembly and the exquisite functional tunability of siRNA-TLPs, the modular nature allowing easy exchange of therapeutic siRNA cargo, active cell targeting, potent target gene regulation, and in vivo efficacy after systemic administration.

High-density lipoproteins (HDL) are natural in vivo RNA delivery vehicles. The present disclosure uses the features of HDL to develop templated lipoprotein particles (TLP) that self-assemble with single-strand complements of, presumably, any highly unmodified siRNA duplex pair after formulation with a cationic lipid. Resulting siRNA templated lipoprotein particles (siRNA-TLP) are anionic and tunable with regard to RNA assembly and function. Quite surprisingly, siRNA-TLP are able to potently reduce gene expression in vitro. Another surprising aspect of the disclosure, as also shown herein, is that the systemic administration of siRNA-TLPs in vivo significantly reduces the growth of cancer xenografts and demonstrates no off-target toxicity. The present disclosure presents a modular approach to siRNA delivery by self-assembling single-strand complements of siRNA into actively targeted anionic delivery vehicles that potently regulate target gene expression in vitro and in vivo.

The present disclosure provides profound fundamental insight into methods of synthesizing next generation siRNA delivery vehicles for translation.

Nearly all of the technologies presently available for the systemic delivery of siRNA are based upon cationic lipids or cationic polymers. Most often, due to the cationic nature of these vehicles and the synthetic properties, they can be highly toxic and are not typically targeted to disease specific sites. The present disclosure overcomes the barriers to systemic RNA therapy because the nanostructure described herein is formulated such that it is anionic and inherently targeted through specific receptors located on the surface of cells.

Furthermore, many RNA therapies are designed around specific disease targets. However, the formulation described herein is highly modular, such that the siRNA-TLP can be tailored to incorporate presumably any protein target of interest. Additionally, most current techniques are not easily scaled and have unknown biological composition(s), which can lead to in vivo toxicity. The formulation described herein has been demonstrated in vivo to have no inherent toxicity and it is formulated to mimic natural RNA delivery vehicles to circumvent vehicle-related toxicity.

In some aspects, the nanoparticles of the present disclosure incorporate highly unmodified single-stranded complements of a desired siRNA duplex in templated lipoprotein particles that mimic the structure of natural HDL, which is an anionic delivery vehicle for unmodified nucleic acids. In certain embodiments of the present disclosure, the templated lipoprotein particle (TLP) inspired on HDL are typically composed of a core, surrounded by apolipoproteins, and a mixture of two phospholipids that form a lipid bilayer; and a hydrophobic molecule (e.g., cholesterol). The TLP associates with a cationic lipid complexed with a nucleic acid, such as a single-strand of a duplex siRNA, to form a nanostructure described herein.

The nanostructure of the present disclosure has several useful applications, including but not limited to, cancer therapy, autoimmune disease or disorder therapy, drug delivery, antigen/adjuvant delivery vehicle, vaccine adjuvant, enhanced antigen presentation, or as co-therapy with current cancer therapies and immunomodulators.

The cancer may be a malignant or non-malignant cancer. Cancers or tumors include, but are not limited to, biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment, the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma. In another embodiment, the cancer is prostate cancer, breast cancer, renal cancer or ovarian cancer.

In some embodiments, that nanostructures described herein are useful for treating a cancer that overexpresses scavenger receptor class B type I (SR-BI). Non-limiting examples of cancers that overexpress SR-BI include human prostate cancer, breast cancer, and renal cell carcinoma.[21, 42-44] Additional non-limiting examples of cancers and cancer cell lines that overexpress SR-BI are listed in Rajora et al. *Front Pharmacol.* (2016) 7:326. As described herein, the term "overexpression" or "increased expression," refers to an increased level of expression of a given gene product in a given cell, cell type or cell state, as compared to a reference cell, for example, a non-cancer cell or a cancer cell that does not overexpress SR-BI.

The nanostructures are also useful for treating and preventing autoimmune disease or disorder. Autoimmune disease or disorder is a class of diseases in which an subject's own antibodies react with host tissue or in which immune effector T cells are autoreactive to endogenous self peptides and cause destruction of tissue. Thus, an immune response is mounted against a subject's own antigens, referred to as self antigens. Autoimmune diseases or disorders include, but are not limited to, rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

The nanostructure of the present disclosure includes a core. The core may be a solid or a hollow core, such as a liposomal core. A solid core is a spherical shaped material that does not have a hollow center. The term spherical as used herein refers to a general shape and does not imply or is not limited to a perfect sphere or round shape. It may include imperfections.

The core of the nanostructure whether being a solid core or a hollow core, may have any suitable shape and/or size. For instance, the core may be substantially spherical, non-spherical, oval, rod-shaped, pyramidal, cube-like, disk-shaped, wire-like, or irregularly shaped. The core (e.g., a nanostructure core or a hollow core) may have a largest cross-sectional dimension (or, sometimes, a smallest cross-section dimension) of, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, the core has an aspect ratio of greater than about 1:1, greater than 3:1, or greater than 5:1.

The core may be formed of an inorganic material. The inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least 1 wt %, 5 wt %, 10 wt %, 25 wt %, 50 wt %, 75 wt %, 90 wt %, or 99 wt %. In one embodiment, the core is formed of 100 wt % inorganic material. The core may, in some cases, be in the form of a quantum dot, a carbon nanotube, a carbon nanowire, or a carbon nanorod. In some cases, the core comprises, or is formed of, a material that is not of biological origin. In some embodiments, a nanostructure includes or may be formed of one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen. In addition, these cores may be inert, paramagnetic, or supramagnetic. These solid cores can be constructed from either pure compositions of described materials, or in combinations of mixtures of any number of materials, or in layered compositions of materials. In addition, solid cores can be composed of a polymeric core such as amphiphilic block copolymers, hydrophobic polymers such as polystyrene, poly(lactic acid), poly(lactic co-glycolic acid), poly(glycolic acid), poly(caprolactone) and other biocompatible polymers known to those skilled in the art.

Furthermore, a shell of a structure can have any suitable thickness. For example, the thickness of a shell may be at least 10 Angstroms, at least 0.1 nm, at least 1 nm, at least 2 nm, at least 4 nm, at least 5 nm, at least 7 nm, at least 10 nm, at least 15 nm, at least 20 nm, at least 30 nm, at least 50 nm, at least 100 nm, or at least 200 nm (e.g., from the inner surface to the outer surface of the shell). In some cases, the thickness of a shell is less than 200 nm, less than 100 nm, less than 50 nm, less than 30 nm, less than 20 nm, less than 15 nm, less than 10 nm, less than 7 nm, less than 5 nm, less than 3 nm, less than 2 nm, or less than 1 nm (e.g., from the inner surface to the outer surface of the shell).

The shell of a structure described herein may comprise any suitable material, such as a hydrophobic material, a hydrophilic material, and/or an amphiphilic material. Although the shell may include one or more inorganic materials such as those listed above for the nanostructure core, in many embodiments the shell includes an organic material such as a lipid or certain polymers. The components of the shell may be chosen, in some embodiments, to facilitate the binding capacity.

In one set of embodiments, a structure described herein or a portion thereof, such as a shell of a structure, includes one or more natural or synthetic lipids or lipid analogs (i.e., lipophilic molecules). One or more lipids and/or lipid analogues may form a single layer or a multi-layer (e.g., a bilayer) of a structure. In some instances where multi-layers are formed, the natural or synthetic lipids or lipid analogs interdigitate (e.g., between different layers). Non-limiting examples of natural or synthetic lipids or lipid analogs include fatty acyls, glycerolipids, glycerophospholipids, sphingolipids, saccharolipids and polyketides (derived from condensation of ketoacyl subunits), and sterol lipids and prenol lipids (derived from condensation of isoprene subunits).

In one particular set of embodiments, a structure described herein includes one or more phospholipids. The one or more phospholipids may include, for example, phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, 1,2-dipalmitoyl-sn-glycero-3-phosphothioethanol, and combinations thereof. In some cases, a shell (e.g., a bilayer) of a structure includes 50-200 natural or synthetic lipids or lipid analogs (e.g., phospholipids). For example, the shell may include less than about 500, less than about 400, less than about 300, less than about 200, or less than about 100 natural or synthetic lipids or lipid analogs (e.g., phospholipids), e.g., depending on the size of the structure.

Non-phosphorus containing lipids may also be used such as stearylamine, docecylamine, acetyl palmitate, and fatty acid amides. In other embodiments, other lipids such as fats, oils, waxes, cholesterol, sterols, fat-soluble vitamins (e.g., vitamins A, D, E and K), glycerides (e.g., monoglycerides, diglycerides, triglycerides) can be used to form portions of a structure described herein.

A portion of a structure described herein such as a shell or a surface of a nanostructure may optionally include one or more alkyl groups, e.g., an alkane-, alkene-, or alkyne-containing species, that optionally imparts hydrophobicity to the structure. An "alkyl" group refers to a saturated aliphatic group, including a straight-chain alkyl group, branched-chain alkyl group, cycloalkyl (alicyclic) group, alkyl substituted cycloalkyl group, and cycloalkyl substituted alkyl group. The alkyl group may have various carbon numbers, e.g., between $C_2$ and $C_{40}$, and in some embodiments may be greater than $C_5$, $C_{10}$, $C_{15}$, $C_{20}$, $C_{25}$, $C_{30}$, or $C_{35}$. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The alkyl group may include any suitable end group, e.g., a thiol group, an amino group (e.g., an unsubstituted or substituted amine), an amide group, an imine group, a carboxyl group, or a sulfate group, which may, for example, allow attachment of a ligand to a nanostructure core directly or via a linker. For example, where inert metals are used to form a nanostructure core, the alkyl species may include a thiol group to form a metal-thiol bond. In some instances, the alkyl species includes at least a second end group. For example, the species may be bound to a hydrophilic moiety such as polyethylene glycol. In other embodiments, the second end group may be a reactive group that can covalently attach to another functional group. In some instances, the second end group can participate in a ligand/receptor interaction (e.g., biotin/streptavidin).

Where a shell includes an amphiphilic material, the material can be arranged in any suitable manner with respect to the nanostructure core and/or with each other. For instance, the amphiphilic material may include a hydrophilic group that points towards the core and a hydrophobic group that extends away from the core, or, the amphiphilic material may include a hydrophobic group that points towards the core and a hydrophilic group that extends away from the core. Bilayers of each configuration can also be formed.

The lipid bilayer is composed of two layers of lipid molecules. Each lipid molecule in a layer is oriented substantially parallel to adjacent lipid bilayers, and two layers that form a bilayer have the polar ends of their molecules exposed to the aqueous phase and the non-polar ends adjacent to each other.

"Lipid" refers to its conventional sense as a generic term encompassing fats, lipids, alcohol-ether-soluble constituents of protoplasm, which are insoluble in water. Lipids usually consist of a hydrophilic and a hydrophobic moiety. In water, lipids can self-organize to form bilayers membranes, where the hydrophilic moieties (head groups) are oriented towards the aqueous phase, and the lipophilic moieties (acyl chains) are embedded in the bilayers core. Lipids can comprise as well two hydrophilic moieties (bolaamphiphiles). In that case, membranes may be formed from a single lipid layer, and not a bilayer. Typical examples for lipids in the current context are fats, fatty oils, essential oils, waxes, steroid, sterols, phospholipids, glycolipids, sulpholipids, aminolipids, chromolipids, and fatty acids. The term encompasses both naturally occurring and synthetic lipids. Preferred lipids in connection with the present invention are: steroids and sterol, particularly cholesterol, phospholipids, including phosphatidyl, phosphatidylcholines and phosphatidylethanolamines and sphingomyelins. Where there are fatty acids, they could be about 12-24 carbon chains in length, containing up to 6 double bonds. The fatty acids are linked to the backbone, which may be derived from glycerol. The fatty acids within one lipid can be different (asymmetric), or there may be only 1 fatty acid chain present, e.g. lysolecithins. Mixed formulations are also possible, particularly when the non-cationic lipids are derived from natural sources, such as lecithins (phosphatidylcholines) purified from egg yolk, bovine heart, brain, liver or soybean.

The nanostructures described herein may also include one or more proteins, polypeptides and/or peptides (e.g., synthetic peptides, amphiphilic peptides). In one set of embodiments, the structures include proteins, polypeptides and/or peptides that can increase the rate of cholesterol transfer or the cholesterol-carrying capacity of the structures. The one or more proteins or peptides may be associated with the core (e.g., a surface of the core or embedded in the core), the shell (e.g., an inner and/or outer surface of the shell, and/or embedded in the shell), or both. Associations may include covalent or non-covalent interactions (e.g., hydrophobic and/or hydrophilic interactions, electrostatic interactions, van der Waals interactions).

The nanostructure is composed of a core, which may be an inorganic material, surrounded by a shell of a lipid layer. The nanostructure also includes a protein, such as an apolipoprotein. The apolipoprotein can be apolipoprotein A (e.g., apo A-I, apo A-II, apo A-IV, and apo A-V), apolipoprotein B (e.g., apo B48 and apo B100), apolipoprotein C (e.g., apo C-I, apo C-II, apo C-III, and apo C-IV), and apolipoproteins D, E, and H. Specifically, apo A1, apo A2, and apo E promote transfer of cholesterol and cholesteryl esters to the liver for metabolism and may be useful to include in structures described herein. Additionally or alternatively, a structure described herein may include one or more peptide analogues of an apolipoprotein, such as one described above. Of course, other proteins (e.g., non-apolipoproteins) can also be included in the nanostructures described herein.

It should be understood that the components described herein, such as the lipids, phospholipids, alkyl groups, polymers, proteins, polypeptides, peptides, enzymes, bioactive agents, nucleic acids, and species for targeting described above (which may be optional), may be associated with a nanostructure in any suitable manner and with any suitable portion of the nanostructure, e.g., the core, the shell, or both. For example, one or more such components may be associated with a surface of a core, an interior of a core, an inner surface of a shell, an outer surface of a shell, and/or embedded in a shell.

A variety of methods can be used to fabricate the nanostructures described herein. Examples of methods are provided in International Patent Publication No. WO/2009/131704, filed Apr. 24, 2009 and entitled, "Nanostructures Suitable for Sequestering Cholesterol and Other Molecules", which is incorporated herein by reference in its entirety for all purposes.

The shell may have an inner surface (facing the core) and an outer surface (facing the surroundings), such that the apolipoprotein may be adsorbed on the outer shell and/or incorporated between the inner surface and outer surface of the shell. The shell is comprised of lipids and may be a lipid monolayer or bilayer, for instance.

It should be understood that a shell which surrounds a core need not completely surround the core, although such embodiments may be possible. For example, the shell may surround at least 50%, at least 60%, at least 70%, at least 80%, at least 90%, or at least 99% of the surface area of a core. In some cases, the shell substantially surrounds a core. In other cases, the shell completely (100%) surrounds a core. The components of the shell may be distributed evenly across a surface of the core in some cases, and unevenly in other cases. For example, the shell may include portions (e.g., holes) that do not include any material in some cases. If desired, the shell may be designed to allow penetration and/or transport of certain molecules and components into or out of the shell, but may prevent penetration and/or transport of other molecules and components into or out of the shell. The ability of certain molecules to penetrate and/or be transported into and/or across a shell may depend on, for example, the packing density of the components forming the shell and the chemical and physical properties of the components forming the shell. The shell may include one layer of material, or multilayers of materials in some embodiments.

In some embodiments, the nanostructure includes a cationic lipid. The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d] [1,3] dioxol-5-amine, (6Z,9Z,28Z,31Z)-heptatriaconta-6,9,28,31-tetraen-19-yl-4-(dimethylamino) butanoate, or a mixture thereof.

Other cationic lipids, which carry a net positive charge at about physiological pH, in addition to those specifically described above, may also be included in the lipid nanoparticle. Such cationic lipids include, but are not limited to, N,N-dioleyl-N,N-dimethylammonium chloride ("DODAC"); N-(2,3-dioleyloxy)propyl-N,N-N-triethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 1,2-Dioleyloxy-3-trimethylaminopropane chloride salt ("DOTAP.Cl"); 3.beta.-(N-(N',N'-dimethylaminoethane)-carbamoyl)cholesterol ("DC-Chol"), N-(1-(2,3-dioleyloxy) propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), N-(1,2-dimyristyloxyprop-3-yl)-N,N-dimethyl-N-hydroxyethyl ammonium bromide ("DMRIE"), and 1,2-dioleoyl-sn-glycero-3-phosphocholine ("DOPC").

In some aspects of the disclosure, the nanostructure comprises a cationic lipid (e.g., DOTAP) is mixed with a nucleic acid (e.g., RNA) in a molar ratio of about 1:1, of about 2:1, of about 3:1, of about 4:1, of about 5:1, of about 6:1, of about 7:1, of about 8:1, of about 9:1, of about 10:1, of about 11:1, of about 12:1, of about 13:1, of about 14:1, of about 15:1, of about 16:1, of about 17:1, of about 18:1, of about 19:1, of about 20:1, of about 21:1, of about 22:1, of about 23:1, of about 24:1, of about 25:1, of about 26:1, of about 27:1, of about 28:1, of about 29:1, of about 30:1, of about 31:1, of about 32:1, of about 33:1, of about 34:1, of about 35:1, of about 36:1, of about 37:1, of about 38:1, of about 39:1, of about 40:1, of about 41:1, of about 42:1, of about 43:1, of about 44:1, of about 45:1, of about 46:1, of about 47:1, of about 48:1, of about 49:1, of about 50:1, of about 60:1, of about 70:1, of about 80:1, of about 90:1, or of about 100:1. In some embodiments, the cationic lipid (e.g. DOTAP) is mixed with the nucleic acid (e.g., RNA) in a molar ratio of 10:1, 20:1, 30:1 or 40:1.

"Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleylphosphatidylcholine, monophosphoryl lipid A (MPLA), or glycopyranoside lipid A (GLA).

In some aspects, the nucleic acid or oligonucleotide regulate the expression of a gene. As used herein, "regulating gene expression" or "gene regulation" are used interchangeably and includes a wide range of mechanisms that are used by cells to increase or decrease the production of specific gene products (e.g., protein, RNA, etc.).

In some embodiments the nucleic acid or oligonucleotide is an inhibitory nucleic acid. The inhibitory nucleic acid may be, for instance, an siRNA or an antisense molecule that inhibits expression of a protein that will have a therapeutic effect. The inhibitory nucleic acids may be designed using routine methods in the art.

An inhibitory nucleic acid typically causes specific gene knockdown, while avoiding off-target effects. Various strategies for gene knockdown known in the art can be used to inhibit gene expression. For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, and other small interfering nucleic acid-based molecules known in the art. In one embodiment, vector-based RNAi modalities (e.g., shRNA expression constructs) are used to reduce expression of a gene in a cell. In some embodiments, therapeutic compositions of the invention comprise an isolated plasmid vector (e.g., any isolated plasmid vector known in the art or disclosed herein) that expresses a small interfering nucleic acid such as an shRNA. The isolated plasmid may comprise a specific promoter operably linked to a gene encoding the small interfering nucleic acid. In some cases, the isolated plasmid vector is packaged in a virus capable of infecting the individual. Exemplary viruses include adenovirus, retrovirus, lentivirus, adeno-associated virus, and others that are known in the art and disclosed herein.

A broad range of RNAi-based modalities could be employed to inhibit expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to nucleic acids or oligonucleotides to increase resistance to nuclease degradation, binding affinity and/or uptake. In addition, hydrophobization and bioconjugation enhances siRNA delivery and targeting (De Paula et al., RNA. 13(4): 431-56, 2007) and siRNAs with ribo-difluorotoluyl nucleotides maintain gene silencing activity (Xia et al., ASC Chem. Biol. 1(3):176-83, (2006)). siRNAs with amide-linked oligoribonucleosides have been generated that are more resistant to S1 nuclease degradation than unmodified siRNAs (Iwase R et al. 2006 Nucleic Acids Symp Ser 50: 175-176). In addition, modification of siRNAs at the 2'-sugar position and phosphodiester linkage confers improved serum stability without loss of efficacy (Choung et al., Biochem. Biophys. Res. Commun. 342(3):919-26, 2006).

Other molecules that can be used to inhibit expression of a gene include antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat Med. 4(8):967-71, 1998). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996).

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4): 307-17, 1991; Knudsen and Nielson Nucleic Acids Res. 24(3):494-500, 1996; Taylor et al., Arch. Surg. 132(11): 1177-83, 1997). Minor-groove binding polyamides can bind in a sequence-specific manner to DNA targets and hence may represent useful small molecules for suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). The diverse array of suppression strategies that can be employed includes the use of DNA and/or RNA aptamers that can be selected to target a protein of interest.

Other inhibitor molecules that can be used include antisense nucleic acids (single or double stranded). Antisense nucleic acids include modified or unmodified RNA, DNA, or mixed polymer nucleic acids, and primarily function by specifically binding to matching sequences resulting in modulation of peptide synthesis (Wu-Pong, November 1994, BioPharm, 20-33). Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, Crit. Rev. in Oncogenesis 7, 151-190).

As used herein, the term "antisense nucleic acid" describes a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

An inhibitory nucleic acid useful in the invention will generally be designed to have partial or complete complementarity with one or more target genes. The target gene may be a gene derived from the cell, an endogenous gene, a transgene, or a gene of a pathogen which is present in the cell after infection thereof. Depending on the particular target gene, the nature of the inhibitory nucleic acid and the level of expression of inhibitory nucleic acid (e.g. depending on copy number, promoter strength) the procedure may provide partial or complete loss of function for the target gene. Quantitation of gene expression in a cell may show similar amounts of inhibition at the level of accumulation of target mRNA or translation of target protein.

"Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. As an example, the efficiency of inhibition may be determined by assessing the amount of gene product in the cell: mRNA may be detected with a hybridization probe having a nucleotide sequence outside the region used for the inhibitory nucleic acid, or translated polypeptide may be detected with an antibody raised against the polypeptide sequence of that region.

An expression enhancing nucleic acid or oligonucleotide as used herein is a synthetic oligonucleotide that encodes a protein. The synthetic oligonucleotide may be delivered to a cell such that it is used by a cells machinery to produce a protein based on the sequence of the synthetic oligonucleotide. The synthetic oligonucleotide may be, for instance, synthetic DNA or synthetic RNA. "Synthetic RNA" refers to a RNA produced through an in vitro transcription reaction or through artificial (non-natural) chemical synthesis. In some embodiments, a synthetic RNA is an RNA transcript. In some embodiments, a synthetic RNA encodes a protein. In some embodiments, the synthetic RNA is a functional RNA. In some embodiments, a synthetic RNA comprises one or more modified nucleotides. In some embodiments, a synthetic RNA is up to 0.5 kilobases (kb), 1 kb, 1.5 kb, 2 kb, 2.5 kb, 3 kb, 4 kb, 5 kb, 6 kb, 7 kb, 8 kb, 9 kb, 10 kb, 15 kb, 20 kb, 25 kb, 30 kb or more in length. In some embodiments, a synthetic RNA is in a range of 0.1 kb to 1 kb, 0.5 kb to 2 kb, 0.5 kb to 10 kb, 1 kb to 5 kb, 2 kb to 5 kb, 1 kb to 10 kb, 3 kb to 10 kb, 5 kb to 15 kb, or 1 kb to 30 kb in length.

A diagnostic nucleic acid or oligonucleotide is an nucleic acid or oligonucleotide that interacts with a cellular marker to identify the presence of the marker in a cell or subject. Diagnostic oligonucleotides are well known in the art and typically include a label or are otherwise detectable.

The terms "oligonucleotide" and "nucleic acid" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymidine (T) or uracil (U)) or a substituted purine (e.g., adenine (A) or guanine (G)). Thus, the term embraces both DNA and RNA oligonucleotides. The terms shall also include polynucleosides (i.e., a polynucleotide minus the phosphate) and any other organic base containing polymer. Oligonucleotides can be obtained from existing nucleic acid sources (e.g., genomic or cDNA), but are preferably synthetic (e.g., produced by nucleic acid synthesis).

An oligonucleotide of the nanostructure can be single stranded or double stranded. A double stranded oligonucleotide is also referred to herein as a duplex. Double-stranded oligonucleotides of the invention can comprise two separate complementary nucleic acid strands.

The nucleic acids useful in the nanostructures of the invention are synthetic or isolated nucleic acids.

As used herein, "duplex" includes a double-stranded nucleic acid molecule(s) in which complementary sequences are hydrogen bonded to each other. The complementary sequences can include a sense strand and an antisense strand. The antisense nucleotide sequence can be identical or sufficiently identical to the target gene to mediate effective target gene inhibition (e.g., at least about 98% identical, 96% identical, 94%, 90% identical, 85% identical, or 80% identical) to the target gene sequence.

A double-stranded nucleic acid or oligonucleotide can be double-stranded over its entire length, meaning it has no overhanging single-stranded sequences and is thus blunt-ended. In other embodiments, the two strands of the double-stranded polynucleotide can have different lengths producing one or more single-stranded overhangs. A double-stranded polynucleotide of the invention can contain mismatches and/or loops or bulges. In some embodiments, it is double-stranded over at least about 70%, 80%, 90%, 95%, 96%, 97%, 98% or 99% of the length of the oligonucleotide. In some embodiments, the double-stranded oligonucleotide of the invention contains at least or up to 1, 2, 3, 4, 5, 6, 7, 8, 9, 10, 11, 12, 13, 14, or 15 mismatches.

Nucleic acids or oligonucleotides associated with the invention can be modified such as at the sugar moiety, the phosphodiester linkage, and/or the base. As used herein, "sugar moieties" includes natural, unmodified sugars, including pentose, ribose and deoxyribose, modified sugars and sugar analogs. Modifications of sugar moieties can include replacement of a hydroxyl group with a halogen, a heteroatom, or an aliphatic group, and can include functionalization of the hydroxyl group as, for example, an ether, amine or thiol.

Modification of sugar moieties can include 2'-O-methyl nucleotides, which are referred to as "methylated." In some instances, polynucleotides associated with the invention may only contain modified or unmodified sugar moieties, while in other instances, polynucleotides contain some sugar moieties that are modified and some that are not.

In some instances, modified nucleomonomers include sugar- or backbone-modified ribonucleotides. Modified ribonucleotides can contain a non-naturally occurring base such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides can have the 2'—OH group replaced by an H, alkoxy (or OR), R or alkyl, halogen, SH, SR, amino (such as NH2, NHR, NR2), or CN group, wherein R is lower alkyl, alkenyl, or alkynyl. In some embodiments, modified ribonucleotides can have the phosphodiester group connecting to adjacent ribonucleotides replaced by a modified group, such as a phosphorothioate group.

In some aspects, 2'-O-methyl modifications can be beneficial for reducing undesirable cellular stress responses, such as the interferon response to double-stranded nucleic acids. Modified sugars can include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—OCH$_2$CH=CH$_2$), 2'-propargyl, 2'-propyl, ethynyl, ethenyl, propenyl, and cyano and the like. The sugar moiety can also be a hexose.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-N$_6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In some aspects, polynucleotides of the invention comprise 3' and 5' termini (except for circular oligonucleotides). The 3' and 5' termini of a polynucleotide can be substantially protected from nucleases, for example, by modifying the 3' or 5' linkages (e.g., U.S. Pat. No. 5,849,902 and WO 98/13526). Oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl (CH$_2$—CH$_2$—CH$_3$), glycol (—O—CH$_2$—CH$_2$—O—) phosphate (PO32-), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. Antisense Res. Dev. 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3'linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", 2nd Ed., Wiley-Interscience, New York, 1999).

As used herein, the nanostructure is a construct having an average diameter on the order of nanometers (i.e., between about 1 nm and about 1 micrometer. For example, in some instances, the diameter of the nanoparticle is from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 ran in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, about 1 nm to about 20 nm in mean diameter, about 1 nm to about 10 nm in mean diameter, about 5 nm to about 150 nm in mean diameter, about 5 to about 50 nm in mean diameter, about 10 to about 30 nm in mean diameter, about 10 to 150 nm in mean diameter, about 10 to about 100 nm in mean diameter, about 10 to about 50 nm in mean diameter, about 30 to about 100 nm in mean diameter, or about 40 to about 80 nm in mean diameter. In a set of embodiments, the nanostructure is about 110 nm in diameter.

In some embodiments, the nanostructures may be used at a concentration of about 1 nM to about 1000 nM, of about 1 nM to about 900 nM, of about 1 nM to about 800 nM, of about 1 nM to about 700 nM, of about 1 nM to about 600 nM, of about 1 nM to about 500 nM, of about 1 nM to about 400 nM, of about 1 nM to about 300 nM, of about 1 nM to about 200 nM, of about 1 nM to about 100 nM, of about 1 nM to about 50 nM, of about 1 nM to about 40 nM, of about 1 nM to about 30 nM, of about 1 nM to about 20 nM, or of about 1 nM to about 10 nM. In a set of embodiments, the nanostructure is used at a concentration of 5 nM, 10 nM or 20 nM.

In some aspects of the disclosure, the nanostructure comprises a nucleic acid (e.g., RNA) mixed with TLP in a molar ratio of about 1:1, of about 2:1, of about 3:1, of about 4:1, of about 5:1, of about 6:1, of about 7:1, of about 8:1, of about 9:1, of about 10:1, of about 11:1, of about 12:1, of about 13:1, of about 14:1, of about 15:1, of about 16:1, of about 17:1, of about 18:1, of about 19:1, of about 20:1, of about 21:1, of about 22:1, of about 23:1, of about 24:1, of about 25:1, of about 26:1, of about 27:1, of about 28:1, of about 29:1, of about 30:1, of about 31:1, of about 32:1, of about 33:1, of about 34:1, of about 35:1, of about 36:1, of about 37:1, of about 38:1, of about 39:1, of about 40:1, of about 41:1, of about 42:1, of about 43:1, of about 44:1, of about 45:1, of about 46:1, of about 47:1, of about 48:1, of about 49:1, of about 50:1, of about 60:1, of about 70:1, of about 80:1, of about 90:1, or of about 100:1. In some embodiments the nucleic acid, such as RNA, is mixed with TLP in a molar ratio of 5:1, 15:1 or 25:1. In a set of embodiments, the nanostructure comprises a nucleic acid (e.g., RNA) mixed with TLP at a molar ratio of 25:1 and a cationic lipid (e.g., DOTAP) mixed with a nucleic acid (e.g., RNA) in a molar ratio of 40:1.

The nanostructures may be used in "pharmaceutical compositions" or "pharmaceutically acceptable" compositions, which comprise a therapeutically effective amount of one or more of the structures described herein, formulated together with one or more pharmaceutically acceptable carriers, additives, and/or diluents. The pharmaceutical compositions described herein may be useful for treating cancer or autoimmune diseases or disorders, or other related diseases. It should be understood that any suitable structures described herein can be used in such pharmaceutical compositions, including those described in connection with the figures.

The pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The structures described herein may be orally administered, parenterally administered, subcutaneously administered, and/or intravenously administered. In certain embodiments, a structure or pharmaceutical preparation is administered orally. In other embodiments, the structure or pharmaceutical preparation is administered intravenously. Alternative routes of administration include sublingual, intramuscular, and transdermal administrations.

Pharmaceutical compositions described herein include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

The inventive compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a structure described herein as an active ingredient. The HDL-NP may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered structure is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the structures described herein include pharmaceutically acceptable emulsions, microemulsions, solutions, dispersions, suspensions, syrups and elixirs. In addition to the inventive structures, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions described herein (e.g., for rectal or vaginal administration) may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the body and release the structures.

Dosage forms for the topical or transdermal administration of a structure described herein include powders, sprays, ointments, pastes, foams, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to the inventive structures, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the structures described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a structure described herein to the body. Dissolving or dispersing the structure in the proper medium can make such dosage forms. Absorption enhancers can also be used to increase the flux of the structure across the skin. Either providing a rate controlling membrane or dispersing the structure in a polymer matrix or gel can control the rate of such flux.

Ophthalmic formulations, eye ointments, powders, solutions and the like, are also contemplated as being within the scope of this invention.

Pharmaceutical compositions described herein suitable for parenteral administration comprise one or more inventive structures in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with structures and compositions described herein include time-release, delayed release, sustained release, or controlled release delivery systems, as described herein. Such systems may avoid repeated administrations of the structures in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The compositions may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiments. The structures and compositions described herein can also be combined (e.g., contained) with delivery devices such as syringes, pads, patches, tubes, films, MEMS-based devices, and implantable devices.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

Injectable depot forms can be made by forming microencapsule matrices of the structures described herein in biodegradable polymers such as polylactide-polyglycolide. Depending on the ratio of structure to polymer, and the nature of the particular polymer employed, the rate of release of the structure can be controlled. Examples of other biodegradable polymers include poly(orthoesters) and poly(anhydrides).

When the structures described herein are administered as pharmaceuticals, to humans and animals, they can be given per se or as a pharmaceutical composition containing, for example, about 0.1% to about 99.5%, about 0.5% to about 90%, or the like, of structures in combination with a pharmaceutically acceptable carrier.

The administration may be localized (e.g., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the structures described herein, which may be used in a suitable hydrated form, and/or the inventive pharmaceutical compositions, are formulated into pharmaceutically-acceptable dosage forms by conventional methods known to those of skill in the art.

The compositions described herein may be given in dosages, e.g., at the maximum amount while avoiding or minimizing any potentially detrimental side effects. The compositions can be administered in effective amounts, alone or in a combinations with other compounds. For example, when treating cancer, a composition may include the structures described herein and a cocktail of other compounds that can be used to treat cancer. When treating conditions associated with abnormal lipid levels, a composition may include the structures described herein and other compounds that can be used to reduce lipid levels (e.g., cholesterol lowering agents).

The phrase "therapeutically effective amount" as used herein means that amount of a material or composition comprising an inventive structure which is effective for producing some desired therapeutic effect in a subject at a reasonable benefit/risk ratio applicable to any medical treatment. Accordingly, a therapeutically effective amount may, for example, prevent, minimize, or reverse disease progression associated with cancer or an autoimmune disorder. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more structures described herein may be from about 10 ng/kg of body weight to about 1000 mg/kg of body weight, and the frequency of administration may range from once a day to once a month. However, other dosage amounts and frequencies also may be used as the invention is not limited in this respect. A subject may be administered one or more structure described herein in an amount effective to treat one or more diseases or bodily conditions described herein.

An effective amount may depend on the particular condition to be treated. The effective amounts will depend, of course, on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular inventive structure employed, the route of administration, the time of administration, the rate of excretion or metabolism of the particular structure being employed, the duration of the treatment, other drugs, compounds and/or materials used in combination with the particular structure employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the structures described herein employed in the pharmaceutical composition at levels lower than that required to achieve the desired therapeutic effect and then gradually increasing the dosage until the desired effect is achieved.

In some embodiments, a structure or pharmaceutical composition described herein is provided to a subject chronically. Chronic treatments include any form of repeated administration for an extended period of time, such as repeated administrations for one or more months, between a month and a year, one or more years, or longer. In many embodiments, a chronic treatment involves administering a structure or pharmaceutical composition repeatedly over the life of the subject. For example, chronic treatments may involve regular administrations, for example one or more times a day, one or more times a week, or one or more times a month. In general, a suitable dose such as a daily dose of a structure described herein will be that amount of the structure that is the lowest dose effective to produce a therapeutic effect. Such an effective dose will generally depend upon the factors described above. Generally doses of the structures described herein for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. In some embodiments, the nanostructure is administered at a dose of about 1000 mg/kg, of about 500 mg/kg, of about 100 mg/kg, of about 50 mg/kg, of about 25 mg/kg, of about 10 mg/kg, of about 5 mg/kg, of about 4 mg/kg, of about 3 mg/kg, of about 2 mg/kg, of about 1 mg/kg, of about 0.7 mg/kg, of about 0.5 mg/kg, 0.1 mg/kg. In certain embodiments, the nanostructure is administered at a dose of 0.7 mg/kg. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms. For example, instructions and methods may include dosing regimens wherein specific doses of compositions, especially those including structures described herein having a particular size range, are administered at specific time intervals and specific doses to achieve reduction of cholesterol (or other lipids) and/or treatment of disease while reducing or avoiding adverse effects or unwanted effects.

While it is possible for a structure described herein to be administered alone, it may be administered as a pharmaceutical composition as described above. The present invention also provides any of the above-mentioned compositions useful for diagnosing, preventing, treating, or managing a disease or bodily condition packaged in kits, optionally including instructions for use of the composition. That is, the kit can include a description of use of the composition for participation in any disease or bodily condition, including those associated with abnormal lipid levels. The kits can further include a description of use of the compositions as discussed herein. The kit also can include instructions for use of a combination of two or more compositions described herein. Instructions also may be provided for administering the composition by any suitable technique, such as orally, intravenously, or via another known route of drug delivery.

The kits described herein may also contain one or more containers, which can contain components such as the structures, signaling entities, and/or biomolecules as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are used, the liquid form may be concentrated or ready to use. The solvent will depend on the particular inventive structure and the mode of use or administration. Suitable solvents for compositions are well known and are available in the literature.

The kit, in one set of embodiments, may comprise one or more containers such as vials, tubes, and the like, each of the containers comprising one of the separate elements to be used in the method. For example, one of the containers may comprise a positive control in the assay. Additionally, the kit may include containers for other components, for example, buffers useful in the assay.

As used herein, a "subject" or a "patient" refers to any mammal (e.g., a human), for example, a mammal that may be susceptible to a disease or bodily condition such as a disease or bodily condition associated with abnormal gene expression. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A subject may be a subject diagnosed with a certain disease or bodily condition or otherwise known to have a disease or bodily condition such as cancer or an autoimmune disorder. In some embodiments, a subject may be diagnosed as, or known to be, at risk of developing a disease or bodily condition.

In some embodiments, the nanostructure may be administered to a subject systemically. Systemic routes of administration, include but are not limited to, enteral or parenteral routes. Examples of enteral routes of administration include oral, sublingual or rectal administration. Parenteral routes of administration include inhalational, transdermal, or injections, such as intravenous, intramuscular, subcutaneous, intra-arterial, intra-articular, intra-thecal injections.

In some embodiments, a subject may be diagnosed with, or otherwise known to have, a disease or bodily condition associated with cancer or an autoimmune disorder.

A subject having a cancer is a subject that has detectable cancerous cells. The cancer may be a malignant or non-malignant cancer. Cancers or tumors include, but are not limited to, biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment, the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma. In another embodiment, the cancer is prostate cancer, breast cancer, renal cancer or ovarian cancer.

The nanostructures are also useful for treating and preventing autoimmune disease or disorder in a subject. Autoimmune disease or disorder is a class of diseases in which an subject's own antibodies react with host tissue or in which immune effector T cells are autoreactive to endogenous self peptides and cause destruction of tissue. Thus, an immune response is mounted against a subject's own antigens, referred to as self antigens. Autoimmune diseases or disorders include, but are not limited to, rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

Major groups of vaccine adjuvants include, but are not limited to, mineral salt adjuvants, such as alum, calcium, iron and zirconium-based adjuvants; tensoactive adjuvants; bacteria derived adjuvants; adjuvant emulsions; liposome adjuvants; polymeric microsphere adjuvants; cytokines; carbohydrate adjuvants, such as inulin-derived adjuvants, polysaccharides based on glucose and mannose with adjuvant action, such as glucans, dextrans, lentinans, glucomannans, levans, xylans; adjuvant formulations; mucosal adjuvants, such as bacterial derivatives, synthetic or inactivate antigen delivery systems, living antigen mucosal delivery systems; adjuvants for DNA immunization; or DNA vaccines and particulate adjuvant systems. (See e.g., Petrovsky et al., Immunol Cell Biol (2004) 82, 488-496).

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, Cancer Research, 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

The function and advantage of these and other embodiments will be more fully understood from the examples below. The following examples are intended to illustrate the benefits of the present invention, but do not exemplify the full scope of the invention. Accordingly, it will be understood that the example section is not meant to limit the scope of the invention.

Examples

Example 1: Self-Assembly of Single-Strand Complements of siRNA, Lipids, and Bio-Inspired Nanoparticles Yields Anionic Vehicles for Active siRNA Delivery There is significant interest in developing synthetic mimics of natural RNA delivery vehicles.[8] In particular, high-density lipoproteins (HDL) are appealing because they naturally bind endogenous RNAs, like microRNA, stabilize the single-stranded RNA (ssRNA) to nuclease degradation, and deliver them to target cells to regulate gene expression.[12,13] HDL-mediated delivery of RNA is dependent upon target cell expression of scavenger receptor type B-1 (SR-B1), the high-affinity receptor for mature spherical HDLs, such as the mature HDLs that have apolipoprotein A-I (apoA-I) on their surface.[12,14,15] In addition to HDL, SR-B1 binds anionic particulate ligands in a wide variety of sizes.[16-18] HDLs appear to overcome hurdles to successful systemic delivery of RNA to target cells that express SR-B1. These data have motivated the development of synthetic mimics of HDLs that efficiently load, stabilize, and deliver therapeutic RNAs, like siRNA.[19-23]

In the present example, the Applicant focused on the following properties of natural HDL that appear to enable targeted systemic delivery of RNA, including: 1) the ability to bind and stabilize single-stranded RNA in a scalable and modular fashion, 2) charge reconciliation between HDL and RNA that enables nucleic acid binding and efficient RNA delivery, and 3) active targeting of SR-B1 for RNA delivery.[12] According to these design elements, the Applicant synthesized templated lipoprotein particles (TLP) that initiate a self-assembly process that incorporates and stabilizes ssRNA complements of siRNA duplexes after complexation with a cationic lipid. The use of a cationic lipid reconciles the negative charge of ssRNAs and TLPs enabling efficient and tunable siRNA-TLP self-assembly and function. The particles actively target SR-B1 to potently regulate target gene expression in multiple cancer cell lines in vitro and in an in vivo xenograft model without inherent toxicity. Finally, with an eye toward translation to human patients, siRNA-TLPs are modular such that specific siRNAs targeting different disease-relevant proteins can be formulated with pre-fabricated TLPs demonstrating the potential to manufacture, scale-up, and provide on-demand patient-specific siRNA therapy.

Results

Templated Lipoprotein Nanoparticles (TLP) Synthesis

Natural HDL is an anionic delivery vehicle for unmodified nucleic acids.[12] As such, one goal of this work was to fundamentally understand and develop synthetic particles that incorporate highly unmodified single-stranded complements of a desired siRNA duplex. The Applicant started by generating a lipoprotein inspired particle by surface-functionalizing a 5 nm diameter gold nanoparticle (Au NP) template with apolipoprotein A-I (apoA-I), the defining HDL protein,[24] a mixture of two phospholipids, and cholesterol (FIG. 1A). The phospholipid containing a di-sulfide headgroup binds to the Au NP providing a hydrophobic surface for the assembly of the outer phospholipid and cholesterol.[25-27] The outer phospholipid and cholesterol were chosen because they favorably associate with nucleic acids and have been shown to enhance nucleic acid delivery.[28] Characterization of the TLPs reveals similar shape (spherical), size (13±2 nm), and anionic charge (−42±1 mV), comparable to natural HDL.[27] Large batches of TLPs were synthesized, purified, and stored for several months at 4° C., providing a platform for investigating modular addition of RNA.

Figure 1B:
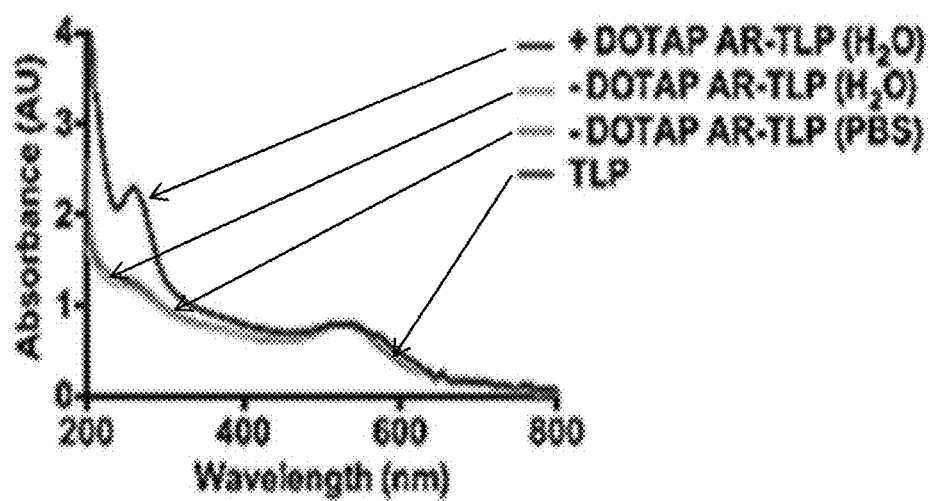

DOTAP Provides Charge Reconciliation and Enables Optimal Self-Assembly of Single-Stranded RNA to Form siRNA-TLPs Next, conditions supporting the self-assembly of RNA with TLPs were identified. As an initial proof-of-concept, siRNA sequences were designed to target the androgen receptor (AR), a well-established target for prostate cancer (Table 1).[29] The AR, and the AR signaling axis, are well-known targets in patients suffering from advanced prostate cancer even after treatment failure due to castration, which is the gold standard therapy for systemic disease.[49] Due to the negative charge of TLPs and RNA, 1,2-dioleoyl-3-trimethylammonium-propane (DOTAP), a cationic lipid known to complex RNA through electrostatic (head group-RNA phosphate) and hydrophobic (lipid tail-RNA nucleobase) interactions,[30] was added to mixtures of RNA in water or 1× phosphate buffered saline (PBS). A DOTAP: RNA molar ratio of 40:1 provided approximately one DOTAP molecule per phosphate of the ssRNA sequences (charge ratio ~1:1). RNA alone or DOTAP-RNA mixtures were added to TLPs. After overnight incubation, TLPs mixed with DOTAP-RNA in PBS were irreversibly aggregated and precipitated. Purified solutions of the remaining particles were subjected to ultraviolet-visible (UV-Vis) spectroscopy, which revealed a strong absorption band at ~520 nm, characteristic of disperse 5 nm diameter Au NPs.[31] However, only TLPs mixed with DOTAP-RNA in water demonstrated the presence of RNA by UV-Vis spectroscopy as indicated by a strong absorption at ~260 nm (FIG. 1B). These data suggest that charge reconciliation by DOTAP is required for the self-assembly of RNA with TLPs. In addition, because self-assembly only occurred in water, these data suggest that RNA bound to TLPs are single-stranded.

Figure 7A:
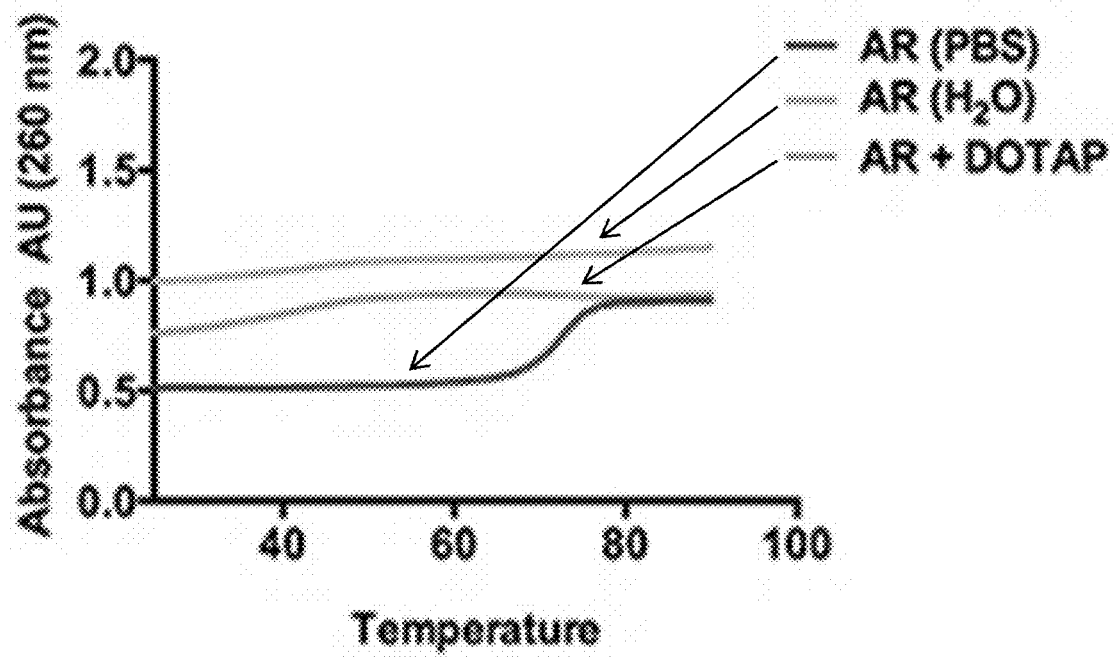
FIGS. 7A-7F show RNA melting analysis, ζ-potential measurement, and function of siRNA-TLP.

To directly test if RNA bound to TLPs were single strands or if DOTAP facilitated siRNA duplex formation in water, thermal denaturation experiments were performed. RNA melting transitions were measured in water and in PBS and compared to the DOTAP-RNA mixture. A clear melting transition was observed for the siRNA duplex in PBS. No melting transition was observed for the RNA sequences in water, which was similar to the data collected for the DOTAP-RNA mixture (FIG. 7A). Thus, data demonstrate that DOTAP facilitates the assembly of ssRNA with TLPs.

Figure 1C:
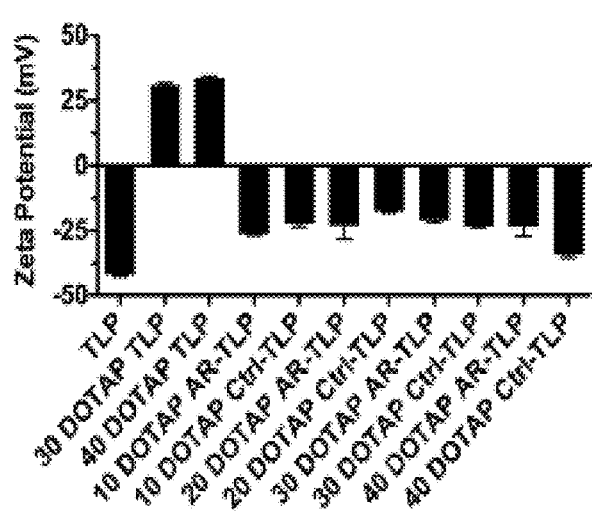
Figure 1D:
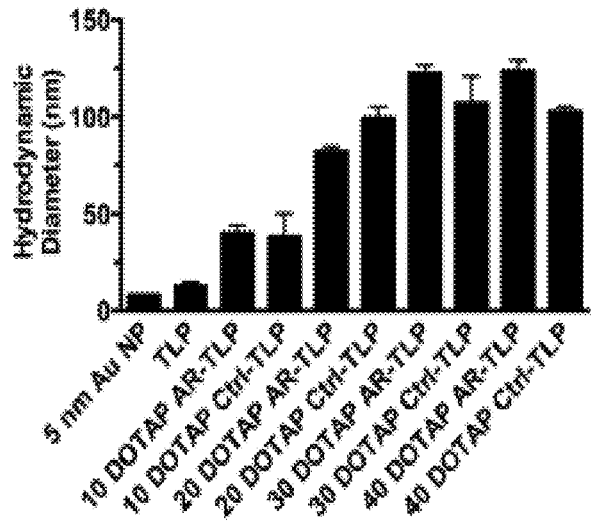
Figure 7B:
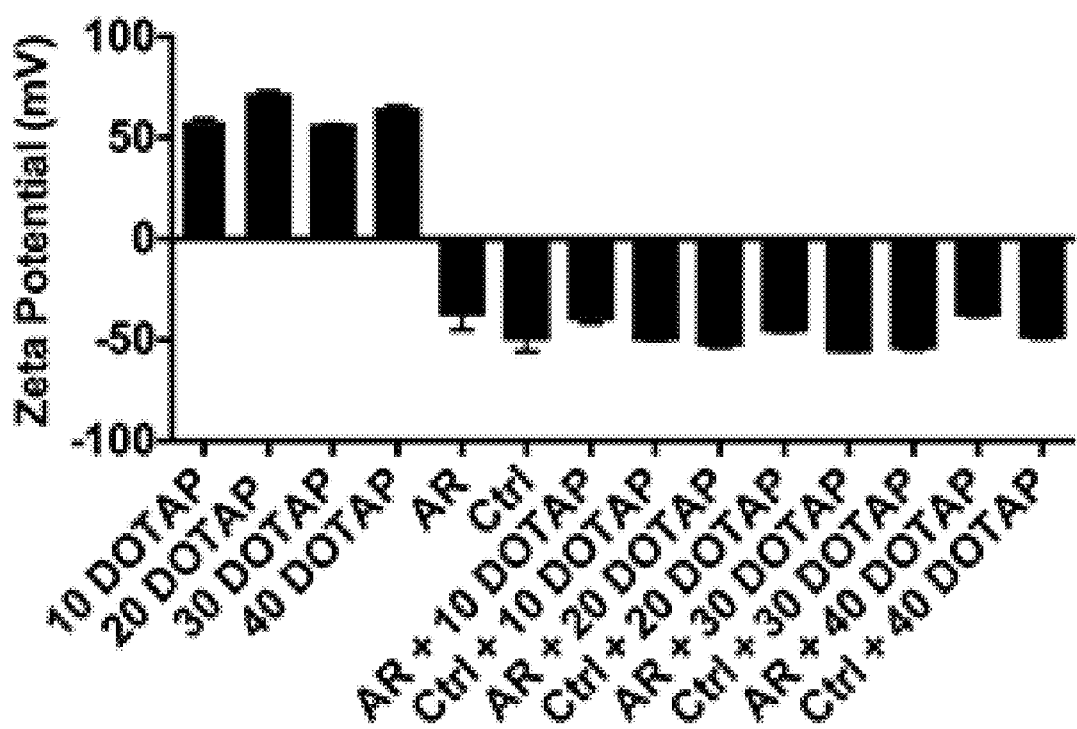

DOTAP is required for the formation of stable siRNA-TLPs. Thus, the Applicant hypothesized that DOTAP neutralizes the negative charge of RNA for assembly with anionic TLPs. To this end, the zeta potential (ζ-potential) of solutions containing DOTAP, RNA, and DOTAP-RNA mixtures were measured in water. DOTAP:RNA molar ratios of 10:1, 20:1, 30:1, and 40:1 (charge ratios ~1:4, 2:1, 3:4, 1:1) were analyzed. Data show that, regardless of the molar ratio, DOTAP had a positive ζ-potential and free RNA had a negative ζ-potential. Surprisingly, all DOTAP-RNA mixtures were negative regardless of the DOTAP:RNA molar ratio (FIG. 7B). Collectively, these data suggested that siRNA-TLP self-assembly results from DOTAP binding with TLPs that enables subsequent binding of DOTAP-RNA. To validate these assumptions, TLPs were formulated with DOTAP alone at concentrations consistent with the previously tested DOTAP-RNA molar ratios. Only TLPs mixed with DOTAP at the appropriate 30:1 or 40:1 concentration were stable to irreversible aggregation. ζ-potential measurements show that stable DOTAP-TLPs were positively charged (+31 and +34 mV, respectively), while all of the DOTAP-RNA mixtures, when added to TLPs, yielded negatively charged siRNA-TLPs (FIG. 1C). Ultimately, the collective data showed that self-assembled siRNA-TLPs are stabilized, at least in part, by negatively charged RNA molecules at the particle surface. Dynamic light scattering measurements of each of the siRNA-TLPs demonstrated a progressive increase in size with increasing DOTAP:RNA molar ratio (FIG. 1D). UV-Vis data supported that the

TABLE 1

Individual siRNA sequences. Control, AR, EZH2 sequences were designed using NCBI software. Uppercase letters indicate RNA bases. Two deoxyribose bases reside on the 3' end of each sequence and are denoted by a lower case "d" followed by a capital letter. The 5' end of each antisense sequence contains a 5'phosphate. Fluorescent cyanine dyes are denoted by "Cy" followed by the specific cyanine fluorophore. The sequences below correspond to SEQ ID NOs: 1-10 from top to bottom, respectively.

Figure 1E:
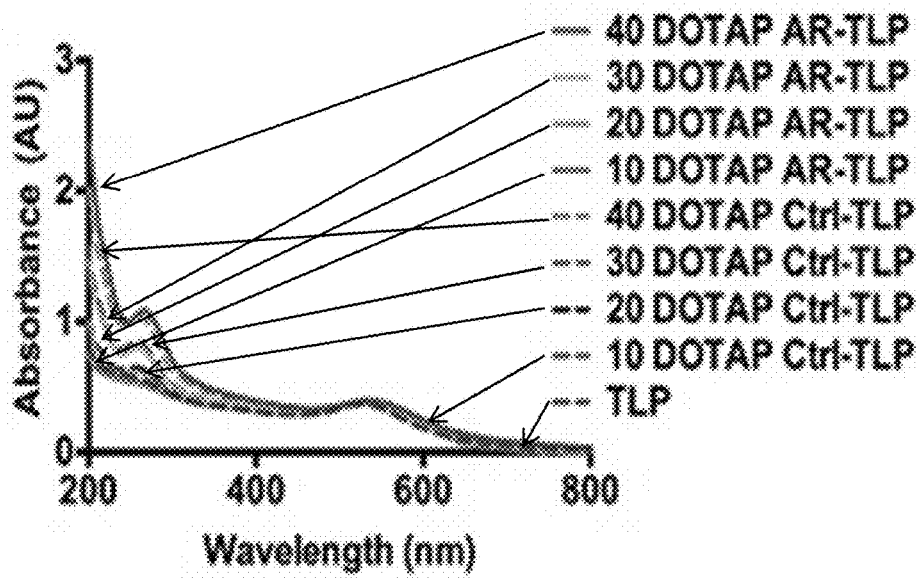

| Sequence Name | Sequence |
| --- | --- |
| Control Sense | 5'-GCAUUCUUAAACUCGUAAAdTdT-3' |
| Control Antisense | 5-Phosphate UUUACGAGUUUAAGAAUGCdAdA-3' |
| Control Sense (Cyanine-labeled) | 5'-GCAUUCUUAAACUCGUAAAdTdT (Cy3 or 5)-3' |
| Control Antisense (Cyanine-labeled) | 5-Phosphate UUUACGAGUUUAAGAAUGCdAdA (Cy5)-3' |
| AR Sense | 5'-GCCCAUUGACUAUUACUUUdTdT-3' |
| AR Antisense | 5'-Phosphate AAAGUAAUAGUCAAUGGGCdAdA-3' |
| AR Sense (Cyanine-labeled) | 5'-GCCCAUUGACUAUUACUUUdTdT (Cy3 or 5)-3' |
| AR Antisense (Cyanine-labeled) | 5'-Phosphate AAAGUAAUAGUCAAUGGGCdAdA (Cy5)-3' |
| EZH2 Sense | 5'-GAGGUUCAGACGAGCUGAUdTdT-3' |
| EZH2 Antisense | 5'-Phosphate AUCAGCUCGTCUGAACCUCdAdA-3' | progressive increase in siRNA-TLP size was due, at least in part, to increasing amounts of RNA (FIG. 1E).

siRNA-TLPs Require TLPs to Function In Vitro

Figures 1F, 2A:
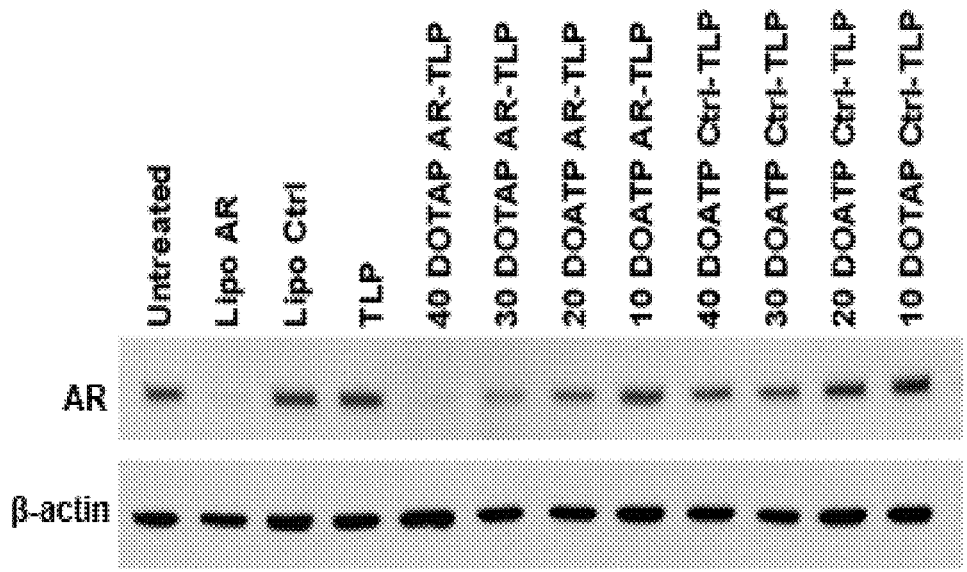
FIGS. 2A-2D show siRNA-TLP characterization.
Figures 7C, 7D:
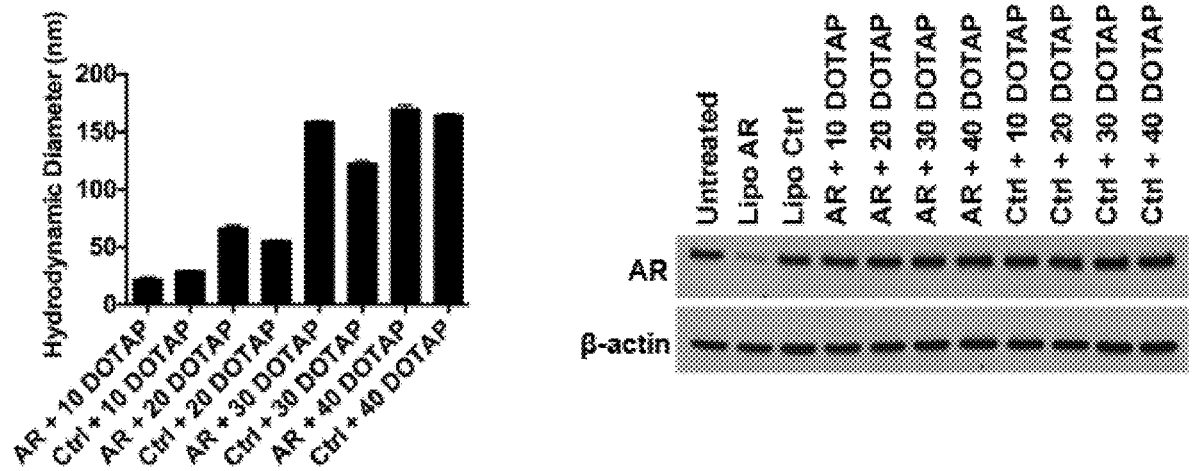
Figure 7E:
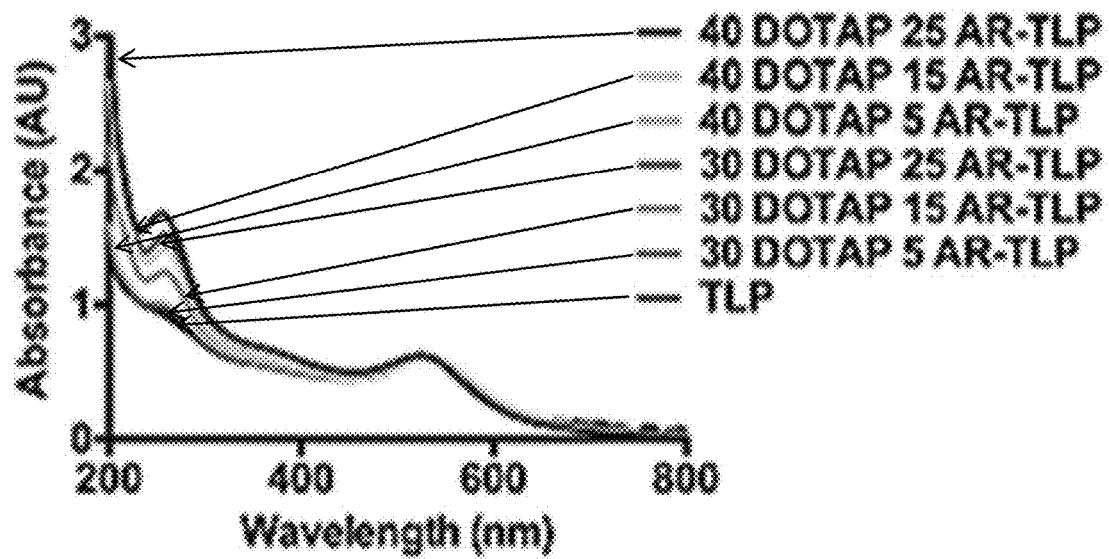
Figure 7F:
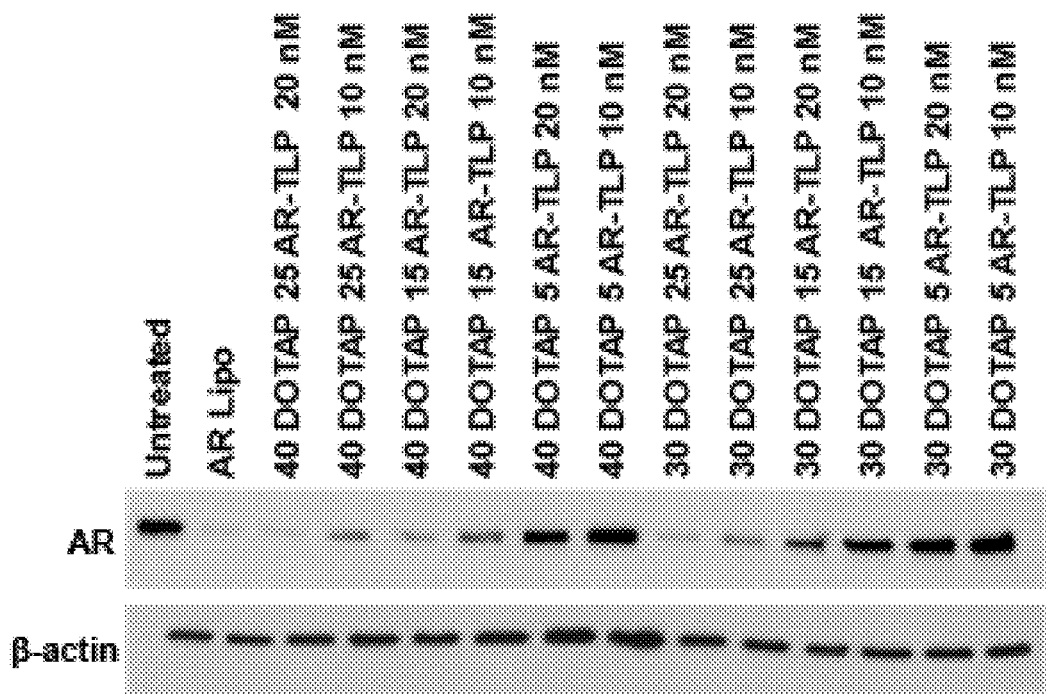

To measure siRNA-TLP function, the Applicant treated lymph node derived prostate cancer cells (LNCaP), known to express AR, with siRNA-TLPs made using each DOTAP: RNA molar ratio used above. Western blotting demonstrated that the most potent reduction in AR expression was achieved with the 40:1 siRNA-TLPs followed in step-wise order by the 30:1, 20:1, and 10:1 molar ratios (FIG. 1F). As a critical control, because DOTAP has been employed as a nucleic acid transfection reagent,[32,33] the Applicant explored if TLPs are required for siRNA-TLP function. Importantly, data showed that mixtures of DOTAP-RNA particles without TLPs (FIG. 7C) did not function to knockdown target AR expression (FIG. 7D). Next, the optimal RNA:TLP molar ratio was explored using the 40:1 and 30:1 DOTAP: RNA siRNA-TLPs. In all appropriate pairwise comparisons, UV-Vis data showed that the 40:1 DOTAP:RNA and the 25:1 RNA:TLP molar ratios were optimal for RNA assembly to siRNA-TLPs (FIG. 7E). Treatment of LNCaP cells with each of the particles demonstrated dose-dependent reductions in AR expression consistent with the amount of RNA associated with TLPs (FIG. 7F). In short, the self-assembly of siRNA-TLPs can be tailored to potently regulate target gene expression, and the optimal siRNA-TLP resulted from the use of 40:1 (DOTAP:RNA) and 25:1 (RNA:TLP) molar ratios, respectively.

siRNA-TLPs Characterization

Figure 2B:
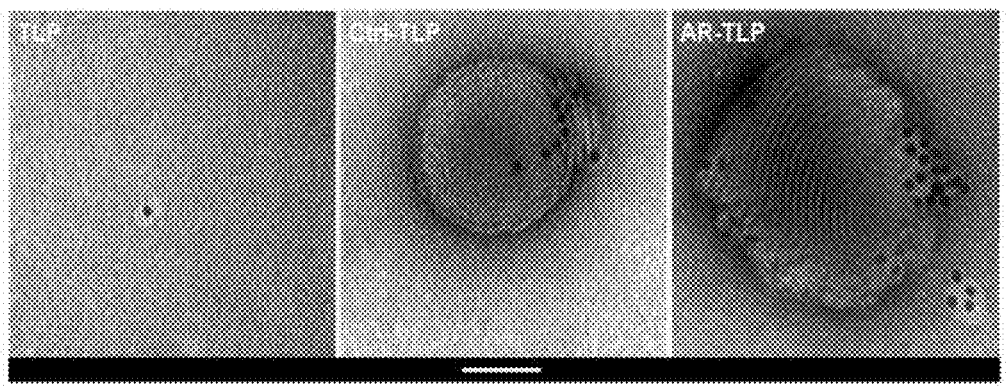
Figure 2C:
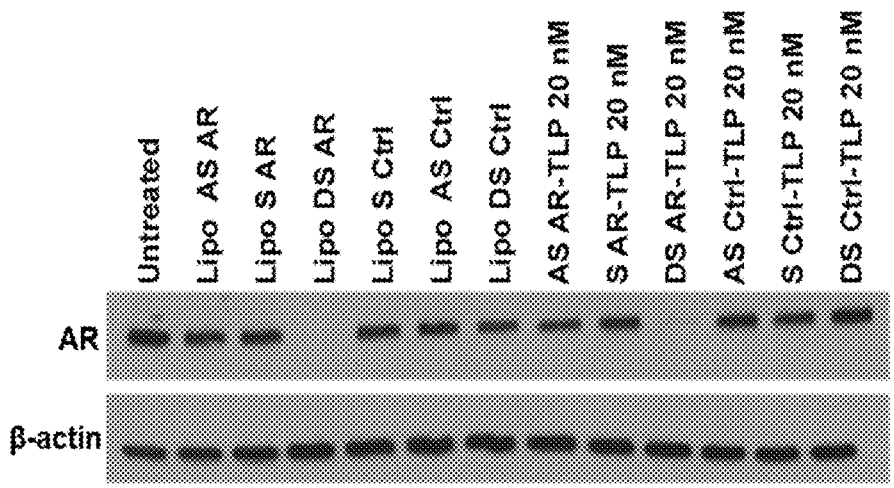
Figure 2D:
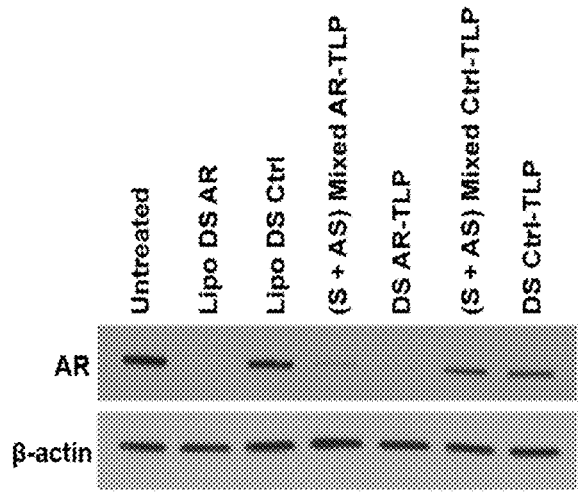
Figure 8:
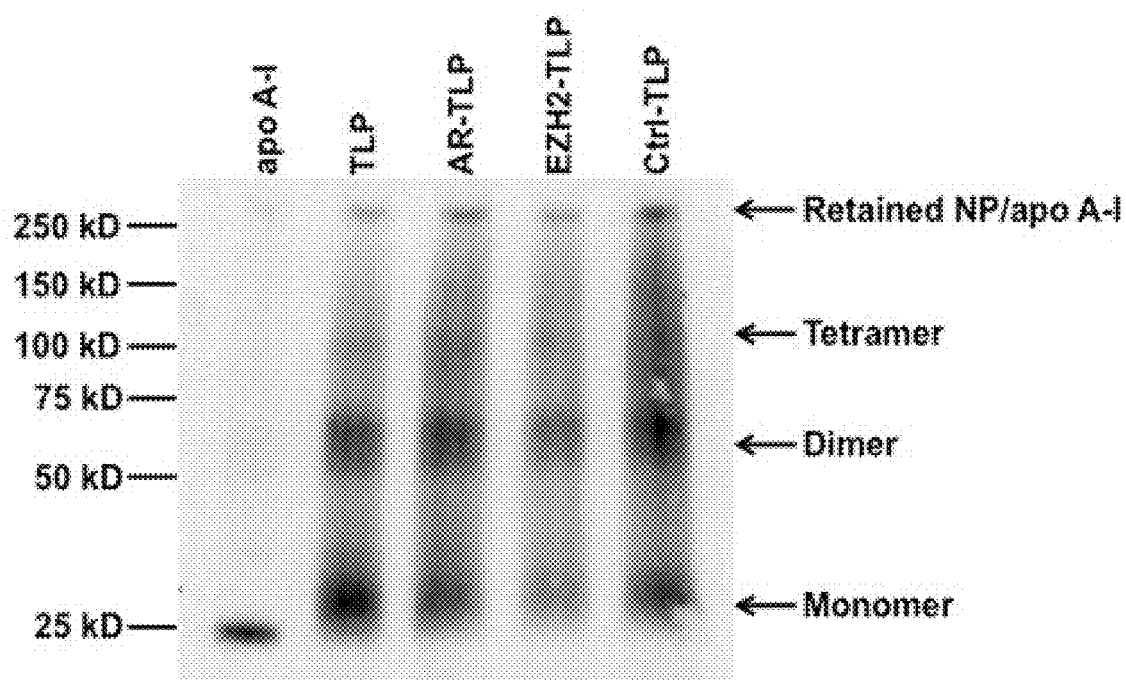
FIG. 8 shows a Western blot of apolipoprotein A-I associated with siRNA-TLP particles. (Lane 1) Purified human apo A-I. (Lanes 2-5) apo A-I associated with siRNA-TLPs.

Multiple modalities were used to characterize optimized siRNA-TLPs. Fluorescently labeled apo A-I, cholesterol, DOPC, DOTAP, and RNA were used to quantify the amount of each of these molecules in siRNA-TLPs (FIG. 2A). In addition, western blotting was performed to confirm apo A-I presence on the TLP and siRNA-TLP (FIG. 8). Transmission electron microscopy (TEM) was used to obtain images of TLPs and siRNA-TLPs. As shown in FIG. 2B, there is clear indication of TLP surface functionalization. TEM images of the siRNA-TLPs revealed spherical particles that show TLP self-assembly with solid alternating layers of DOTAP and RNA. Further, because siRNA-TLPs are formulated with a mixture of ssRNAs, the Applicant sought to conclusively demonstrate that siRNA-TLPs incorporate and require each complement of the siRNA duplex for optimal function.[34,35] Particles were synthesized with only the sense (S) or anti-sense (AS) RNA sequence of the siRNA pair and their function was compared to siRNA-TLPs synthesized with both sequences (DS). Only siRNA-TLPs synthesized with both sequences of the siRNA pair functioned to reduce AR expression (FIG. 2C). In addition, the Applicant determined if function could be achieved by mixing siRNA-TLPs synthesized with only the S or AS RNA sequence. Ultimately, mixed siRNA-TLPs functioned similarly to siRNA-TLPs synthesized with both sequences (FIG. 2D). These data support that optimal gene regulation requires delivery of both sequences of the siRNA pair, and that siRNA can be delivered as component single strands on a single or mixed population of siRNA-TLPs.

siRNA-TLPs In Vitro Function and Modular Design

Figure 3A:
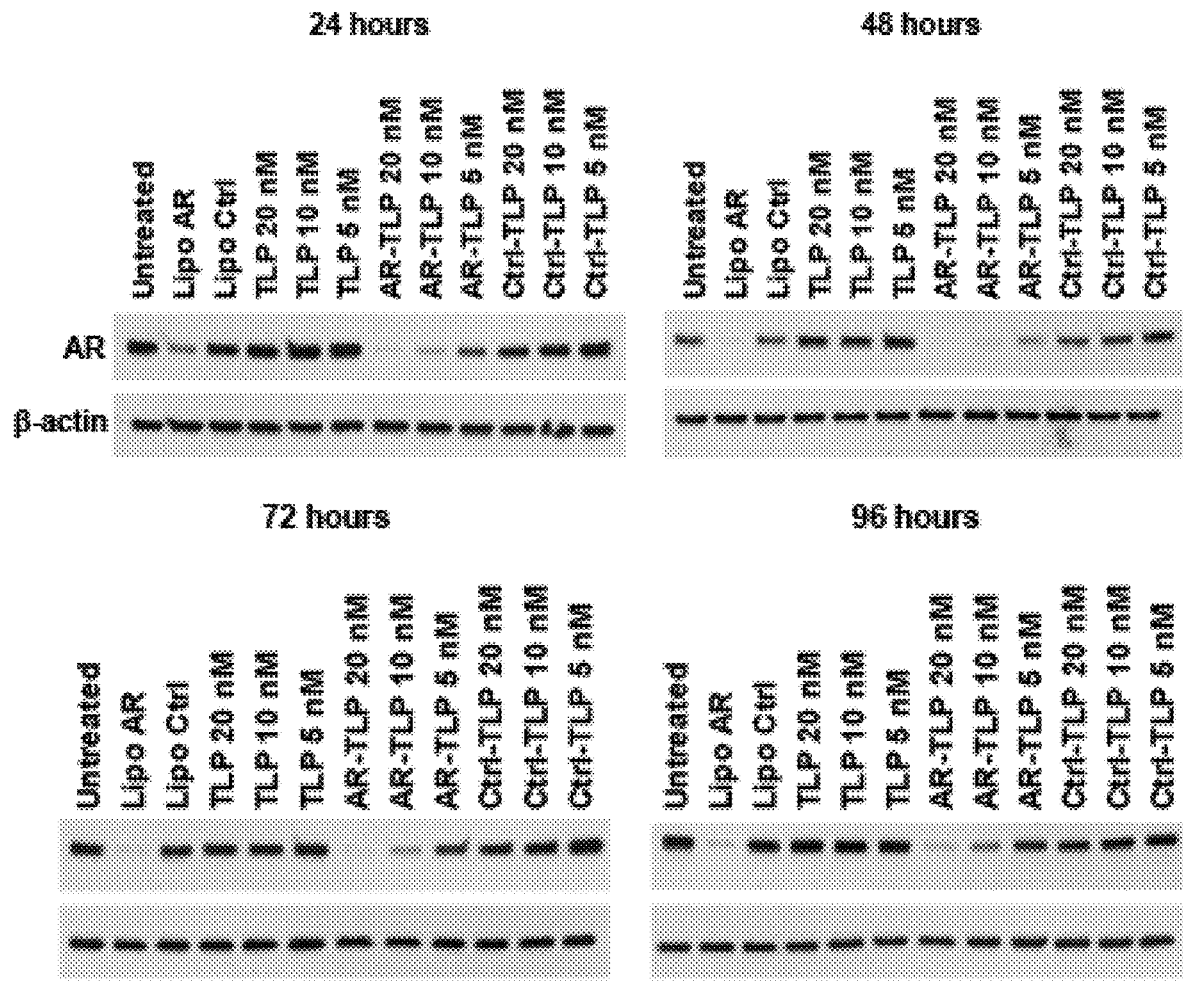
FIGS. 3A-3C show in vitro function of siRNA-TLP and cell viability.

In vitro siRNA-TLP efficacy was determined over time. LNCaP cells were treated with siRNA-TLPs for 24, 48, 72, and 96 hours at Au NP concentrations of 20, 10, and 5 nM. Western blot data demonstrated that siRNA-TLPs reduced AR protein expression in a time and dose-dependent fashion (FIG. 3A). In addition, siRNA-TLPs reduced AR mRNA expression measured using qRT-PCR (FIG. 9A). In addition to LNCaP cells, AR targeted siRNA-TLPs were tested in a cell culture model of advanced prostate cancer known to be resistant to a common AR blocker, enzalutamide (MDV3100).[36] As in LNCaP cells, siRNA-TLPs reduced AR expression in dose response (FIG. 9B).

Figure 3B:
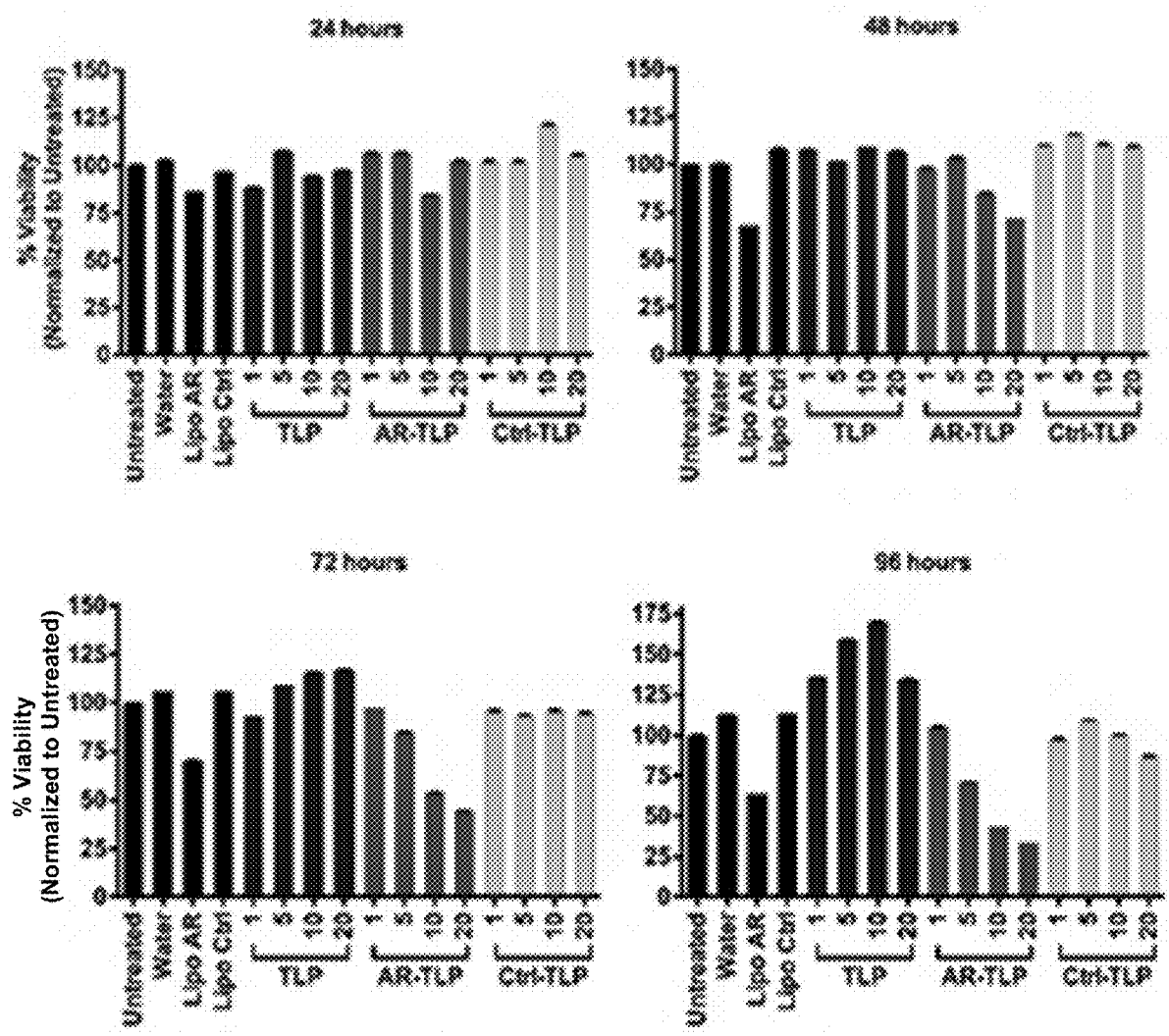
Figure 3C:
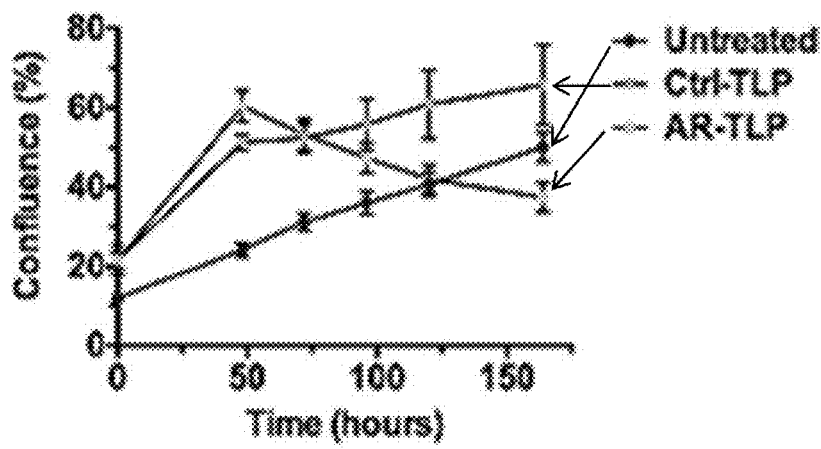
Figure 3C:
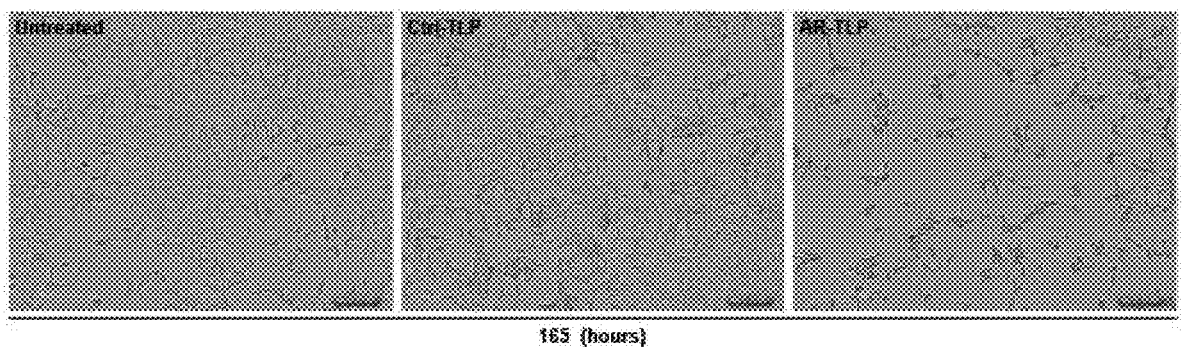

The AR is important for prostate cancer cell survival.[37] Thus, LNCaP cell viability was tested after treatment with siRNA-TLPs. The AR siRNA-TLPs reduced LNCaP cell viability over time and with a clear dose-response (FIG. 3B). Control siRNA-TLPs did not reduce cell viability demonstrating no apparent toxicity and siRNA specificity. In addition, serial images were collected over six days after cell treatment. Using imaging software and analysis, data showed that cell confluence was reduced in the presence of AR-TLPs over time, and images taken at 165 hours confirmed reduced cell confluence (FIG. 3C).

Figure 9C:
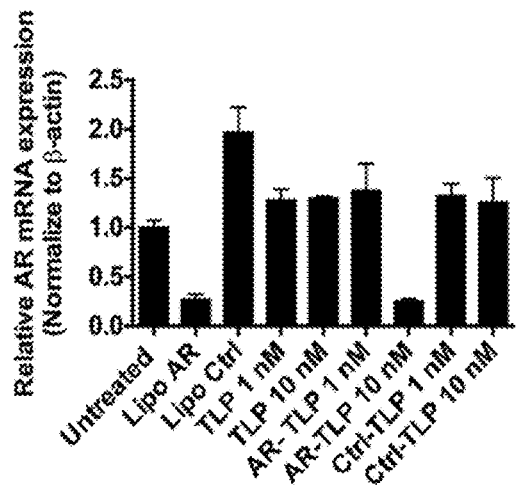
Figure 9C:
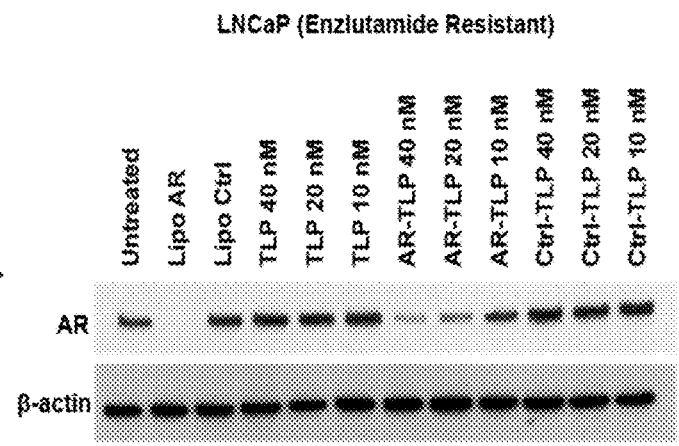
Figure 9C:
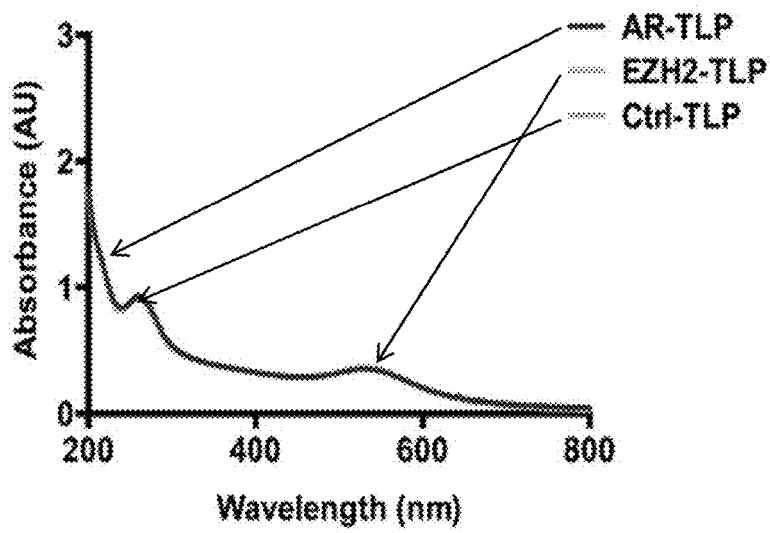
Figure 9D:
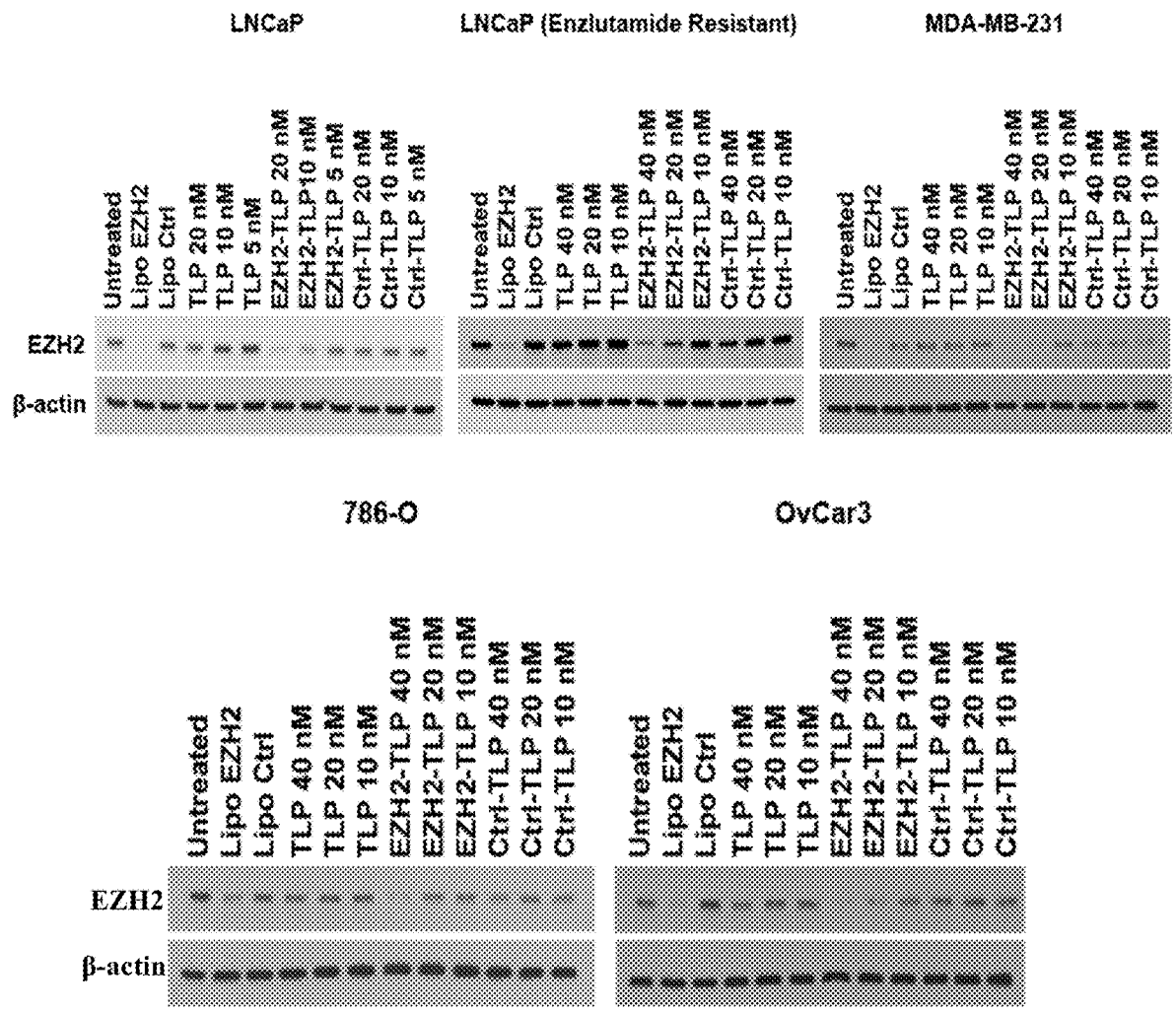

Modular addition of desired siRNA sequences with TLPs would enable rapid and facile targeting of different proteins and protein variants relevant to cancer in individual patients. Thus, in addition to targeting AR, siRNA-TLPs targeting EZH2, a histone lysine N-methyltransferase enzyme, known for its oncogenic relevance in prostate cancer and other malignancies such as breast, renal, and ovarian cancers, were synthesized.[38-41] UV-Vis data demonstrated equivalent RNA assembly to EZH2-, AR-, and Ctrl-TLPs (FIG. 9C). Data showed that siRNA-TLPs reduce EZH2 expression in LNCaP, enzalutamide resistant LNCaP cells, MDA-MB-231 (breast cancer), 786-O (renal cell carcinoma), and OvCar3 (ovarian cancer) in a dose-dependent fashion (FIG. 9D).

siRNA-TLPs Taken Up by Cell and Targeted to SR-B1

Figure 4A:
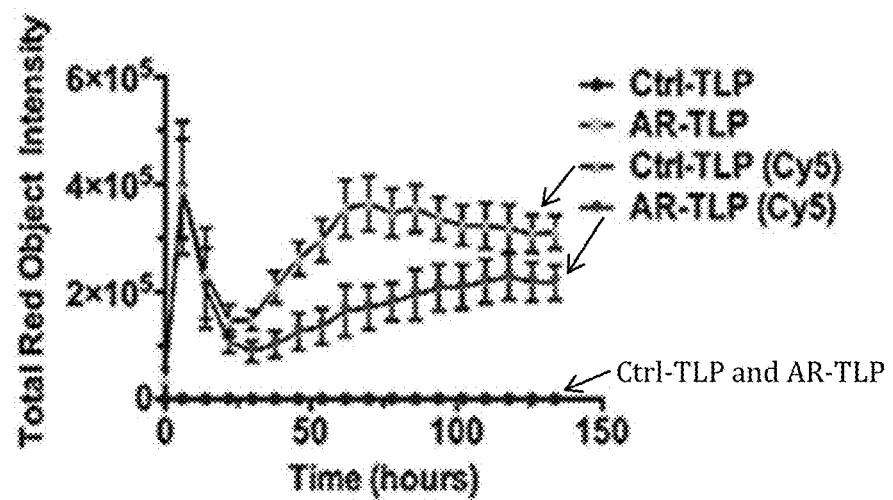
FIGS. 4A-C show cell uptake of siRNA-TLP and functional dependence on scavenger receptor type B-1 (SR-B1).
Figure 4B:
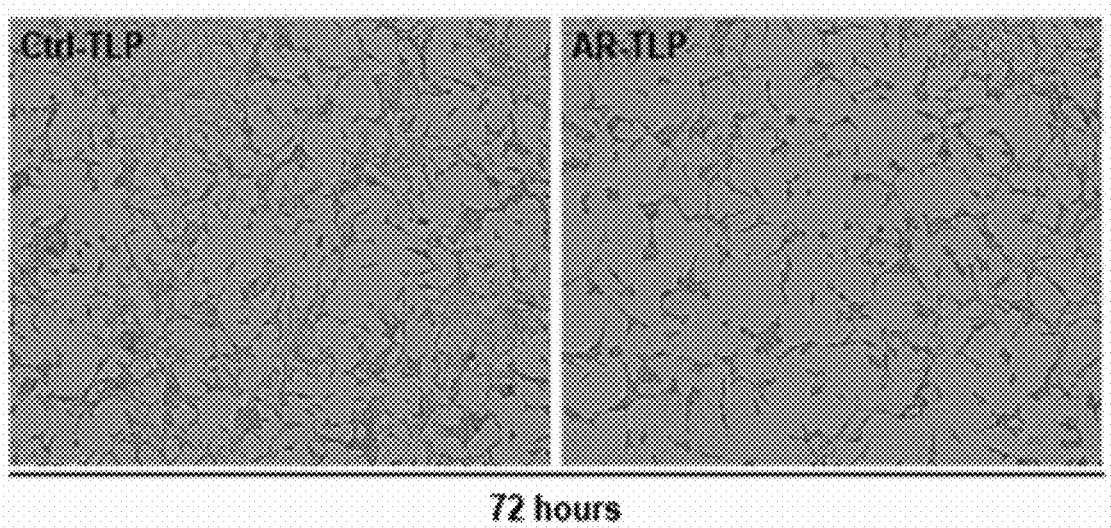
Figure 10A:
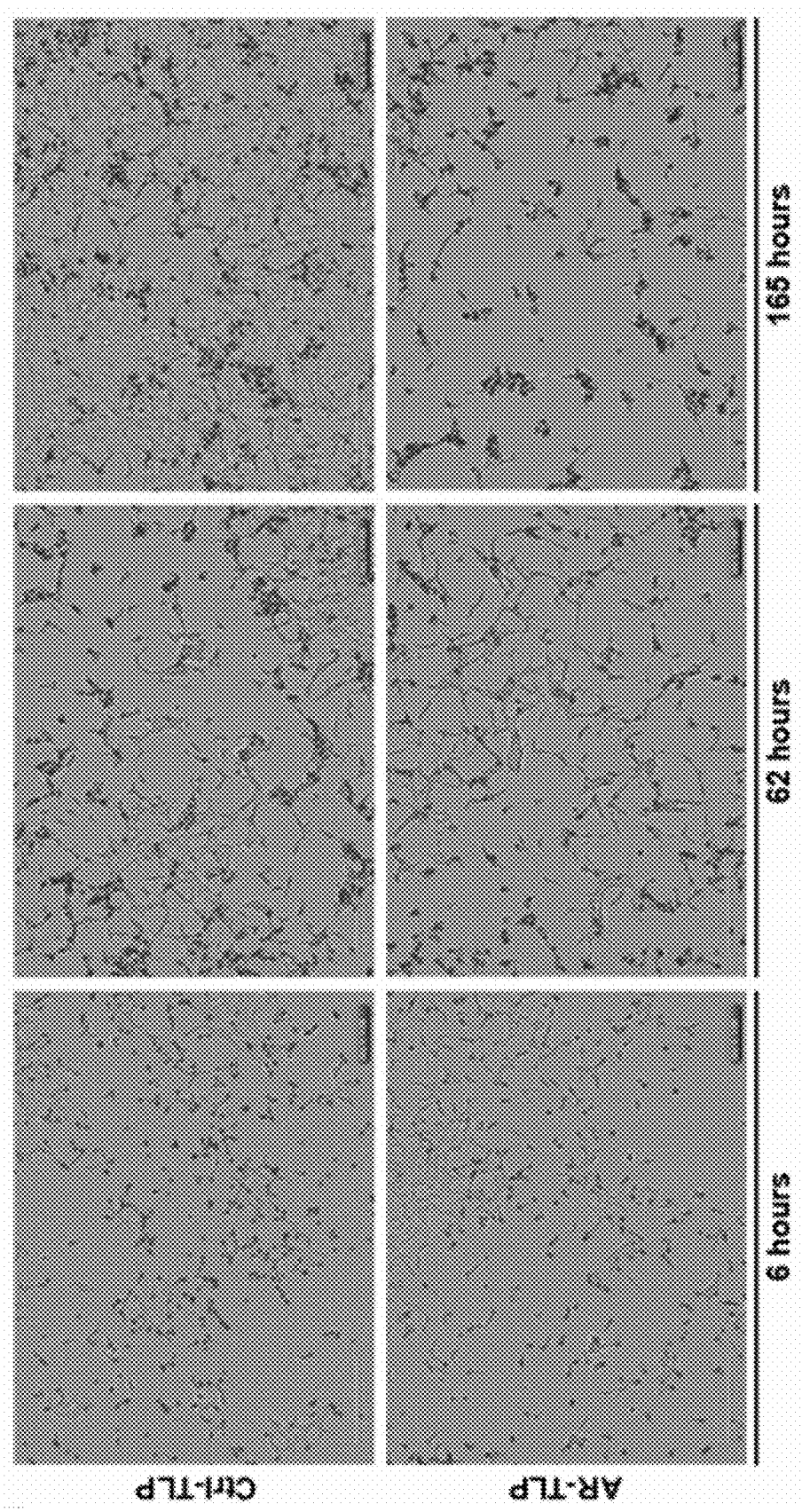
FIGS. 10A-10C show particle uptake of siRNA-TLP by cultured LNCaP cells, SR-B1 expression by multiple target cell lines, and SR-B1 knockdown in LNCaP cells.

Next, to study cellular internalization of siRNA-TLPs, LNCaP cells were treated with siRNA-TLPs synthesized with fluorophore-labeled RNA. Ctrl- and AR-TLP uptake and cell confluence were captured with imaging software after treating cells for 165 hours. Data showed an apparent two-phase uptake of siRNA-TLPs (FIG. 4A and FIG. 10A). Representative images of the second uptake phase are presented in FIG. 4B.

Figure 4C:
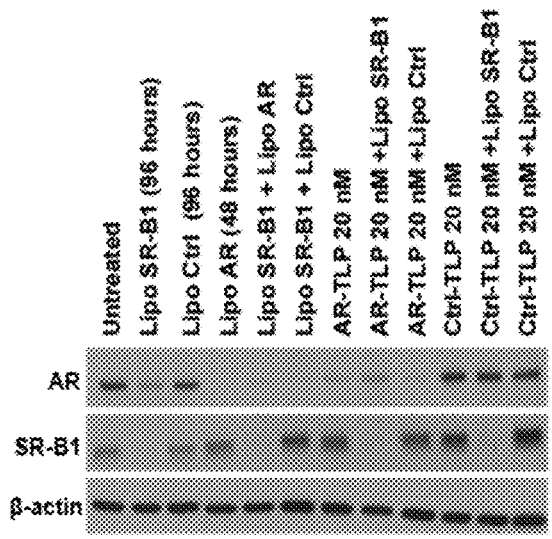
Figure 4C:
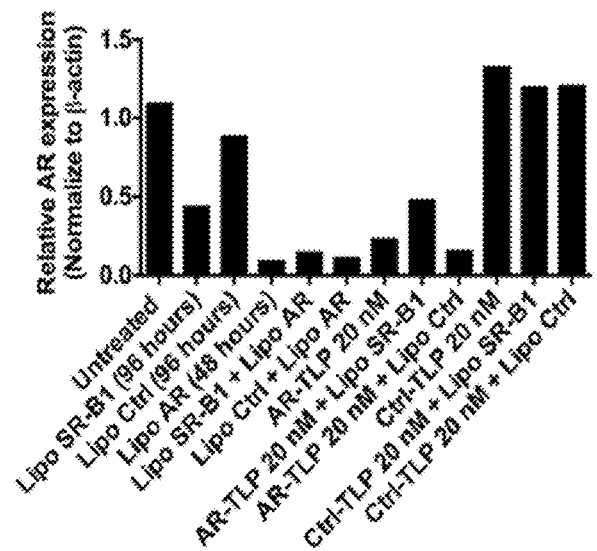
Figure 10B:
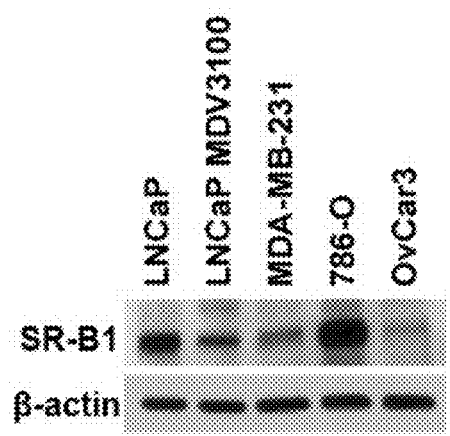
Figure 10C:
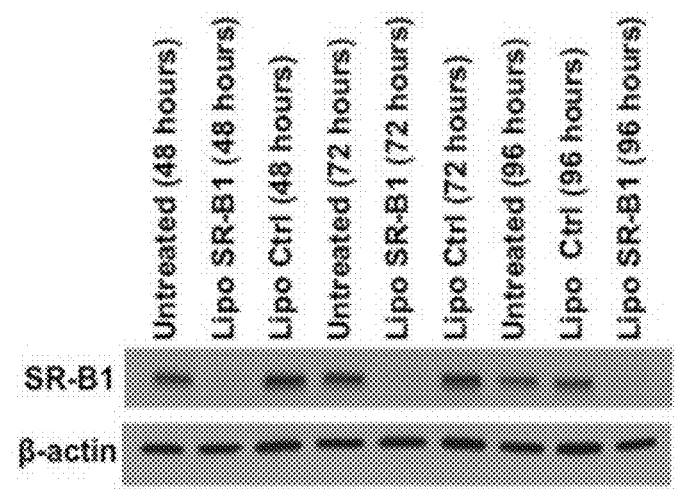

To explore if the high-affinity HDL receptor, SR-B1, was required for siRNA-TLP function, western blotting was performed to confirm SR-B1 expression in all of the cultured cells used in this study (FIG. 10B). Of note, human prostate cancer, breast cancer, and renal cell carcinoma, among others, have been shown to overexpress SR-B1.[21,42-44] In LNCaP cells, optimal SR-B1 knockdown using conventional LIPOFECTAMINE® RNAiMAX was tested in order to ensure maximal SR-B1 reduction at the time of siRNA-TLP addition (48 hours), and that SR-B1 knockdown was maintained for the duration of the experiment to subsequently test siRNA-TLP function (96 hours) (FIG. 10C). Thus, conventional SR-B1 knockdown was performed in LNCaP cells followed by addition of siRNA-TLPs, or controls, targeting AR. Following treatments, data showed that conventional knockdown of SR-B1 partially reduces AR expression, which is a finding supported by the published literature but requires further study[45,46] Quantitative analysis showed that AR-TLPs added after SR-B1 knockdown do not function to reduce AR expression. On the other hand, conventional delivery of siRNA targeting AR functioned to reduce AR expression in the presence of SR-B1 knockdown (FIG. 4C). These data clearly show that active targeting of SR-B1 is required for siRNA-TLP function.

Nuclease Stability of siRNA-TLPs

Figure 5A:
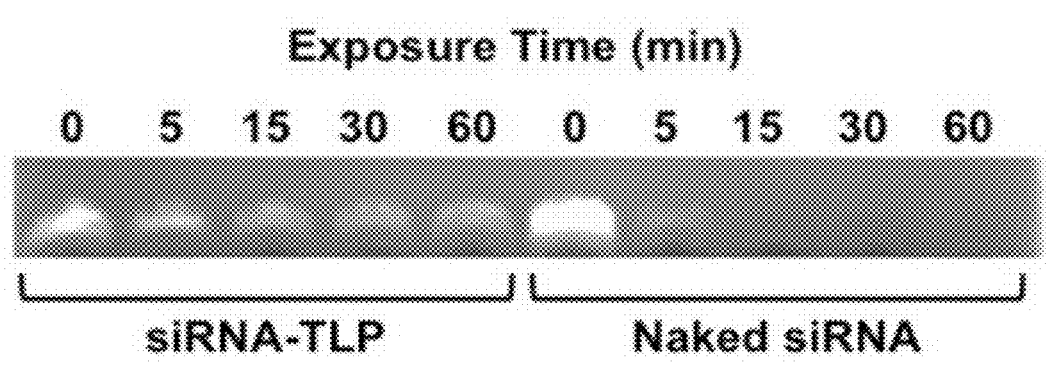
FIGS. 5A-5C show the stability of RNA on siRNA-TLP and siRNA-TLP function after incubation in human serum.
Figure 5B:
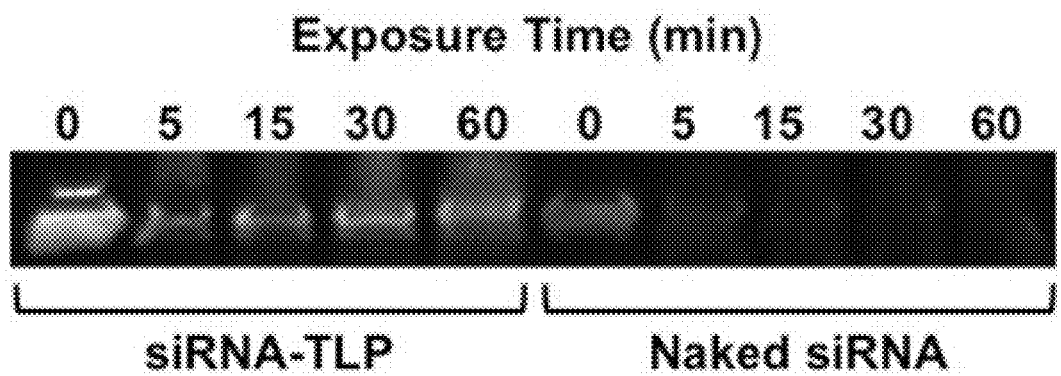
Figure 5C:
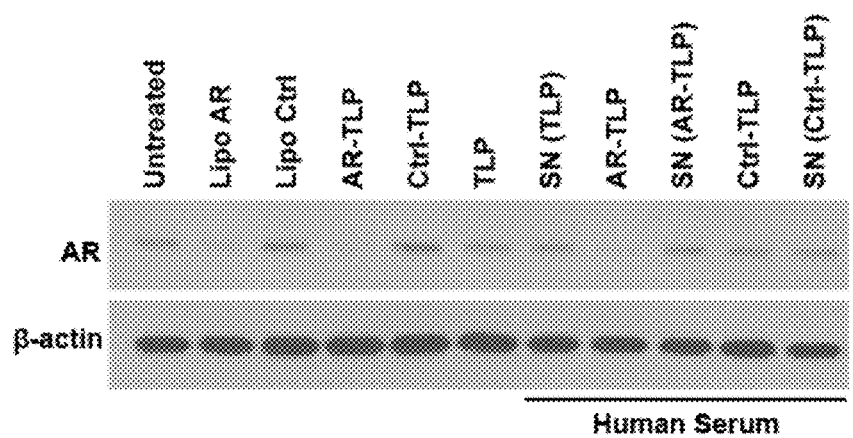
Figure 11:
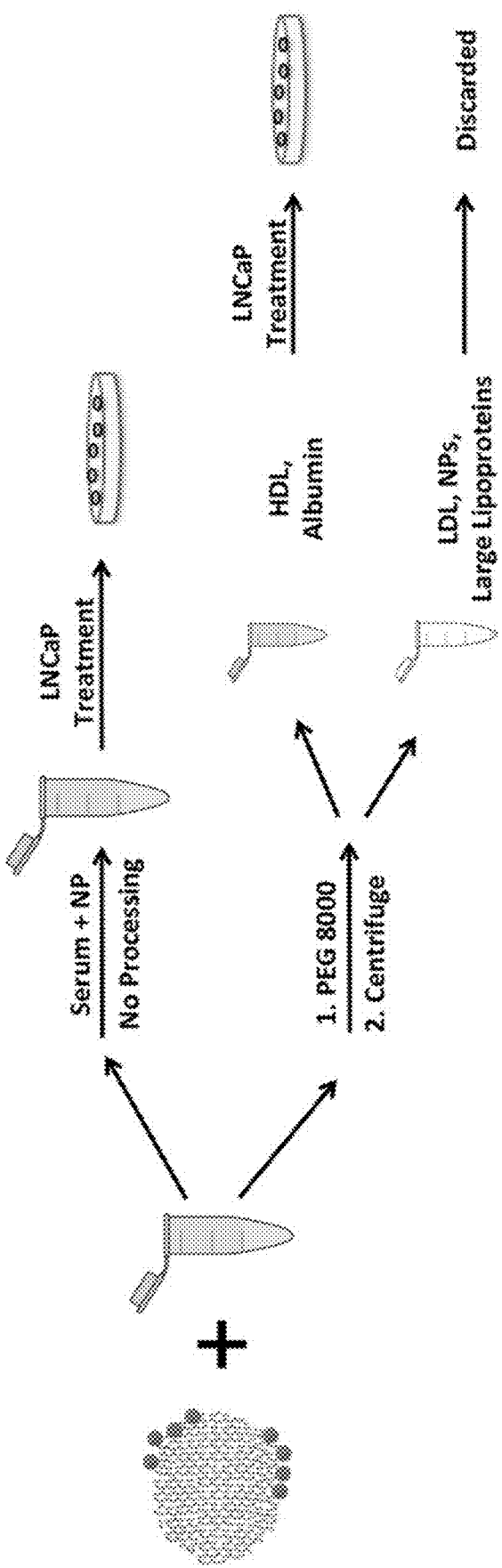
FIG. 11 shows an experimental design for testing siRNA-TLP function after prolonged incubation in human serum. (Top arrow) To test siRNA-TLP function after serum incubation, siRNA-TLPs were incubated in human serum for 1 hour prior to LNCaP cell treatment. (Bottom arrow) To test RNA exchange to native HDL and/or albumin, siRNA-TLP were incubated in human serum for 1 hour. After incubation siRNA-TLPs were isolated from the serum fraction containing native HDL and albumin. The isolated HDL and albumin was used to treat LNCaP cells.

Natural HDLs stabilize RNA from nuclease degradation in blood and actively deliver RNA to target cells[12,15]. To demonstrate the stability of RNA assembled in siRNA-TLPs, free siRNA and siRNA-TLPs were exposed to RNase A and human plasma. Gel electrophoresis was used to determine RNA stability. RNA assembled in siRNA-TLP was protected from degradation after exposure to RNase A (FIG. 5A) and human plasma (FIG. 5B). Further, the Applicant tested the function of siRNA-TLPs after incubation in human serum, and if siRNA-TLPs directly deliver RNA to target cells or if RNA is exchanged with native HDL in serum and indirectly delivered. See FIG. 11 for experimental design. Treatment of LNCaP cells with siRNA-TLPs after incubation in human serum demonstrated reduced AR expression to the same level as siRNA-TLPs directly added to cultured cells. Native HDL isolated from serum after incubation with siRNA-TLPs had no effect on AR expression (FIG. 5C). In addition, siRNA-TLPs were incubated in human serum for 2, 4, 6, 10, and 24 h at 37° C. The siRNA-TLP that had been incubated in serum were then added to cultured LNCaP cells and, following 48 hours of incubation, AR expression was measured. ARTLPs continue to reduce AR expression, even after incubation in serum for 10 hours (Data not shown). These data show that siRNA is stable to degradation and is directly delivered to target cells by siRNA-TLPs.

Efficacy of siRNA-TLPs In Vivo

Figure 6A:
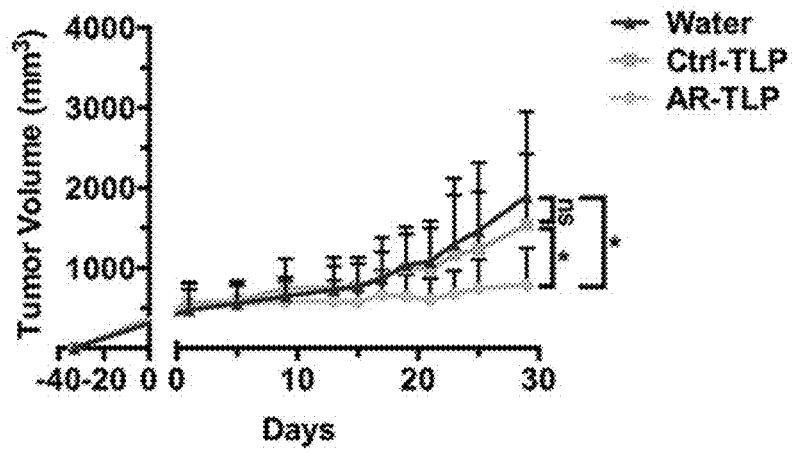
FIGS. 6A-6F show in vivo function of siRNA-TLP.
Figure 6B:
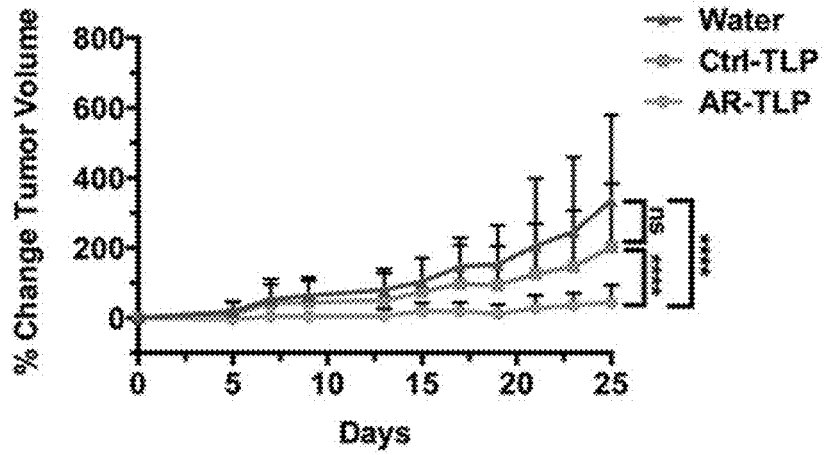
Figure 6C:
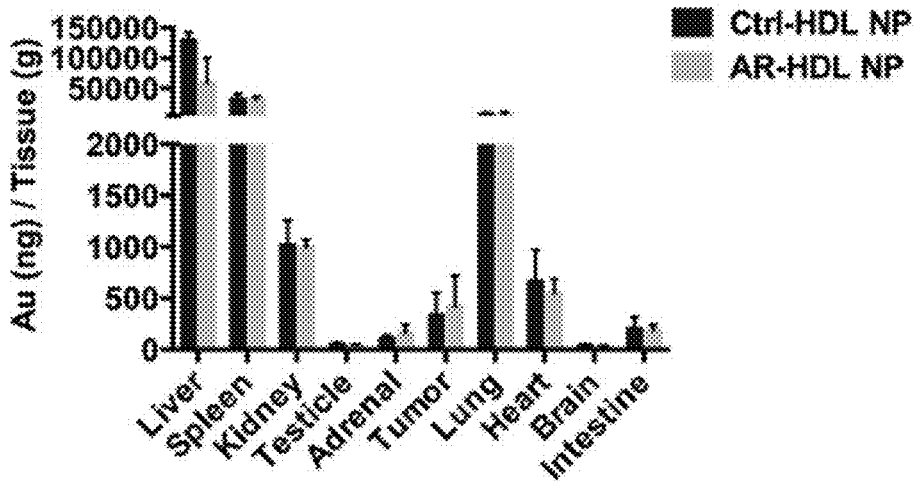
Figure 6D:
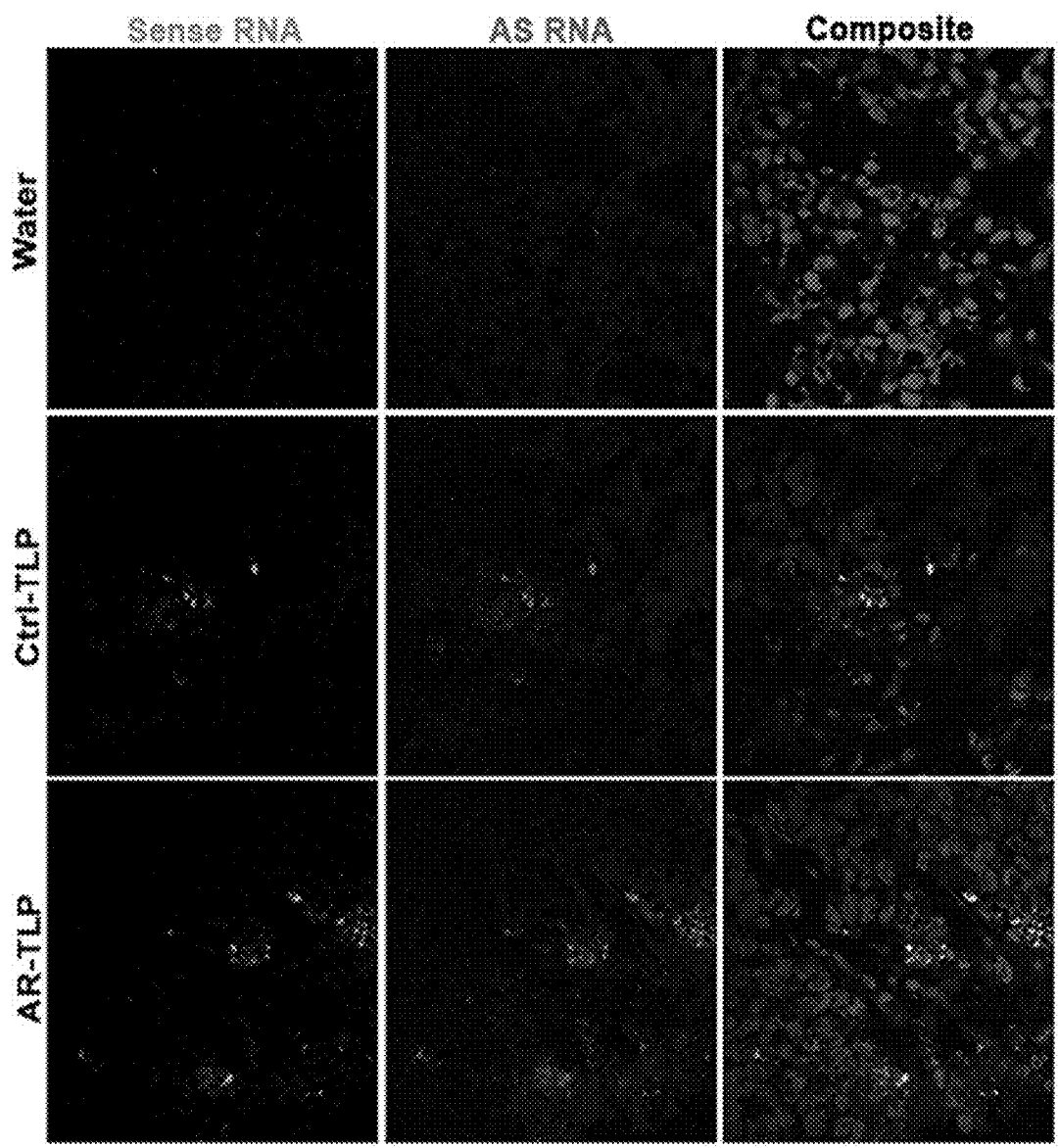
Figure 6E:
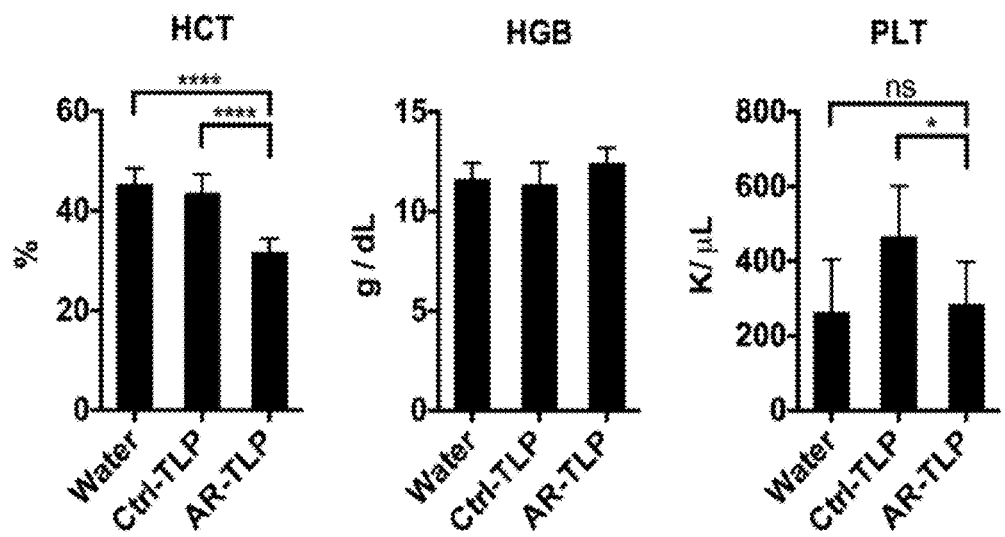
Figure 6F:
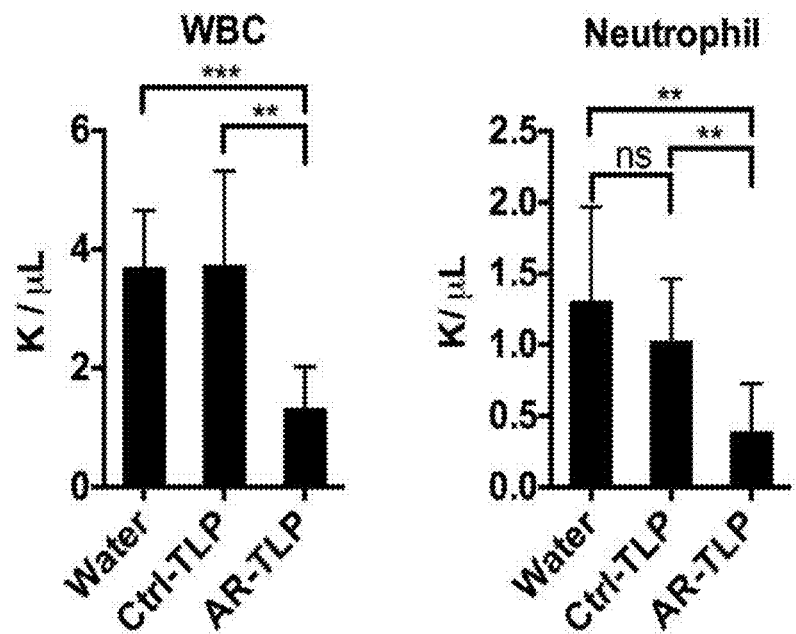
Figure 12A:
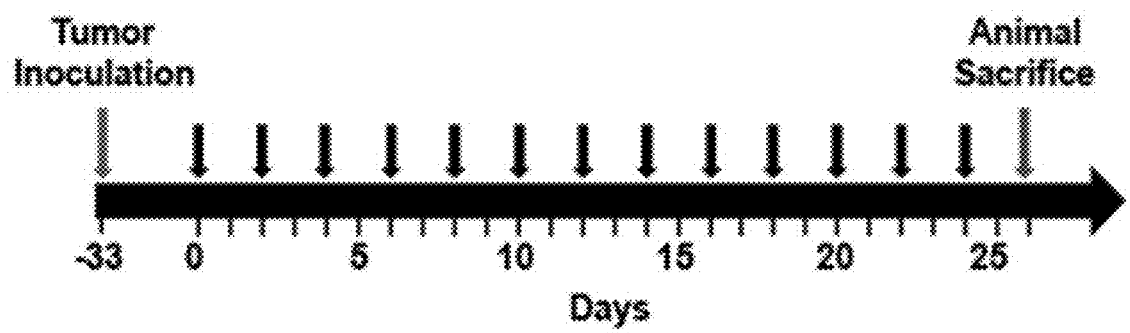
FIGS. 12A-12C show in vivo treatment scheme, mouse weight, and tissue H&E sections following treatment. (FIG.

Next, the in vivo efficacy of siRNA-TLPs was investigated. Subcutaneous LNCaP xenografts were established in male nude mice. A total of thirteen treatments were administered via tail vein and tumor volumes were recorded over a 26-day period (FIG. 12A). Mice treated with AR-TLPs (0.7 mg siRNA/kg) showed a significant reduction in tumor volume (FIG. 6A) and percent change in tumor volume over time (FIG. 6B). Targeted siRNA-TLP delivery to tumor tissue was assessed using inductively coupled plasmon mass spectrometry (ICP-MS) to quantify Au NPs, and confocal fluorescent microscopy to visualize RNA. ICP-MS data showed the presence of gold in tumor tissue after the treatment regimen (FIG. 6C). Following a single dose of siRNA-TLPs synthesized with fluorescently labeled RNA [sense (Cy3) and antisense (Cy5)], tumor tissue was obtained 24 hours after the injection and confocal fluorescent microscopy confirmed RNA in tumor tissue (FIG. 6D). Known consequences of systemic AR knockdown in mice include a reduction in hematocrit and neutrophils.[47] Indeed, a significant reduction in hematocrit (HCT) (FIG. 6E), white blood cells (WBC) (FIG. 6F), and neutrophils (FIG. 6F) was measured in AR-TLP treated mice. Consistent with published literature,[47] no change in hemoglobin (HGB) or platelets (PLT) was measured (FIG. 6E).

Figure 12B:
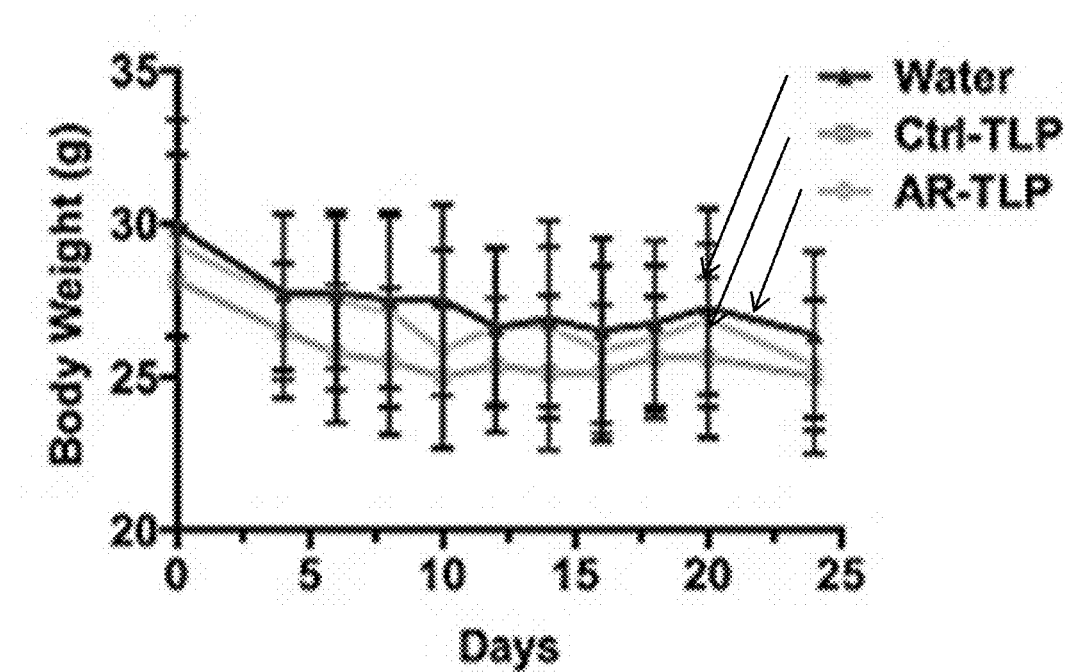
Figure 12C:
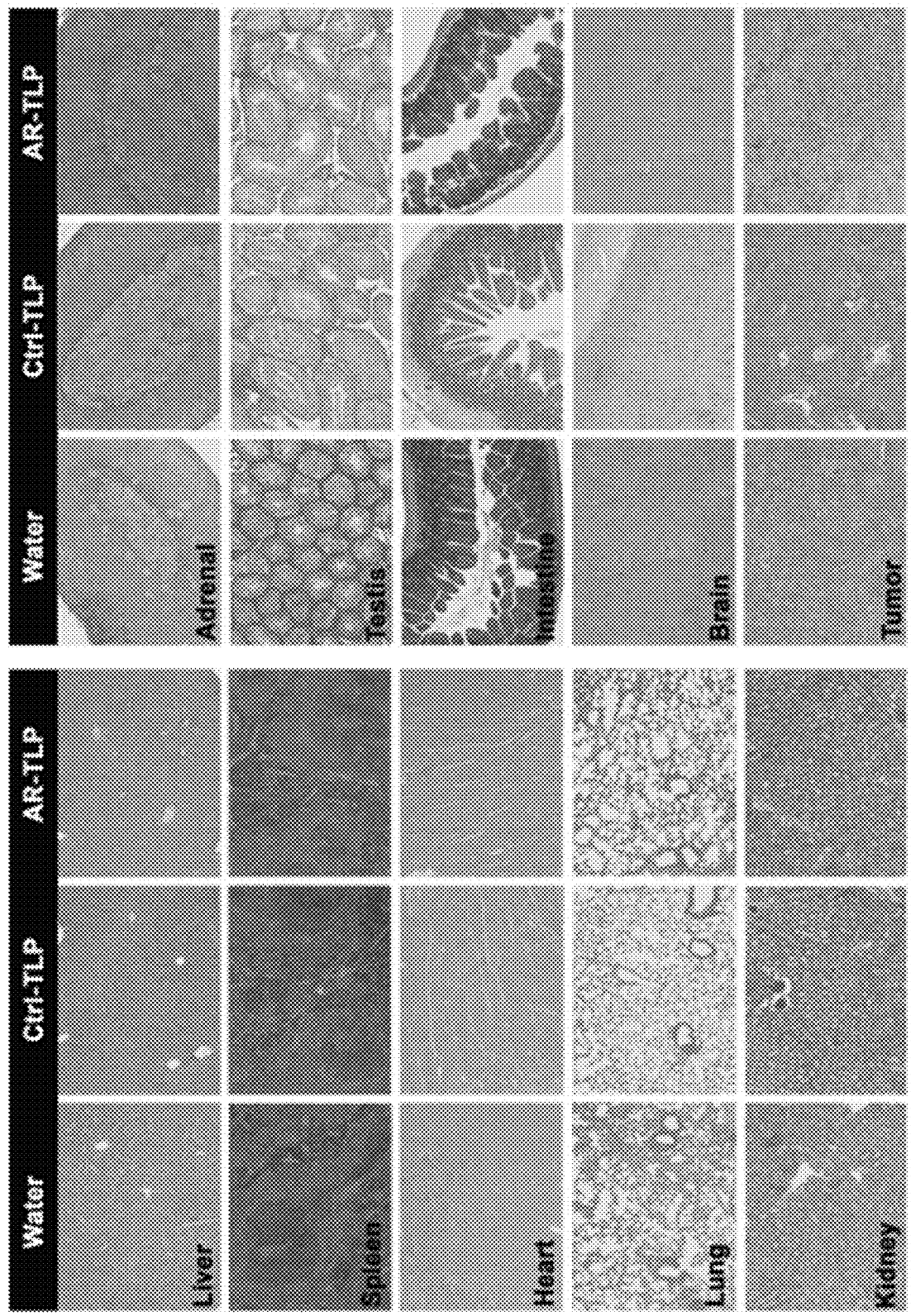
Figure 13A:
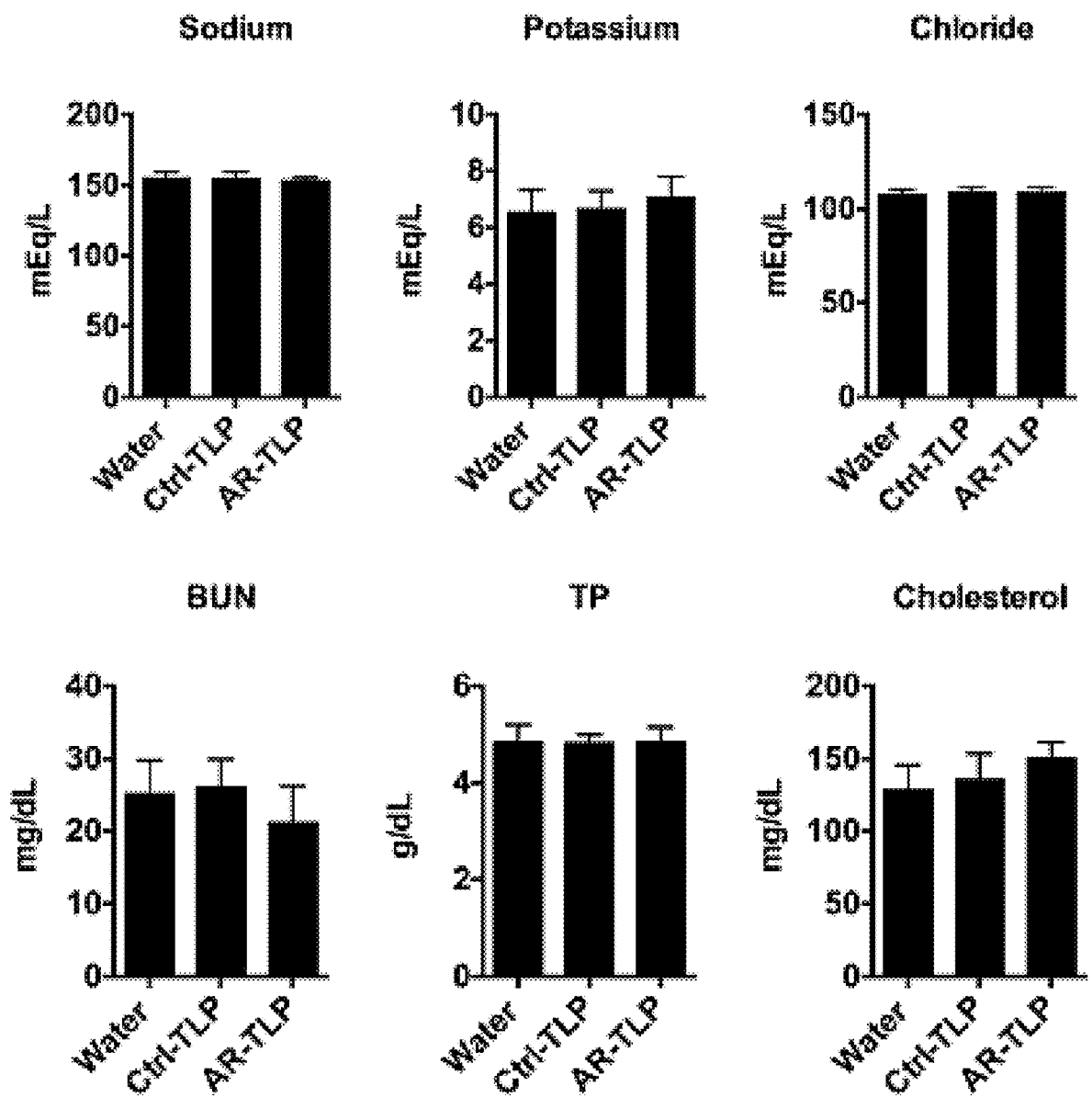
FIGS. 13A-13B show serum chemistry and liver function analysis after siRNA-TLP treatment regimen.
Figure 13B:
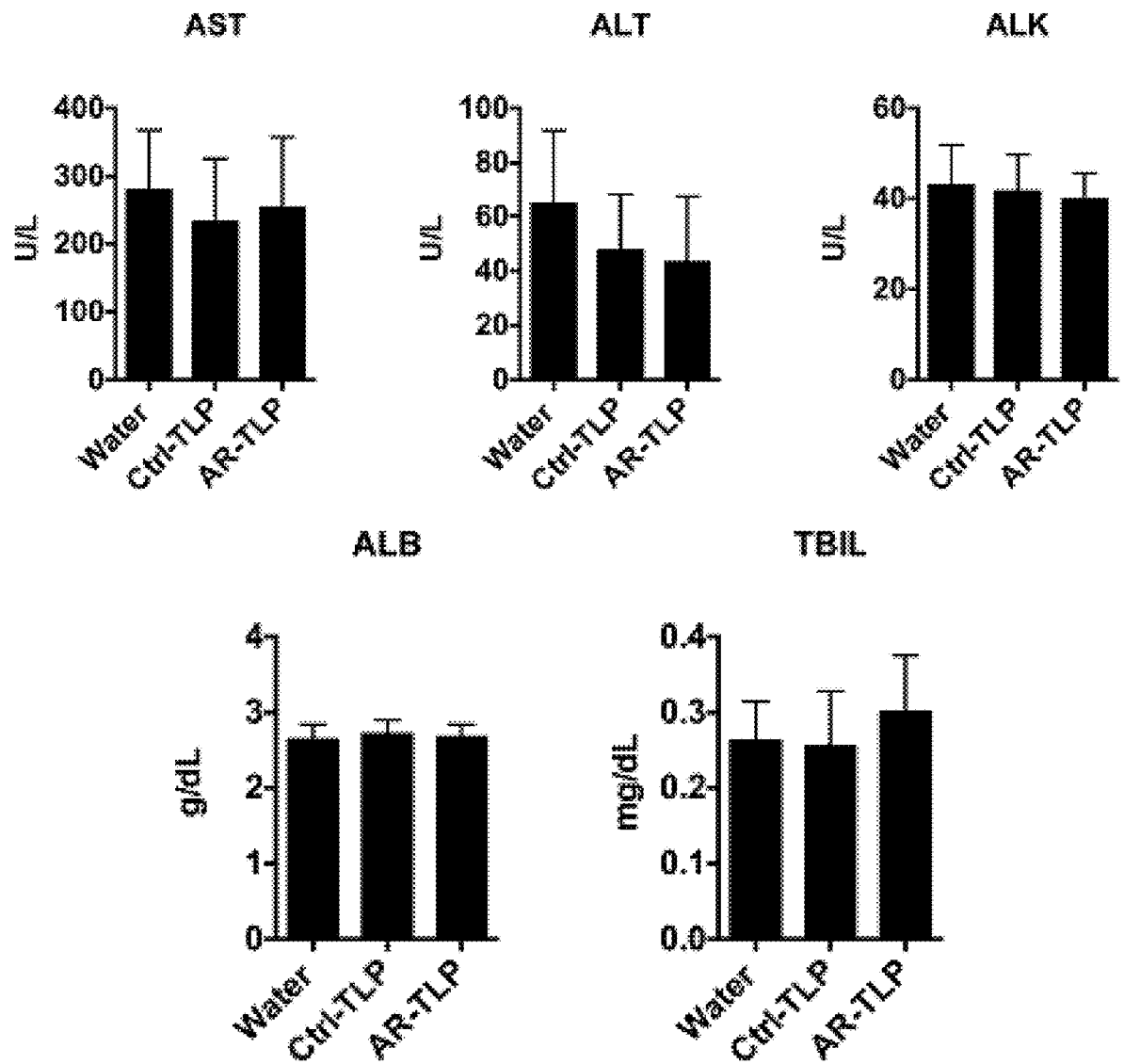

Body weights were maintained and consistent across all study groups (FIG. 12B). To determine any off-target side effects, tissues obtained from representative organs were analyzed by hematoxylin and eosin (H&E) staining followed by microscopic examination, and standard serum parameters were measured. Data show no histopathologic changes in the examined organs (FIG. 12C). No untoward alterations were observed in serum electrolyte or cholesterol levels and kidney function was normal (FIG. 13A). In addition, markers of liver function were normal (FIG. 13B). Ultimately, data collected in mice treated with water and Ctrl-TLPs revealed no side effects confirming a lack of toxicity of the vehicle and control RNA.

Discussion

With a goal of synthesizing efficient in vitro and in vivo siRNA delivery vehicles, the Applicant adhered to a set of design rules that appear critical for natural HDL to deliver nucleic acids, including: 1) preference for ssRNA, 2) charge reconciliation, and 3) active targeting. A pre-synthesized TLP was added to a mixture of DOTAP and ssRNA. Resulting self-assembled siRNA-TLPs are a hybrid between bio-inspired lipoprotein nanoparticles and lipid-RNA structures. Uniquely, delineation of a synthetic method that produces highly efficient siRNA delivery vehicles with a preference for ssRNA complements of a siRNA duplex pair has not been reported. siRNA-TLPs are highly uniform and their synthesis and function are tailorable based upon the appropriate addition of TLP, RNA, and DOTAP. The Applicant clearly shows that the TLPs are absolutely required for siRNA-TLP self-assembly (FIG. 1D and FIG. 7C), active targeting (FIG. 4C), and function (FIG. 1F and FIG. 7D). Presumably, any siRNA duplex pair can be used for self-assembly of siRNA-TLPs, and the particles work to regulate target gene expression in multiple cancer cell types that express SR-B1 (FIG. 10B). In vivo efficacy was achieved in a prostate cancer xenograft model suggesting translational potential. Proof-of-concept in vivo data was gathered using an every-other-day dosing regimen. Significant AR knockdown was observed for up to 96 h in the in vitro model. Also, since gold is biocompatible and the siRNA-TLPs contain a gold core, our data demonstrate no off-target toxicity after 13 intravenous doses of the siRNA-TLPs.

Approaches to develop synthetic versions of HDL are variable and design rules that enable RNA delivery by native or synthetic HDLs are not well understood. Importantly, native HDLs bind and deliver ssRNA, which is not in accordance[12] with the delivery of duplex siRNAs, which is where most delivery strategies are focused. The data described herein demonstrate that formulating ssRNAs of a siRNA pair, either in individual or separate siRNA-TLPs, significantly reduce target gene expression. The findings described herein provide evidence that ssRNA complements of a siRNA duplex can be formulated for systemic siRNA delivery. The data described herein also shows that miRNAs adsorbed to native HDLs localize to the particle surface.[12] Similarly, the siRNA-TLP is formed through a self-assembly process that localizes the RNA to the surface of the particle, and does not encapsulate the RNA inside of a lipid or polymer particle. RNA that is localized to the surface of the siRNA-TLP remains stable and is efficiently delivered to cells for target gene knockdown. RNA stability may result from the anionic nature of the particle and/or because of the solid nature of the particle. The function of siRNA-TLPs may also be enhanced because the RNA is more freely available to the host cell, not encapsulated. Finally, siRNA-TLPs are negatively charged and require the TLP for efficient siRNA delivery and knockdown of target gene expression. Although particles made without the TLP have a charge similar to particles made with the TLP, the particles do not regulate target gene expression. Thus, anionic particles are, actually, poor delivery vehicles for RNA unless the particle is inherently targeted or contains a moiety that enables target cell binding and RNA uptake into the cytoplasm.

In short, the Applicant reports an siRNA delivery vehicle that delivers highly unmodified single strand RNA self-assembled in an anionic particle that is actively targeted. These findings, inspired by native HDL, may enable new approaches for the development of potent and modular siRNA delivery vehicles for personalized medicine.

Methods

Synthesis of Templated Lipoprotein Particles (TLP) and siRNA-TLPs

For TLP synthesis, an aqueous solution of citrate stabilized gold nanoparticles (Au NP) (80 nM, 5±0.75 nm, Ted Pella, Inc.) was mixed with a 5-fold molar excess of purified human apoA-I (400 nM, Meridian Life Sciences, >95% pure by SDS PAGE) in a glass vial. The Au NP/apo A-I mixture was incubated overnight at room temperature (RT) on a flat bottom shaker at low speed. Next, a 1:1 ratio of two phospholipids: 1,2-dipalmitoyl-sn-glycero-3-phosphoethanolamine-N-[3-(2-pyridyldithio)propionate] (PDP-PE) and 1,2-dioleoyl-sn-glycero-3-phophocholine (DOPC) (Avanti Polar Lipids), each dissolved in chloroform ($CHCl_3$, 1 mM), are added to the Au NP/apo A-I solution in 250-fold molar excess to the Au NP. PDP-PE was added first and the solution was vortexed prior to adding DOPC. Next, cholesterol dissolved in $CHCl_3$ (1 mM, Sigma Aldrich) was added in 25-fold molar excess to the Au NP. The mixture was vortexed and briefly sonicated (~2 mins) causing the solution to become opaque and pink in color. The resulting mixture was gradually heated to ~65° C. with constant stirring to evaporate $CHCl_3$ and to transfer the phospholipids onto the particle surface and into the aqueous phase (~20 minutes). The reaction was complete when the solution returned to a transparent red color. The resultant TLPs were incubated overnight at RT and then purified via centrifugation (15,870×g, 50 min). The supernatant was removed and the resulting purified and concentrated TLPs were combined into a single vial. TLPs were stored at 4° C. until use. The concentration of the TLPs was measured using UV-Vis spectroscopy (Agilent 8453) where Au NPs have a characteristic absorption at $\lambda_{max}$=520 nm, and the extinction coefficient for 5 nm Au NPs is $9.696 \times 10^6$ $M^{-1}cm^{-1}$.

To synthesize siRNA-TLP, RNA and 1,2-dioleoyl-3-trimethylammonium-propane (DOTAP) were first mixed. Individual sense and antisense RNA sequences of the AR, control (Ctrl), or EZH2 siRNA (Integrated DNA Technologies) were re-suspended in nuclease free water (500 µM, final). Complement pairs were then mixed in nuclease free water at a concentration enabling direct addition to TLPs (100 nM) at 25-fold molar excess of each RNA sequence (2.5 µM, final per RNA sequence). An ethanolic (EtOH) solution of DOTAP was then added to the RNA mixture to desired DOTAP:RNA molar ratios. In each case the resulting solvent ratio was 9:1, EtOH:water (v/v). The mixture of DOTAP and RNA was briefly sonicated and vortexed (×3) and then incubated at RT for 15 minutes prior to addition to a solution of TLPs in water. After the DOTAP-RNA mixture was added to the TLPs, the solvent mixture was 9:1, water:EtOH (v/v). This solution was incubated overnight at RT with gentle shaking on a flat bottom shaker at low speed. Resulting siRNA-TLPs were purified via centrifugation (15, 870×g, 50 min), the supernatant with unbound starting materials was removed, and the pellets were combined in a single tube to concentrate the siRNA-TLPs. The concentration of the siRNA-TLPs was calculated as described for TLP. For siRNA-TLPs, a strong absorption at $\lambda_{max}$=260 nm confirmed the presence of RNA. For particles synthesized with only one strand of the siRNA duplex pair, the synthetic procedure proceeded similarly; however, twice the amount of RNA was added to the TLPs (5 µM, final).

Single Vs. Double Strand RNA Assembly with DOTAP and TLPs

To investigate if single stranded RNA complements or double stranded siRNA duplexes assembled with TLPs, and the requirement for DOTAP, siRNA-TLPs were synthesized per the above protocol. However, the synthesis was carried out with and without DOTAP and using either water or 1×PBS as the aqueous solvent for siRNA-TLP assembly.

Thermal Denaturation Experiments

Thermal denaturation experiments were performed to measure RNA melting transition temperatures ($T_m$) between 25°-90° C. using an Agilent 8453 UV-Vis spectrophotometer equipped with a Peltier temperature controller. Solutions without RNA, but only with water, EtOH, water:EtOH (v/v), and/or DOTAP had no appreciable absorbance at 260 nm (data not shown).

Quantification of RNA, Apo A-I, DOTAP, DOPC and Cholesterol

To confirm the presence of each of the molecules used to synthesize TLPs and siRNA-TLPs, and to quantify the amount present, the Applicant used molecules labeled with molecular fluorophores to synthesize TLPs and siRNA-TLPs according to the previously described synthetic method. After purification, the amount of each of the fluorescent molecules with reference to standard titration curves developed with each of the fluorescently labeled molecules was measured. More specifically, the number of RNA strands per siRNA-TLP was quantified by incorporating 3' end-labeled (Cy5) RNA sequences. For Cy5, measurements were obtained using a Biotek Synergy 2 fluorescent plate reader using Ex=620/40 nm and Em=680/30 nm. Apo A-I on the particle surface was confirmed by western blotting. For quantification, apoA-I was labeled with Alexa-488 using a commercially available protein labeling kit (Invitrogen) according to the instruction provided by the manufacturer. Measurements were taken using a Biotek Synergy 2 fluorescent plate reader using Ex=485/20 nm and Em=528/20 nm. DOTAP, DOPC, and cholesterol were quantified by incorporating nitrobenzoxadiazole (NBD)-fluorescent analogs of each of the molecules (Avanti Polar Lipids) into the particle synthesis at a 10% dilution. All samples were measured in a 1:1 mixture of EtOH:water (v/v), including the standards. Measurements were taken using a Biotek Synergy 2 fluorescent plate reader using the same settings as for apo A-I measurements.

Dynamic Light Scattering and ζ-Potential Measurements

Hydrodynamic diameter and ζ-potential measurements were performed using TLP or siRNA-TLP in water (10 nM). Triplicate measurements were made under 173° backscatter setting with 10 runs, 30 sec/run/measurement. RNA and RNA-DOTAP mixtures were measured using a concentration of 5 µM RNA. Mixtures containing DOTAP were made where the final concentration of DOTAP=100 µM, 75 µM, 50 µM, and 25 µM to achieve the 40, 30, 20, 10 fold excesses to RNA, respectively. Particle free measurements were taken in 9:1 water:ethanol (v/v) solutions. Measurements were made using a Zetasizer Nano ZS (Malvern). The hydrodynamic diameter data are represented using the number function.

UV-Vis Spectroscopy

A UV-Vis spectrophotometer (Agilent 8453) was used to measure the concentration and stability of NPs to aggregation, The concentration of solutions of Au NPs was determined by measuring the absorbance at ~520 nm (extinction coefficient $9.696 \times 10^6$ $M^{-1}cm^{-1}$; Ted Pella). Disperse colloidal gold nanoparticles strongly absorb and scatter light at ~520 nm ($A_{\lambda max}$). The molar concentration of NPs in the preparations was calculated using the formula: ($A_{\lambda max} \times$ dilution factor)/$9.696 \times 10^6$ $M^{-1}cm^{-1}$. UV-Vis spectrophotometry was also used to determine RNA loading using the strong absorbance of RNA at ~260 nm.

Cell Culture The human lymph node derived prostate cancer LNCaP clone FGC (fast growing colony), androgen receptor positive, androgen sensitive, was obtained from American Type Cell Culture (ATCC). LNCaP cells were grown in RPMI 1640 medium (Invitrogen), supplemented with 10% fetal bovine serum (FBS) and 1% penicillin/streptomycin (Invitrogen). The enzalutamide resistant LNCaP cell line (MDV3100) was a generous gift from Dr. Donald Vander Griend's laboratory (University of Chicago). LNCaP MDV3100 resistant cells were cultured using the same conditions as LNCaP cells; however, 10 μM (final) MDV3100 was added to the growth medium. A375 cells (human malignant melanoma) and MDA-MB-231 cells (human triple negative breast cancer) were obtained from ATCC. Both cell lines were cultured in DMEM (Invitrogen), supplemented with 10% fetal bovine serum (FBS), 1% penicillin/streptomycin (Invitrogen), and 1× Glutamax. 786-O (human renal cell carcinoma) cells were obtained from ATCC and grown under the same conditions as the LNCaP cells. OvCar3 (human ovarian adenocarcinoma) cells were obtained from ATCC and cultured in RPMI 1640 medium (Invitrogen), supplemented with 10% FBS and 1% penicillin/streptomycin (Invitrogen), and 1% insulin. In general, cells were cultured in T75 flasks and plated into appropriate dishes (e.g. 6-well, 24-well, 96-well) 24-48 hours prior to experiments. All cells were incubated at 37° C. in a humidified 5% $CO_2$ incubator.

Conventional siRNA Transfection Prior to all cell transfections, the cell culture media was changed to fresh growth medium. TLPs or RNA-TLPs were directly added to the cultured cells. For comparisons against conventional transfection reagents, LIPOFECTAMINE® RNAiMax transfections were used to treat cells with Ctrl, AR, EZH2, or SR-B1 siRNAs according to the protocol provided by the manufacturer (Invitrogen). Briefly, siRNA was mixed with RNAiMax in OpitMEM media to achieve final concentrations of siRNA ranging from 6-12 nM. siRNA RNAiMAX transfections were optimized to achieve maximal target gene knockdown at 48 hours.

Western Blotting

Cells were plated at $1.5 \times 10^5$ cells/well for all western blotting experiments. Cells were harvested 48 hours following treatment unless otherwise specified. To harvest protein lysate, cells were washed in ice cold 1×PBS and lysed in M-PER (Mammalian Protein Extraction Reagent) supplemented with 1× protease and phosphatase inhibitors (Thermo Scientific). After protein isolation, the bicinchoninic acid assay (BCA) assay was used to quantify total protein. Protein absorbance was measured at 562 nm (BioTek, Synergy 2). Protein concentrations were normalized and then mixed with 4× Laemmli loading buffer containing β-mercaptoethanol (Bio-Rad) and boiled for 10 minutes at 100° C. prior to gel loading. Cellular proteins were resolved by 4-20% SDS-PAGE (200 volts, 32 minutes) and transferred to a 0.2 μm PVDF membrane (65 volts, 1 hour) (Bio-Rad). Membranes were blocked in 5% milk in Tris buffered saline (TBS) and Tween-20 (0.1%) for 1 hour prior to antibody (Ab) addition. Membranes were incubated overnight at 4° C. using rabbit polyclonal antibodies directed against androgen receptor (1:1000, Santa Cruz), beta actin (1:2000, Cell Signaling), EZH2 (1:1000, BD Biosciences), apo A-I (1:1000, Abcam), or SR-BI (1:2000, Abcam). Goat anti-rabbit or goat anti-mouse IgG-HRP (1:2000, Bio-Rad) were used as secondary antibodies. The secondary Ab was applied at RT for 30-60 minutes. Blots were washed (3×) in TBST (0.1% Tween-20) for 10 minutes/ wash prior to protein detection. Proteins were detected using enhanced chemiluminescence (ECL) detection (GE Healthcare Life Sciences) on x-ray film using Konica SRX101A X-Ray Film Processor (MXR Source One Healthcare). Densitometry measurements for western blot analysis were made using ImageJ software.

Transmission Electron Microscopy

A pair of tweezers was used to hold a 200 mesh carbon coated copper grid (Electron Microscopy Sciences) while a 5 μL drop of particles (250 nM) was pipetted onto the grid. The drop was allowed to adsorb to the grid for 10 minutes and the excess solution was wicked away with filter paper. Grids were stained with 5 μL of 4% uranyl acetate (UA) for three minutes. Excess UA was wicked off and the staining was repeated two times. The remaining UA was wicked off and the samples were allowed to dry for 10 minutes. For some transmission electron microscopy experiments, a pair of tweezers was used to hold a 200 mesh carbon coated copper grid (Electron Microscopy Sciences). An equal volume of particles (150×10-9 m) and a 2% uranyl acetate solution were mixed. 10 μL of this solution was added to the grid and allowed to sit for 20 s. The excess volume was removed with a piece of filter paper and the grid was allowed to dry. TEM images were taken with a FEI Tecnai Spirit G2 transmission electron microscope operating at 80 kV. In UA-stained samples, phospholipids are visible as white rings around the electron dense NP. Nikon Elements Imaging Software was used to analyze transmission electron microscopy images to measure the size of TLP, Ctrl-TLP, and AR-TLP. The measurements were taken from three TEM images for each sample, combined, and plotted as histograms using GraphPad Prism.

Cell Viability Assay

Cells were plated at $3 \times 10^4$ cells/well in 96-well plates 48 hours prior to particle treatment. LNCaP cells were treated with increasing concentrations of particles 1, 5, 10, 20 nM. Cell viability was measured at 24, 48, 72, 96 hours using CELLTITER 96® AQ$_{ueous}$ One Solution Cell Proliferation Assay (Promega) according to the instructions provided by the manufacturer. Absorbance was measured at 490 nm (Biotek Synergy 2).

Real-Time Measurements of Particle Uptake and Confluence

LNCaP cells were plated at $6 \times 10^4$ cells/well in 96-well plates 48 hours prior to treatment. LNCaP cells were treated with 20 nM siRNA-TLPs (Ctrl and AR) where the RNA was labeled with Cy5 per the above protocol. Cell confluence and particle uptake were captured for 165 hours using an INCUCYTE® Zoom system and software. Cy5 fluorescence was captured using light-emitting diodes with Ex=585/20 nm and Em=524/20 nm. The entire experiment was performed at 37° C. in a 5% $CO_2$ humidified incubator. siRNA-TLP uptake was measured by fluorescent labeled (Cy5) RNA bound to the siRNA-TLPs.

Real-Time qRT-PCR

Total RNA was isolated from LNCaP cells using RNeasy mini kit (Qiagen). Reverse transcription was preformed using 0.2 μg of RNA and TaqMan Reverse Transcription Kit following the protocol provided by Life Technologies. Real-time qRT-PCR was preformed using TaqMan PCR Master Mix and TaqMan androgen receptor (Catalog # Hs0171172_m1) and β-actin primers/probes for relative mRNA quantification (Life Technologies). qRT-PCR analysis was carried out using an ABI Prism Model 7900HT. Data was analyzed using the comparative $C_t$ method using β-actin as an endogenous control.

Human Serum and Plasma Isolation and Lipoprotein Depletion

Following IRB approval and informed consent, blood samples were collected via venipuncture from an antecubital vein from a healthy donor into a serum separator tube (Becton Dickinson). Serum was isolated by centrifugation (1,000×g for 10 minutes) at 4° C. Serum was aliquoted (250 μL) and stored at −20° C. prior to use. To generate serum depleted of lipoproteins other than HDL, serum was first mixed with a solution of polyethylene glycol [PEG8000, 20% (v/v) solution in 200 mM glycine, pH 7.4] at a 10:4 serum:PEG solution ratio. The sample was gently mixed and incubated at RT for 20 minutes. Next, the samples were centrifuged for 30 minutes (12,700×g) at 4° C. The supernatant, consisting of albumin and HDL was set aside and the pellet was discarded. Human plasma samples were collected similarly to serum; however, blood was collected into heparinized tubes (Becton Dickinson) and then centrifuged for 15 minutes (2,000×g) at 4° C. Resulting plasma was aliquoted (250 µL), used immediately, or stored at −20° C.

siRNA-TLP Function and Stability Post Serum Incubation

TLPs and siRNA-TLPs were incubated with human serum for 1 hour at 37° C. To determine if siRNA exchanged to natural HDL after incubation, human HDL was separated from particles using the isolation assay described above. The albumin/human HDL mixture was directly added to plated LNCaP cells. In addition, experiments were conducted by adding siRNA-TLPs to human serum, incubating for 1 hour, and then directly adding the mixture to LNCaP cells. See FIG. 11 for experimental design.

Nuclease Protection Assay and siRNA-TLP Stability

The stability of RNA in siRNA-TLPs was compared to free RNA in the presence of RNase A (Bio-Rad). siRNA-TLPs (~1 µM RNA) and free RNA sequences (1 µM) were exposed to 2.0 ng/µL RNase A for 0, 5, 15, 30, and 60 minutes at 37° C. Reactions were quenched by addition of 2×RNA loading buffer [90% formamide, 10% glycerol, 1% SDS (w/v), and bromophenol blue] and heated to 65° C. for 3 minutes. Samples were transferred to a pre-run polyacrylamide gel (25% polyacrylamide with 5% stacking layer) and subjected to electrophoretic separation (400 volts for 30 minutes). The gel was stained with ethidium bromide and imaged using ChemiDoc System (Bio-Rad).

siRNA-TLP Stability in Human Plasma

A Cy3 labeled RNA was used to measure the physiologic stability of the siRNA-TLP with comparison to free RNA sequences. siRNA-TLPs (400 nM siRNA-TLP, 1.6 µM RNA of each strand) and free RNA (1.6 µM of each sequence) were exposed to 50% human plasma for 0, 5, 15, 30, and 60 minutes at 37° C. Reactions were quenched by the addition of 2×RNA loading buffer [90% formamide, 10% glycerol, 1% (SDS w/v), and bromophenol blue], and heated to 65° C. for 3 minutes. The samples were transferred to a pre-run polyacrylamide gel and underwent electrophoresis. The gel consisted of 25% polyacrylamide with a 5% stacking layer and ran at room temperature at 400 V for 30 minutes. The Cy3-RNA was detected using a G:BOX Chemi XT4 Imager (Synoptics).

In Vivo Efficacy Studies

All animal experiments were approved by the Institutional Animal Care and Use Committee (IACUC) of Northwestern University, and the studies were performed in accordance with institutional and national guidelines and regulations. LNCaP flank tumor xenografts were established in 6 to 8 week male athymic nude mice by subcutaneous implantation of 1×10$^6$ cells. When tumors reached ~500 mm$^3$, mice were randomized to three treatment groups (i.e. water, Ctrl-TLP, and AR-TLP), n=8 mice/group. Body weights were measured over the course of the study on a standard laboratory scale. Mice were treated every other day with Ctrl-TLPs or AR-TLPs (100 µL, 2 µM siRNA-TLP, ~0.7 mg siRNA/kg) or 100 µL of water for a total of 13 treatments. Treatments were administered via tail vein. When tumors reached ~2000 mm$^3$ in the control groups the study was terminated. Whole blood was obtained by cardiac puncture and collected in heparinized blood collection tubes. Blood samples were separated and subjected to complete blood count and serum chemistry analysis. Tissues (liver, lung, kidney, spleen, heart, brain, adrenal, testes, small intestine, and tumor) were harvested for inductively coupled plasmon mass spectrometry (ICP-MS) and hematoxylin and eosin (H&E) analysis. Fresh tissue sections for ICP-MS were stored immediately at −80° C. until prepped for ICP-MS analysis. ICP-MS analysis was conducted at the Chemistry of Life Processes Core Facility at Northwestern University after digestion of the tissues and Au NPs using strong acid. The amount of Au NPs was quantified with reference to calibrated additional standards. Tissues harvested for H&E were immediately fixed in 10% formalin in PBS. Within 48 hours the tissues were prepped for paraffin embedding and sectioning. Tissue sectioning and H&E staining was performed by the Mouse Histology and Phenotyping Laboratory (MHPL) at Northwestern University. Images of the H&E stained tissues were obtained using a Nikon Eclipse TE2000-U and SPOT imaging software. All images were obtained at 10× magnification.

Tumor Volume Measurements, Blood Analysis, and Serum Chemistry

Tumors were measured using digital calipers over the course of the experiment. The volume was calculated using the equation [Volume=length×width$^2$/2)].$^{48}$ Whole blood collected at time of sacrifice was analyzed for complete blood cell counts using a Hemavet 950FS (Drew Scientific). Plasma was obtained from an aliquot of whole blood and a complete chemistry panel, cholesterol, and liver function analysis was performed by Charles River.

Confocal Fluorescence Microscopy of Tumor Tissues

AR-TLP and Ctrl-TLP were synthesized with Cy3-labeled sense RNA and Cy5-labeled antisense RNA according to the protocol described above. Mice with established LNCaP xenografts (~2000 mm$^3$) (see above) were treated with a single tail vein injection of 100 µL of 2 µM (siRNA-TLP) AR-TLP-Cy3/5 or Ctrl-TLP-Cy3/5, or 100 µL of water. Mice were sacrificed 24 hours following the injection and LNCaP xenograft tumors were harvested and then embedded in optimal cutting temperature (O.C.T) matrix and immediately frozen on a block of dry ice. Tissues were sectioned (10 µm), mounted on glass slides, and counterstained with DAPI diluted (1:50,000) in 1×PBS. Fluoromount-G (Southern Biotech) mounting media and coverslips were applied prior to imaging. Images were acquired using a Nikon C2+ laser scanning confocal microscope (Northwestern University Center for Advanced Microscopy) and analyzed by Nikon Elements software and ImageJ. Images were taken at 60× magnification. Laser settings were consistent across samples.

Statistical Analysis

Data are expressed as means±standard deviation. Blood cell count comparison analyses were performed using unpaired two-tailed t-test with Welch's correction using GraphPad Prism software. An effects model was used to compare changes in tumor volume over time within groups and changes between groups. Group and time were fixed effects and animal was a random effect. The model took into account the repeated measures across animals. Post-hoc comparisons were done using Tukey's method. Statistical significance was considered significant for P≤0.05; * denotes P≤0.05,  P≤0.01,  P≤0.001, **** P≤0.0001.

REFERENCES

8 McMahon, K. M. & Thaxton, C. S. High-density lipoproteins for the systemic delivery of short interfering RNA. *Expert opinion on drug delivery* 11, 231-247, doi: 10.1517/17425247.2014.866089 (2014).

9 Zhang, S., Zhao, B., Jiang, H., Wang, B. & Ma, B. Cationic lipids and polymers mediated vectors for delivery of siRNA. *Journal of controlled release: official journal of the Controlled Release Society* 123, 1-10, doi:10.1016/j.jconrel.2007.07.016 (2007).

10 Lv, H., Zhang, S., Wang, B., Cui, S. & Yan, J. Toxicity of cationic lipids and cationic polymers in gene delivery. *Journal of controlled release: official journal of the Controlled Release Society* 114, 100-109, doi:10.1016/j.jconrel.2006.04.014 (2006).

11 Yang, J. P. & Huang, L. Overcoming the inhibitory effect of serum on lipofection by increasing the charge ratio of cationic liposome to DNA. *Gene Ther* 4, 950-960, doi:10.1038/sj.gt.3300485 (1997).

12 Vickers, K. C., Palmisano, B. T., Shoucri, B. M., Shamburek, R. D. & Remaley, A. T. MicroRNAs are transported in plasma and delivered to recipient cells by high-density lipoproteins. *Nat Cell Biol* 13, 423-U182, doi:Doi 10.1038/Ncb2210 (2011).

13 Tabet, F. et al. HDL-transferred microRNA-223 regulates ICAM-1 expression in endothelial cells. *Nature communications* 5, 3292, doi:10.1038/ncomms4292 (2014).

14 Acton, S. et al. Identification of scavenger receptor SR-BI as a high density lipoprotein receptor. *Science* 271, 518-520 (1996).

15 Wolfrum, C. et al. Mechanisms and optimization of in vivo delivery of lipophilic siRNAs. *Nature biotechnology* 25, 1149-1157, doi:10.1038/nbt1339 (2007).

16 Douam, F., Lavillette, D. & Cosset, F. L. The mechanism of HCV entry into host cells. *Prog Mol Biol Transl Sci* 129, 63-107, doi:10.1016/bs.pmbts.2014.10.003 (2015).

17 Plebanek, M. P. et al. Nanoparticle Targeting and Cholesterol Flux Through Scavenger Receptor Type B-1 Inhibits Cellular Exosome Uptake. *Sci Rep* 5, 15724, doi:10.1038/srep15724 (2015).

18 Van Eck, M. et al. Scavenger receptor BI facilitates the metabolism of VLDL lipoproteins in vivo. *Journal of lipid research* 49, 136-146, doi:10.1194/jlr.M700355-JLR200 (2008).

19 McMahon, K. M. et al. Biomimetic high density lipoprotein nanoparticles for nucleic acid delivery. *Nano letters* 11, 1208-1214, doi:10.1021/nl1041947 (2011).

20 Zhang, Z. et al. HDL-mimicking peptide-lipid nanoparticles with improved tumor targeting. *Small* 6, 430-437, doi:10.1002/smll.200901515 (2010).

21 Shahzad, M. M. et al. Targeted delivery of small interfering RNA using reconstituted high-density lipoprotein nanoparticles. *Neoplasia* 13, 309-319 (2011).

22 Ding, Y. et al. A biomimetic nanovector-mediated targeted cholesterol-conjugated siRNA delivery for tumor gene therapy. *Biomaterials* 33, 8893-8905, doi:10.1016/j.biomaterials.2012.08.057 (2012).

23 Nakayama, T. et al. Harnessing a physiologic mechanism for siRNA delivery with mimetic lipoprotein particles. *Molecular therapy: the journal of the American Society of Gene Therapy* 20, 1582-1589, doi:10.1038/mt.2012.33 (2012).

24 Mei, X. & Atkinson, D. Lipid-free Apolipoprotein A-I Structure: Insights into HDL Formation and Atherosclerosis Development. *Arch Med Res* 46, 351-360, doi:10.1016/j.arcmed.2015.05.012 (2015).

25 Maksymovych, P., Sorescu, D. C. & Yates, J. T., Jr. Gold-adatom-mediated bonding in self-assembled short-chain alkanethiolate species on the Au(111) surface. *Phys Rev Lett* 97, 146103, doi:10.1103/PhysRevLett.97.146103 (2006).

26 Sun, W. et al. Mesophase in a thiolate-containing diacyl phospholipid self-assembled monolayer. *Langmuir: the ACS journal of surfaces and colloids* 31, 3232-3241, doi:10.1021/la504822q (2015).

27 Luthi, A. J. et al. Robust passive and active efflux of cellular cholesterol to a designer functional mimic of high density lipoprotein. *Journal of lipid research* 56, 972-985, doi:10.1194/jlr.M054635 (2015).

28 Cheng, X. & Lee, R. J. The role of helper lipids in lipid nanoparticles (LNPs) designed for oligonucleotide delivery. *Advanced drug delivery reviews* 99, 129-137, doi:10.1016/j.addr.2016.01.022 (2016).

29 Bergerat, J. P. & Ceraline, J. Pleiotropic functional properties of androgen receptor mutants in prostate cancer. *Hum Mutat* 30, 145-157, doi:10.1002/humu.20848 (2009).

30 Suga, K., Tanabe, T., Tomita, H., Shimanouchi, T. & Umakoshi, H. Conformational change of single-stranded RNAs induced by liposome binding. *Nucleic Acids Res* 39, 8891-8900, doi:10.1093/nar/gkr568 (2011).

31 Daniel, M. C. & Astruc, D. Gold nanoparticles: assembly, supramolecular chemistry, quantum-size-related properties, and applications toward biology, catalysis, and nanotechnology. *Chemical reviews* 104, 293-346, doi:10.1021/cr030698+(2004).

32 Sioud, M. & Sorensen, D. R. Cationic liposome-mediated delivery of siRNAs in adult mice. *Biochem Biophys Res Commun* 312, 1220-1225 (2003).

33 Sorensen, D. R., Leirdal, M. & Sioud, M. Gene silencing by systemic delivery of synthetic siRNAs in adult mice. *J Mol Biol* 327, 761-766 (2003).

34 Fire, A. Z. Gene silencing by double-stranded RNA (Nobel Lecture). *Angewandte Chemie* 46, 6966-6984, doi:10.1002/anie.200701979 (2007).

35 Fire, A. et al. Potent and specific genetic interference by double-stranded RNA in *Caenorhabditis elegans*. *Nature* 391, 806-811, doi:10.1038/35888 (1998).

36 Schalken, J. & Fitzpatrick, J. M. Enzalutamide: targeting the androgen signalling pathway in metastatic castration-resistant prostate cancer. *BJU Int* 117, 215-225, doi:10.1111/bju.13123 (2016).

37 Chatterjee, B. The role of the androgen receptor in the development of prostatic hyperplasia and prostate cancer. *Mol Cell Biochem* 253, 89-101 (2003).

38 Rao, Z. Y. et al. EZH2 supports ovarian carcinoma cell invasion and/or metastasis via regulation of TGF-beta1 and is a predictor of outcome in ovarian carcinoma patients. *Carcinogenesis* 31, 1576-1583, doi:10.1093/carcin/bgq150 (2010).

39 Yang, Y. A. & Yu, J. EZH2, an epigenetic driver of prostate cancer. *Protein Cell* 4, 331-341, doi:10.1007/s13238-013-2093-2 (2013).

40 Wang, Y. et al. Overexpression of YB1 and EZH2 are associated with cancer metastasis and poor prognosis in renal cell carcinomas. *Tumour Biol* 36, 7159-7166, doi:10.1007/s13277-015-3417-z (2015).

41 Yoo, K. H. & Hennighausen, L. EZH2 methyltransferase and H3K27 methylation in breast cancer. *Int J Biol Sci* 8, 59-65 (2012).

42 Purdue, M. P. et al. Genome-wide association study of renal cell carcinoma identifies two susceptibility loci on 2p21 and 11q13.3. *Nat Genet* 43, 60-65, doi:10.1038/ng.723 (2011).

43 de Gonzalo-Calvo, D. et al. Intratumor cholesteryl ester accumulation is associated with human breast cancer proliferation and aggressive potential: a molecular and clinicopathological study. *BMC Cancer* 15, 460, doi: 10.1186/s12885-015-1469-5 (2015).
44 Schorghofer, D. et al. The HDL receptor SR-BI is associated with human prostate cancer progression and plays a possible role in establishing androgen independence. *Reprod Biol Endocrinol* 13, 88, doi:10.1186/s12958-015-0087-z (2015).
45 Twiddy, A. L., Cox, M. E. & Wasan, K. M. Knockdown of scavenger receptor class B type I reduces prostate specific antigen secretion and viability of prostate cancer cells. *Prostate* 72, 955-965, doi:10.1002/pros.21499 (2012).
46 Krycer, J. R. & Brown, A. J. Does changing androgen receptor status during prostate cancer development impact upon cholesterol homeostasis? *PLoS One* 8, e54007, doi:10.1371/journal.pone.0054007 (2013).
47 Chuang, K. H. et al. Neutropenia with impaired host defense against microbial infection in mice lacking androgen receptor. *J Exp Med* 206, 1181-1199, doi:10.1084/jem.20082521 (2009).
48 Brodin, N. P. et al. Semi-automatic cone beam CT segmentation of in vivo pre-clinical subcutaneous tumours provides an efficient non-invasive alternative for tumour volume measurements. *Br J Radiol* 88, 20140776, doi:10.1259/bjr.20140776 (2015).
49 Green, S. M. et al. Mol. Androgen action and metabolism in prostate cancer. *Cell Endocrinol.* 360, 3-13 (2012).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An anionic nanostructure aggregate, comprising: an aggregate of cationic lipid-nucleic acid complexes and templated lipoprotein particles (TLP), wherein the TLP comprises an anionic TLP which is a synthetic HDL having an inert core, a lipid shell surrounding the inert core, and an apolipoprotein functionalized to the inert core; and the cationic lipid-nucleic acid complex, comprised of single stranded antisense and sense RNA of an siRNA duplex, each complexed with a cationic lipid, and wherein the aggregate of cationic lipid-nucleic acid complexes and TLPs has a negative ζ-potential and forms the anionic nanostructure aggregate.

2. The nanostructure of claim 1, wherein the inert core is a metal.

3. The nanostructure of claim 1, wherein the inert core is gold.

4. The nanostructure of claim 1, wherein the lipid shell comprises phospholipids, and wherein the phospholipids are 1,2-dioleoyl-sn-glycero-3-phophocholine (DOPC) and 1,2-dipalmitoyl-sn-glycero-3-phosphoethanolamine-N-[3-(2-pyridyldithio)propionate] (PDP-PE).

5. The nanostructure of claim 1, wherein the apolipoprotein is apolipoprotein A-1 (apo A-1).

6. The nanostructure of claim 1, wherein the nanostructure further comprises cholesterol.

7. The nanostructure of claim 1, wherein the RNA in the nanostructure is more stable than free RNA.

8. The nanostructure of claim 1, wherein the nanostructure comprises alternating layers of 1,2-dioleoyl-3-trimethylammonium-propane (DOTAP) and RNA.

9. The nanostructure of claim 1, wherein the nanostructure is solid.

10. The nanostructure of claim 1, wherein the RNA is not chemically modified.

11. The nanostructure of claim 1, wherein the sense and antisense RNA are present in nearly equimolar amounts.

12. The nanostructure of claim 1, wherein the sense and antisense RNA are present in about an 1:2 ratio.

13. The nanostructure of claim 1, wherein the sense and antisense RNA are present in about an 1:1 ratio.

14. The nanostructure of claim 1, wherein the sense and antisense RNA are present in about a 2:1 ratio.

15. The nanostructure of claim 1, wherein the RNA is mixed with TLP in a molar ratio of 5:1, 15:1 or 25:1.

16. The nanostructure of claim 15, wherein the RNA is mixed with TLP in a molar ratio of 25:1.

17. The nanostructure of claim 1, wherein the cationic lipid is DOTAP.

18. The nanostructure of claim 17, wherein the DOTAP is mixed with RNA in a molar ratio of 10:1, 20:1, 30:1 or 40:1.

19. A method for delivering siRNA to a cell comprising contacting a cell with the nanostructure of claim 1 to deliver siRNA to the cell.

20. The nanostructure of claim 1, wherein the nanostructure further delivers an adjuvant.

21. The nanostructure of claim 1, wherein the nanostructure further comprises an antigen that enhances antigen presentation in a cell.

22. The nanostructure of claim 1, wherein the lipid shell comprises phospholipids, and wherein the phospholipids contain a di-sulfide headgroup.

23. A composition, comprising:
a mixture of siRNA-templated lipoprotein particles (siRNA-TLPs), comprised of cationic lipid-RNA complexes aggregated with TLPs, wherein the cationic lipid-RNA complex is comprised of a single stranded antisense RNA or a single stranded sense RNA of an siRNA duplex complexed with a cationic lipid; wherein each TLP comprises a core, a lipid shell surrounding the core, an apolipoprotein, and a mixture of two phospholipids in the lipid shell; and wherein the siRNA-TLPs have a negative $\zeta$-potential.

24. The nanostructure of claim 1, wherein the lipid shell comprises a mixture of two phospholipids.

25. The composition of claim 23, wherein the RNA is not chemically modified.

26. The composition of claim 23, wherein the sense and antisense RNA are present in nearly equimolar amounts.

27. The composition of claim 23, wherein the RNA is mixed with TLP in a molar ratio of 25:1.

* * * * *